US011685908B2

(12) United States Patent
Noble et al.

(10) Patent No.: US 11,685,908 B2
(45) Date of Patent: Jun. 27, 2023

(54) PRENYLTRANSFERASE VARIANTS AND METHODS FOR PRODUCTION OF PRENYLATED AROMATIC COMPOUNDS

(71) Applicant: Genomatica, Inc., San Diego, CA (US)

(72) Inventors: Michael A. Noble, San Diego, CA (US); Kevin G. Hoff, San Diego, CA (US); Anna Lechner, San Diego, CA (US); Harish Nagarajan, San Diego, CA (US)

(73) Assignee: Genomatica, Inc., San Diego, CA (US)

( * ) Notice: Subject to any disclaimer, the term of this patent is extended or adjusted under 35 U.S.C. 154(b) by 0 days.

(21) Appl. No.: 16/978,629

(22) PCT Filed: Mar. 8, 2019

(86) PCT No.: PCT/US2019/021448

§ 371 (c)(1),
(2) Date: Sep. 4, 2020

(87) PCT Pub. No.: WO2019/173770

PCT Pub. Date: Sep. 12, 2019

(65) Prior Publication Data

US 2021/0254030 A1 Aug. 19, 2021

Related U.S. Application Data

(60) Provisional application No. 62/640,384, filed on Mar. 8, 2018.

(51) Int. Cl.
*C12N 9/10* (2006.01)
*C12P 7/22* (2006.01)
*C12P 7/42* (2006.01)

(52) U.S. Cl.
CPC .............. *C12N 9/1085* (2013.01); *C12P 7/22* (2013.01); *C12P 7/42* (2013.01)

(58) Field of Classification Search
CPC .................................................... C12N 9/1085
See application file for complete search history.

(56) References Cited

U.S. PATENT DOCUMENTS

2015/0128301 A1 5/2015 Page et al.
2021/0254030 A1* 8/2021 Noble .................. C12N 9/1085

FOREIGN PATENT DOCUMENTS

WO 2011017798 A1 2/2011

OTHER PUBLICATIONS

GenBank Accession No. POX52001.1, published Feb. 6, 2018 (Year: 2018).*
GenBank Accession No. AQU65790.1, published Mar. 2, 2017 (Year: 2017).*
GenBank Accession No. AUH41460.1, published Dec. 23, 2017 (Year: 2017).*
GenBank Accession No. SHN18452.1, published Dec. 2, 2016 (Year: 2016).*
GenBank Accession No. AFS18550.1, published Sep. 24, 2012 (Year: 2012).*
GenBank Accession No. 1ZB6_A, published Oct. 31, 2012 (Year: 2012).*
Carvalho et al. (2017) "Designing microorganisms for heterologous biosynthesis of cannabinoids", FEMS Yeast Research, 17:1-11.
Zirpel et al. (2017) "Engineering yeasts as platform organisms for cannabinoid biosynthesis", Journal of Biotechnology, 259:204-212.
Muntendam, R., (2015) "Metabolomics and bioanalysis of terpenoid derived secondary metabolites", Analysis of Cannabis saliva L metabolite production and prenylases for cannabinoid production, University of Groningen, Thesis, pp. 1-179.
Schreckenbach, H. F. (2017) "Enzymatische Oligomerisierung von Alkendiphosphaten", Dissertation, zur Erlangung des akademischen Grades, doctor rerum naturalium (Dr. rer. Nat.) der Naturwissenschaftlichen Fakultat II—Chemie und Physik der Martin-Luther-Universitat Halle-Wittenberg, pp. 1-159, (Dissertation in English).
NCBI database accession No. AB187169.1; Streptomyces sp. CL 190 gene for prenyltransferase, complete cds, 1 page.
Kuzuyama et al. (2005) "Structural basis for the promiscuous biosynthetic prenylation of aromatic natural products", Nature, 435:983-987.
Gagne et al. (2012) "Identification of olivetolic acid cyclase from Cannabis sativa reveals a unique catalytic route to plant polyketides", PNAS, 109:12811-12816.
Kumano et al. (2008) "Chemoenzymatic syntheses of prenylated aromatic small molecules using Streptomyces prenyltransferases with relaxed substrate specificities", Bioorganic & Medicinal Chemistry, 16:8117-8126.

(Continued)

*Primary Examiner* — Yong D Pak
(74) *Attorney, Agent, or Firm* — Kagan Binder, PLLC

(57) ABSTRACT

Described herein are prenyltransferases including non-natural variants thereof having at least one amino acid substitution as compared to its corresponding natural or unmodified prenyltransferases and that are capable of at least two-fold greater rate of formation of cannabinoids such as cannabigerolic acid, cannabigerovarinic acid, cannabigerorcinic acid, and cannabigerol, as compared to a wild type control. Prenyltransferase variants also demonstrated regioselectivity to desired cannabinoid isomers such as CDBA (3-GOLA), 3-GDVA, 3-GOSA, and CBG (2-GOL). The prenyltransferase variants can be used to form prenylated aromatic compounds, and can be expressed in an engineered microbe having a pathway to such compounds, which include 3-GOLA, 3-GDVA, 3-GOSA, and CBG. 3-GOLA can be used for the preparation of cannabigerol (CBG), which can be used in therapeutic compositions.

18 Claims, 9 Drawing Sheets

Specification includes a Sequence Listing.

(56) References Cited

OTHER PUBLICATIONS

Yang et al. (2012) "Catalytic Mechanism of Aromatic Prenylation by NphB", Biochechemistry, 51:2606-2618 (NIH Author Manuscript, 28 pages).
Valliere et al. (2019) "A cell-free platform for the prenylation of natural products and application to cannabinoid production", Nature Communication, 10:1-9.

* cited by examiner

| # | function | example |
|---|---|---|
| 1 | Polyketide synthase | ols |
| 2 | Polyketide synthase | ols |
| 3 | Polyketide synthase | ols |
| 4 | Olivetolid acid cyclase | oac |
| 5 | Aromatic prenyltransferase | SEQ ID NO:1 |
| 6 | MPE/DOXP pathway | |
| 7 | Mevalonate pathway | |

Fig. 3
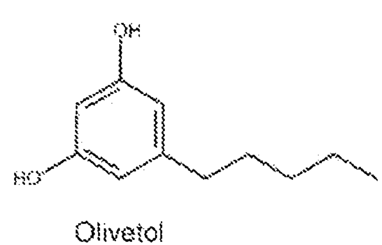
Olivetol
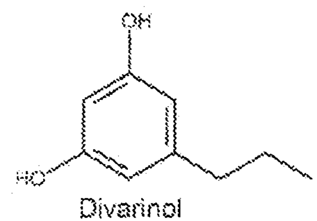
Divarinol
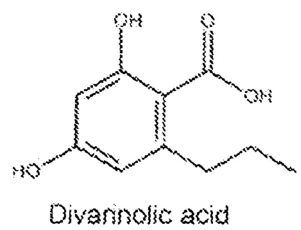
Divarinolic acid
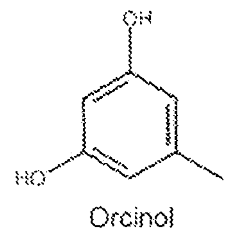
Orcinol
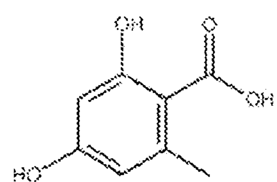
Orsellinic acid
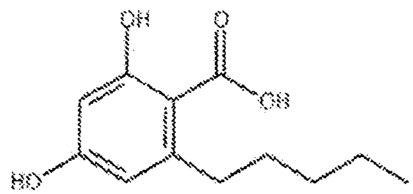
Olivetolic acid

Fig. 4

```
1   MSGAADVERV YAAMEEAAGL LGVTCAREKI YPLLTEFQDT LTDGVVVFSM ASGRRSTELD
61  FSISVPTSQG DPYATVVDKG LFPATGHPVD DLLADTQKHL PVSMFAIDGE VTGGFKKTYA
121 FFPTDDMPGV AQLSAIPSMP SSVAENAELF ARYGLDKVQM TSMDYKKRQV NLYFSELSEQ
181 TLAPESVLAL VRELGLHVPT ELGLEFCKRS FSVYPTLNWD TGKIDRLCFA VISTDPTLVP
241 STDERDIEQF RHYGTKAPYA YVGENRTLVY GLTLSPTEEY YKLGAYYHIT DIQRRLLKAF
301 DALED
```

Fig. 5

```
                 1           10          20          30          40          50          60
                 |           |           |           |           |           |           |
SEQ ID NO:1   ------------------------------------------------------------
SEQ ID NO:2   ------------------------------------------------------------
SEQ ID NO:3   ------------------------------------------------------------
SEQ ID NO:4   ------------------------------------------------------------
SEQ ID NO:5   ------------------------------------------------------------
SEQ ID NO:6   ------------------------------------------------------------
SEQ ID NO:7   ------------------------------------------------------------
SEQ ID NO:8   ------------------------------------------------------------
SEQ ID NO:9   ------------------------------------------------------------
SEQ ID NO:10  ------------------------------------------------------------
SEQ ID NO:11  ------------------------------------------------------------
SEQ ID NO:12  ------------------------------------------------------------
SEQ ID NO:13  ------------------------------------------------------------
SEQ ID NO:14  MCVPGSPARRSGSHGWLERTAKPAPTRGIVGAKVRSQTNERRAPGAITVTCPVQQRSTQP
SEQ ID NO:15  ------------------------------------------------------------

SEQ ID NO:1   ---------------MSGAADVERVYAAMEEAAGLLGVTCARERIYPLLTEFQDTLIDG--V
SEQ ID NO:2   ---------------MSEAADVERVYAAMEEAAGLLGVACRRDKIYPLLSEFQDTLVEGGAV
SEQ ID NO:3   ---------------MSGAADVERVYAAMEEAAGLLDVNCARENIYPLLEVFQDTLTDG--V
SEQ ID NO:4   ---------------MSGAADVERVYAAMEEAAGLLDVSCAREZIYPLLTVFQDTLTDG--V
SEQ ID NO:5   ---------------MSGAADVERVYAAMEEAAGLLGVGCAREIIYPLLIVFQDTLIDG--V
SEQ ID NO:6   ---------------MSAAAEVERVYAAMEEAAGLLDVACSPENVRPILTAFQDVLSDG--V
SEQ ID NO:7   ---------------MSGAAEVERVYSAMEESAGLLDVACSREEIQPILTAFQDVLADG--V
SEQ ID NO:8   ---------------MSGAADVERVYSAMEEAAPLLDITVRREVREALEAYHEVLADA--V
SEQ ID NO:9   ---------------MSGAADVERVYSAMEEAAGLLNVPVARDRIRPVLTAYQDALADA--V
SEQ ID NO:10  ---------------MSGAADVERVYSAMEEAAGLLNVPVARDRINPVLTAYQDALADA--V
SEQ ID NO:11  ---------------MSGANDVERVYSAMEEAAGLLNVPVARDRIRPVLTAYQEALADA--V
SEQ ID NO:12  ---------------MSGANDVERVYSAMEEAAGLLGVPVARERVRPVLTAYQDALADA--V
SEQ ID NO:13  ---------------MSKATEVDRVYAAVEEAAALAGTTCAGDRVRPVLTGHQDLLSEA--V
SEQ ID NO:14  EQADEQLAHVGDAMSGAADVERVYSAMEEAAGLLDLTCAREEILPILDAYEEALADS--V
SEQ ID NO:15  ---------------MVGSTEVEEVYSALEKSAGLVGVPCHRDNVPEALSTYQDALGEA--V

SEQ ID NO:1   VVFSMAS-GRESTELDFSISVPTSQGDPYATVVEKGLFPATGHPVDSLLADTQKHLPVSM
SEQ ID NO:2   VVFSMAS-GRESTELDFSISVPTSHGDPYATVVEKGLFPATGHPVDSLLADTQKHLPVSM
SEQ ID NO:3   VVFSMAS-GRPSTELDFSISVPTSQGDPYATVVREGLFRATGHPVDELLADTQKHLPVSM
SEQ ID NO:4   VVFSMAS-GRRSTELDFSISVPVSQGDPYATVVREGLFRATGSPVDELLADTVKHLPVSM
SEQ ID NO:5   VVFSMAS-GRRSTELDFSISVPVSQGDPYATVVREGLFQATGSPVDELLADTVAHLPVSM
SEQ ID NO:6   IVFSMAS-GRHATELDFSISVPADHGDPYAALAEHGLIPETGHPVGNLLADTQKALPVSM
SEQ ID NO:7   IVFSMAS-GRHATELDFSISVPAGHGDPYAAALERGLIPATGHPVGSLLASTQKALPVSM
SEQ ID NO:8   VVFSMAS-GRYATELDFSISVPAEAGDPYRVALANGLTPRTDHPVGRLLADTQEHLPVSM
SEQ ID NO:9   IVFSMAG-GRRSTELDFSISVPTDHGDPFTTALERGLTEKENHSVDNLLAELRDGFPLGM
SEQ ID NO:10  IVFSMAG-GRRSTELDFSISVPTDHGDPFTTALEAGLTEKENHPVDNLLAELRDGFPLGM
SEQ ID NO:11  VVFSMAG-GRRATELDFSISVPTDLGDPFTTALARGLTEKENHPVDNLLAELTDGFRLGM
SEQ ID NO:12  VVFSMAG-GRPATELDFSISVPTDHGDPFTTALQRGLTEKTGHPVDNLLAELREGFPLGM
SEQ ID NO:13  IVFSMTASGSHSGGLDLSMTVPAEHVDPYSFALSEGLIEPIDHPVGEVISDFQERFPIGM
SEQ ID NO:14  IVFSMSG-GDRSAELDFSFTIPSGDVDPYAFGPSIGIPIETDHPIASLLSDTGEQCPVAM
SEQ ID NO:15  IVFSVATDEEHAGEADYTLTVPTDGADQYALALAEGLIPETDHPVATELAAVQERCPVAG

SEQ ID NO:1   FAIDGEVTGGFKKTYAFFPTDDMPGVAQLSAIPSMPASVAENAELFARYGLD-KVQMTSM
SEQ ID NO:2   FAIDGEVTGGFKKTYAFFPTDDMPGVAELSAIPSMPASVAENAELFARYGLD-KVQMTSM
SEQ ID NO:3   FAIDGEVTGGFKKTYAFFPTDDMPGVAQLTSIPSMPASVAENAELFARYGLD-KVQMTSM
SEQ ID NO:4   FAIDGEVTGGFKKTYAFFPTDDMPGVAQLTEIPSMPASVAENAELFARYGLD-KVQMTSM
SEQ ID NO:5   FAIDGEVTGGFKKTYAFFPTDDMPGVAQLAAIPSMPASVAENAELFARYGLD-KVQMTSM
SEQ ID NO:6   FAVDGEVTGGFKKTYAFFPTDDMPGLAQLIDIPSMPPSVAENAELFARYGLD-KVQMTSL
SEQ ID NO:7   FAVDGEVTGGFKKTYAFFPTDDMPGLAQLIDIPSMPPSVAENAELFGRYGLD-KVQMTSL
```

Fig. 5 (cont.)

```
SEQ ID NO:8   FAFDGEIIGGFKKTYAFFPTNDLQKASKLAEIPGMPDSVKEMADLFARYGLD-KTQMTSI
SEQ ID NO:9   YAIIDNVTTGFKKAYASFPTNEPQSLIAALSLPGMPESAKANRELFARYGLD-KVQMTSV
SEQ ID NO:10  YAIDGKVTTGFKKAYASFPINEKQPLTAALLDLPGMPESRRANAELFAKYGLD-KVQMVSV
SEQ ID NO:11  YAIDGNVTTGFKKTYASFPINEKQPLTAALLDVPGMPESARANAELFARYGLD-KVQMVSV
SEQ ID NO:12  YAIDGKVSTGFKKTYASFPIKEPQPLTTLLDVTGMPASARANAKLFANYGLD-KVQMVSV
SEQ ID NO:13  VGIDVIVAGGFKKAYAAFPSNGLRELKQLFDLPGKFSAAAEFAELFARYGLD-KVSQVST
SEQ ID NO:14  YPIDGEVSGGFKKTYAAFPINDLAELPKLYAVPGMPAAVAENAELFARYGLD-KVQGISI
SEQ ID NO:15  YAVIDGVVGGFKKIAEFPPQIDLQGLAKLAKIPGMPRALAENAALFARKGLDKEVTMLGI

SEQ ID NO:1   DYKKRQVNLYFSELSEQTLAPESVLALVRELGLNVPTELGLEFCKRSFSVYPTLNWDTGK
SEQ ID NO:2   DYKKPQVNLIFSELSAQTLEAISVLALVRELGLNVPNELGLKFCKRSFSVYPTLNWETGK
SEQ ID NO:3   DYKKRQVNLYFSDLEQEYLQPEAVVALAKELGLQVPSELGLEFCKRSFAVYPTLNWDTGK
SEQ ID NO:4   DYKKRQVNLYFSDLKQEYLQPEAVVALAKELGLQVPSELGLEFCKRSFAVYPTLNWDTGK
SEQ ID NO:5   DYKKRQVNLYFSELKQEYLQPESVVALARELGLKVPGELGLEFCKRSFAVYPTLNWDTGK
SEQ ID NO:6   DYKKNQVNLYFSHLSQEFLAPESVLSMVKEMGLELPGKLGLKFAKRSFAIYPTLNWESGK
SEQ ID NO:7   DYKKNQVNLYFSHLNEEFLQPESVQRMVAEMGLQLPADKGLAFAKRSFAVYPTLSWDGAK
SEQ ID NO:8   DYKKKAVNLYFSEMSPDILGPDTVRSMLRDMGLPKTGEVGLTFAPRSFSVYPTLNWKTGK
SEQ ID NO:9   DYKEKQVNLYFSELKADHLTPEQVKKIAAENGLVEPIDNALDFAIGSFKVYPTLGYLSDV
SEQ ID NO:10  DYPKRQVNLYFSDLNADHLTPEEVKSTASENGLVEPIDNALDFATGSFAVYPTLSYDSDI
SEQ ID NO:11  DYSKRQVNLYFSELDTDYLQPENVKSLARETGLVEPIENGLDFASGSFAVYPTLGYDNDI
SEQ ID NO:12  DYPKRQVNLYFSELNIDYLQPEAQVKALAAEMGLIEPSELGLEFAKGSFAVYPTLSYDSDA
SEQ ID NO:13  DYKKREIVLYCDPATTEELDPSVVQSMLADMGLKLAPRQGLEFAKKIFAEYPTLNWDGSE
SEQ ID NO:14  DYQKKQVNLYCGDIPAESLEPETVRSMLRENGLPEPSEEGLEFVPKSFAVYPTLSWDSSR
SEQ ID NO:15  DYQKESVNLYFGKLPEECLQPDSIRAILRDIGLPEPTEPMLEFAKKSFAIYVTLSWDAAK

SEQ ID NO:1   IDRLCFAV-------ISTDPTLVPSTDERDIEQPRHYGTKAPYAYVGENRTLVYGLTLSPT
SEQ ID NO:2   IDRLCFAV-------ISNDPTLVPSSDEQDIEKPHNYATKAPYAYVGENRTLVYGLTLSPK
SEQ ID NO:3   IDRLCFAA-------ISTDPTLVPSTDERDIEKPRKYATKAPYAYVGEKPTLVYGLTLSPT
SEQ ID NO:4   IDRLCFAA-------ISTDPTLVPSTDERDIEKPRKYATKAPYAYVGENRTLVYGLTLSST
SEQ ID NO:5   IDRLCFAA-------ISTDPTLVPSEDERDIENPRNYAIKAPYAYVGENRSLVYGLTLSST
SEQ ID NO:6   IERLCFAV-------ISTDPGLVPAPDEADLALEKTYANNAPYAYAGEKRTLVYGLTLSPT
SEQ ID NO:7   IERLCFAV-------ISTDPTLAPAQEQADLDLPKTYANNAPYAYAGEKRTLVYGLTLSPS
SEQ ID NO:8   IERLCFAV-------ISTDPTLAPSKEKAEDLAKPSKYANNAPYAYAGEKRTLVYGLTLTPR
SEQ ID NO:9   VDRITYAV-------ISVDPTLAPTTSEPKKTQLPKTYANNAPYAYAGENRKLVYGFTLTSK
SEQ ID NO:10  VDRITYAV-------ISVDPTLAPTTSEPKKIQLPKTYANNAPYAYAGENRTLVYGFTLTSK
SEQ ID NO:11  VDRITYAV-------ISVDPTLAPTKSEPEVPQLPKTYAKKAPYAYAGENRSLVYGVILTSK
SEQ ID NO:12  IDRLCLAV-------ISSDPTLAPTTSEPEVTQPKTTANNAPYAYAGEKRTLVYGLTLTPK
SEQ ID NO:13  IVRICEAV-------ITTDPATTPTRSEDELDQPKKYASTAPYAYVGEQRALVYGLALSPE
SEQ ID NO:14  IERICFAV-------ISTDPTLAPTRVESDVALPKKYAKDAPYAYLGEKRELIYGLAVSPT
SEQ ID NO:15  TERICFAVPPGADLITLDPSALPARIAPEIENP---ANNSPYAYPGD-RMLVYGFVTNSPE

SEQ ID NO:1   EEYYKLGAYYHKIIDIQRKLLHAFDALED--
SEQ ID NO:2   EEYYKLGKYYHKITDVQRSLLKAFDSLED--
SEQ ID NO:3   EEYYKLGAYYHKIIDIQRQLLKAFDALED--
SEQ ID NO:4   EEYYKLGAYYHKIIDIQRQLLKAFDALED--
SEQ ID NO:5   EEYYKLGAYYHKIIDIQRQLLKAFDALED--
SEQ ID NO:6   EEYYKLGSYYQKIIDIQRTLLKAFDALYD--
SEQ ID NO:7   EEYYKLGSYYQKEDIQRKLLKAFDALTD--
SEQ ID NO:8   EEYYKLGSYYQKSDIQRKLLKAFDSLND---
SEQ ID NO:9   EEYYKLGSYYQKITDLQRTLVKAFEALD---
SEQ ID NO:10  EEYYKLGSYYQKITDLQRTLVKAFEALD---
SEQ ID NO:11  EEYYELGSYYQKITDLQRTLVKAFEALD---
SEQ ID NO:12  EEYYKLGSYYQKITDVQRSLVKAFEALD---
SEQ ID NO:13  EEYYKLGAYYQKAEVQRKLVKAFDALPE--
SEQ ID NO:14  EEYIKLGSYYQKSDHQRKLVHAFDALED---
SEQ ID NO:15  EEYYKLGSYYQLFVQTRKLLVAFDSVKDQE
```

Fig. 6

| Prenyltransferase Motif | WT residue | Activity Range | % Regiospecificity | Mutations |
|---|---|---|---|---|
| $FX^3M$ | $X^3 = S$ | 3 | 85 | $X^3 = T$ |
| $X^4FPT$ | $X^4 = F$ | 1.5 | 69 | $X^4 = L$ |
| $FFPX^5$ | $X^5 = T$ | 0.5 | 75 | $X^5 = R$ |
| $VX^6M$ | $X^6 = Q$ | 8.3-61 | 47-99.5 | $X^6$ = H, R, S, T, or Y |
| $FX^7E$ | $X^7 = S$ | 4-8 | 59-95 | $X^7$ = H, K, or R |
| $FX^8V$ | $X^8 = S$ | 6.4 | 100 | $X^8 = H$ |
| $VX^9S$ | $X^9 = I$ | 2 | 35 | $X^9 = H$ |
| $RX^{10}LV$ | $X^{10} = T$ | 3 | 62 | $X^{10} = W$ |
| $RTX^{11}V$ | $X^{11} = L$ | 2.7 | 65 | $X^{11} = Y$ |
| $GX^{12}YY$ | $X^{12} = A$ | 5 | 70 | $X^{12} = Y$ |
| $GAX^{13}Y$ | $X^{13} = Y$ | 1.4-18 | 99.4-99.8 | $X^{13}$ = A, F, L, M, P, T, V |
| $AX^{16}D$ | $X^{16} = F$ | 3 | | $X^{16} = K$ |
| $VX^6M$<br>$X^{25}R$ | $X^6 = S$<br>$X^{25} = Q$ | 18-50 | 12-100 | $X^6/X^{25}$ = A/F, F/W, F/F, F/H, G/F, H/W, H/C, H/A, H/H, H/S, H/V, H/D, H/Y, H/E, I/F, K/V, K/I, L/W, L/F, M/F, M/W, R/V, R/M, R/T |

divarinolic acid (DVA)
$C_{10}H_{12}O_4$
+
geranyl pyrophosphate (GPP)
$C_{10}H_{20}O_7P_2$
PT, $Mg^{2+}$
cannabigerovarinic acid (CBGVA)
$C_{20}H_{28}O_4$ orsellinic acid (OSA)
$C_8H_8O_4$
+
geranyl pyrophosphate (GPP)
$C_{10}H_{20}O_7P_2$
PT, $Mg^{2+}$
cannabigerorcinic acid
(CBGOA) $C_{18}H_{24}O_4$

SEQUENCE LISTING

```
<160> NUMBER OF SEQ ID NOS: 15

<210> SEQ ID NO 1
<211> LENGTH: 305
<212> TYPE: PRT
<213> ORGANISM: Streptomyces antibioticus

<400> SEQUENCE: 1

Met Ser Gly Ala Ala Asp Val Glu Arg Val Tyr Ala Ala Met Glu Glu
1               5                   10                  15

Ala Ala Gly Leu Leu Gly Val Thr Cys Ala Arg Glu Lys Ile Tyr Pro
            20                  25                  30

Leu Leu Thr Glu Phe Gln Asp Thr Leu Thr Asp Gly Val Val Val Phe
        35                  40                  45

Ser Met Ala Ser Gly Arg Arg Ser Thr Glu Leu Asp Phe Ser Ile Ser
    50                  55                  60

Val Pro Thr Ser Gln Gly Asp Pro Tyr Ala Thr Val Val Asp Lys Gly
```

```
65                  70                  75                  80

Leu Phe Pro Ala Thr Gly His Pro Val Asp Asp Leu Leu Ala Asp Thr
                85                  90                  95

Gln Lys His Leu Pro Val Ser Met Phe Ala Ile Asp Gly Glu Val Thr
            100                 105                 110

Gly Gly Phe Lys Lys Thr Tyr Ala Phe Phe Pro Thr Asp Asp Met Pro
        115                 120                 125

Gly Val Ala Gln Leu Ser Ala Ile Pro Ser Met Pro Ser Ser Val Ala
    130                 135                 140

Glu Asn Ala Glu Leu Phe Ala Arg Tyr Gly Leu Asp Lys Val Gln Met
145                 150                 155                 160

Thr Ser Met Asp Tyr Lys Lys Arg Gln Val Asn Leu Tyr Phe Ser Glu
                165                 170                 175

Leu Ser Glu Gln Thr Leu Ala Pro Glu Ser Val Leu Ala Leu Val Arg
            180                 185                 190

Glu Leu Gly Leu His Val Pro Thr Glu Leu Gly Leu Glu Phe Cys Lys
        195                 200                 205

Arg Ser Phe Ser Val Tyr Pro Thr Leu Asn Trp Asp Thr Gly Lys Ile
    210                 215                 220

Asp Arg Leu Cys Phe Ala Val Ile Ser Thr Asp Pro Thr Leu Val Pro
225                 230                 235                 240

Ser Thr Asp Glu Arg Asp Ile Glu Gln Phe Arg His Tyr Gly Thr Lys
                245                 250                 255

Ala Pro Tyr Ala Tyr Val Gly Glu Asn Arg Thr Leu Val Tyr Gly Leu
            260                 265                 270

Thr Leu Ser Pro Thr Glu Glu Tyr Tyr Lys Leu Gly Ala Tyr Tyr His
        275                 280                 285

Ile Thr Asp Ile Gln Arg Arg Leu Leu Lys Ala Phe Asp Ala Leu Glu
    290                 295                 300

Asp
305


<210> SEQ ID NO 2
<211> LENGTH: 307
<212> TYPE: PRT
<213> ORGANISM: Streptomyces Sp. Strain Cl190

<400> SEQUENCE: 2

Met Ser Glu Ala Ala Asp Val Glu Arg Val Tyr Ala Ala Met Glu Glu
1               5                   10                  15

Ala Ala Gly Leu Leu Gly Val Ala Cys Ala Arg Asp Lys Ile Tyr Pro
            20                  25                  30

Leu Leu Ser Thr Phe Gln Asp Thr Leu Val Glu Gly Gly Ser Val Val
        35                  40                  45

Val Phe Ser Met Ala Ser Gly Arg His Ser Thr Glu Leu Asp Phe Ser
    50                  55                  60

Ile Ser Val Pro Thr Ser His Gly Asp Pro Tyr Ala Thr Val Val Glu
65                  70                  75                  80

Lys Gly Leu Phe Pro Ala Thr Gly His Pro Val Asp Asp Leu Leu Ala
                85                  90                  95

Asp Thr Gln Lys His Leu Pro Val Ser Met Phe Ala Ile Asp Gly Glu
            100                 105                 110

Val Thr Gly Gly Phe Lys Lys Thr Tyr Ala Phe Phe Pro Thr Asp Asn
        115                 120                 125
```

```
Met Pro Gly Val Ala Glu Leu Ser Ala Ile Pro Ser Met Pro Pro Ala
    130                 135                 140

Val Ala Glu Asn Ala Glu Leu Phe Ala Arg Tyr Gly Leu Asp Lys Val
145                 150                 155                 160

Gln Met Thr Ser Met Asp Tyr Lys Lys Arg Gln Val Asn Leu Tyr Phe
                165                 170                 175

Ser Glu Leu Ser Ala Gln Thr Leu Glu Ala Glu Ser Val Leu Ala Leu
            180                 185                 190

Val Arg Glu Leu Gly Leu His Val Pro Asn Glu Leu Gly Leu Lys Phe
        195                 200                 205

Cys Lys Arg Ser Phe Ser Val Tyr Pro Thr Leu Asn Trp Glu Thr Gly
    210                 215                 220

Lys Ile Asp Arg Leu Cys Phe Ala Val Ile Ser Asn Asp Pro Thr Leu
225                 230                 235                 240

Val Pro Ser Ser Asp Glu Gly Asp Ile Glu Lys Phe His Asn Tyr Ala
                245                 250                 255

Thr Lys Ala Pro Tyr Ala Tyr Val Gly Glu Lys Arg Thr Leu Val Tyr
            260                 265                 270

Gly Leu Thr Leu Ser Pro Lys Glu Glu Tyr Tyr Lys Leu Gly Ala Tyr
        275                 280                 285

Tyr His Ile Thr Asp Val Gln Arg Gly Leu Leu Lys Ala Phe Asp Ser
    290                 295                 300

Leu Glu Asp
305


<210> SEQ ID NO 3
<211> LENGTH: 305
<212> TYPE: PRT
<213> ORGANISM: Actinobacteria bacterium OV320

<400> SEQUENCE: 3

Met Ser Gly Ala Ala Asp Val Glu Arg Val Tyr Ala Ala Met Glu Glu
1               5                   10                  15

Ala Ala Gly Leu Leu Asp Val Ser Cys Ala Arg Glu Lys Ile Tyr Pro
            20                  25                  30

Leu Leu Thr Val Phe Gln Asp Thr Leu Thr Asp Gly Val Val Val Phe
        35                  40                  45

Ser Met Ala Ser Gly Arg Arg Ser Thr Glu Leu Asp Phe Ser Ile Ser
    50                  55                  60

Val Pro Val Ser Gln Gly Asp Pro Tyr Ala Thr Val Val Arg Glu Gly
65                  70                  75                  80

Leu Phe Arg Ala Thr Gly Ser Pro Val Asp Glu Leu Leu Ala Asp Thr
                85                  90                  95

Val Lys His Leu Pro Val Ser Met Phe Ala Ile Asp Gly Glu Val Thr
            100                 105                 110

Gly Gly Phe Lys Lys Thr Tyr Ala Phe Phe Pro Thr Asp Asp Met Pro
        115                 120                 125

Gly Val Ala Gln Leu Thr Gly Ile Pro Ser Met Pro Ala Ser Val Ala
    130                 135                 140

Glu Asn Ala Glu Leu Phe Ala Arg Tyr Gly Leu Asp Lys Val Gln Met
145                 150                 155                 160

Thr Ser Met Asp Tyr Lys Lys Arg Gln Val Asn Leu Tyr Phe Ser Asp
                165                 170                 175

Leu Lys Gln Glu Tyr Leu Gln Pro Glu Ala Val Val Ala Leu Ala Arg
            180                 185                 190
```

```
Glu Leu Gly Leu Gln Val Pro Gly Glu Leu Gly Leu Glu Phe Cys Lys
        195                 200                 205

Arg Ser Phe Ala Val Tyr Pro Thr Leu Asn Trp Asp Thr Gly Lys Ile
    210                 215                 220

Asp Arg Leu Cys Phe Ala Ala Ile Ser Thr Asp Pro Thr Leu Val Pro
225                 230                 235                 240

Ser Thr Asp Glu Arg Asp Ile Glu Met Phe Arg Glu Tyr Ala Thr Lys
                245                 250                 255

Ala Pro Tyr Ala Tyr Val Gly Glu Lys Arg Thr Leu Val Tyr Gly Leu
            260                 265                 270

Thr Leu Ser Pro Thr Glu Glu Tyr Tyr Lys Leu Gly Ala Tyr Tyr His
        275                 280                 285

Ile Thr Asp Ile Gln Arg Gln Leu Leu Lys Ala Phe Asp Ala Leu Glu
    290                 295                 300

Asp
305


<210> SEQ ID NO 4
<211> LENGTH: 305
<212> TYPE: PRT
<213> ORGANISM: Streptomyces tendae

<400> SEQUENCE: 4

Met Ser Gly Ala Ala Asp Val Glu Arg Val Tyr Ala Ala Met Glu Glu
1               5                   10                  15

Ala Ala Gly Leu Leu Asp Val Ser Cys Ala Arg Glu Lys Ile Tyr Pro
            20                  25                  30

Leu Leu Thr Val Phe Gln Asp Thr Leu Thr Asp Gly Val Val Val Phe
        35                  40                  45

Ser Met Ala Ser Gly Arg Arg Ser Thr Glu Leu Asp Phe Ser Ile Ser
    50                  55                  60

Val Pro Val Ser Gln Gly Asp Pro Tyr Ala Thr Val Val Lys Glu Gly
65                  70                  75                  80

Leu Phe Arg Ala Thr Gly Ser Pro Val Asp Glu Leu Leu Ala Asp Thr
                85                  90                  95

Val Lys His Leu Pro Val Ser Met Phe Ala Ile Asp Gly Glu Val Thr
            100                 105                 110

Gly Gly Phe Lys Lys Thr Tyr Ala Phe Phe Pro Thr Asp Asp Met Pro
        115                 120                 125

Gly Val Ala Gln Leu Thr Glu Ile Pro Ser Met Pro Ala Ser Val Ala
    130                 135                 140

Glu Asn Ala Glu Leu Phe Ala Arg Tyr Gly Leu Asp Lys Val Gln Met
145                 150                 155                 160

Thr Ser Met Asp Tyr Lys Lys Arg Gln Val Asn Leu Tyr Phe Ser Asp
                165                 170                 175

Leu Lys Gln Glu Tyr Leu Gln Pro Glu Ala Val Val Ala Leu Ala Arg
            180                 185                 190

Glu Leu Gly Leu Gln Val Pro Gly Glu Leu Gly Leu Glu Phe Cys Lys
        195                 200                 205

Arg Ser Phe Ala Val Tyr Pro Thr Leu Asn Trp Asp Thr Gly Lys Ile
    210                 215                 220

Asp Arg Leu Cys Phe Ala Ala Ile Ser Thr Asp Pro Thr Leu Val Pro
225                 230                 235                 240

Ser Thr Asp Glu Arg Asp Ile Glu Met Phe Arg Glu Tyr Ala Thr Lys
```

```
                245                 250                 255

Ala Pro Tyr Ala Tyr Val Gly Glu Lys Arg Thr Leu Val Tyr Gly Leu
            260                 265                 270

Thr Leu Ser Ser Thr Glu Glu Tyr Tyr Lys Leu Gly Ala Tyr Tyr His
        275                 280                 285

Ile Thr Asp Ile Gln Arg Gln Leu Leu Lys Ala Phe Asp Ala Leu Glu
    290                 295                 300

Asp
305


<210> SEQ ID NO 5
<211> LENGTH: 305
<212> TYPE: PRT
<213> ORGANISM: Streptomyces sp. Root1310

<400> SEQUENCE: 5

Met Ser Gly Ala Ala Asp Val Glu Arg Val Tyr Ala Ala Met Glu Glu
1               5                   10                  15

Ala Ala Gly Leu Leu Asp Val Ser Cys Ala Arg Glu Lys Ile Tyr Pro
            20                  25                  30

Leu Leu Thr Val Phe Gln Asp Thr Leu Thr Asp Gly Val Val Val Phe
        35                  40                  45

Ser Met Ala Ser Gly Arg Arg Ser Thr Glu Leu Asp Phe Ser Ile Ser
    50                  55                  60

Val Pro Val Ser Gln Gly Asp Pro Tyr Ala Thr Val Val Lys Glu Gly
65                  70                  75                  80

Leu Phe Gln Ala Thr Gly Ser Pro Val Asp Glu Leu Leu Ala Asp Thr
                85                  90                  95

Val Ala His Leu Pro Val Ser Met Phe Ala Ile Asp Gly Glu Val Thr
            100                 105                 110

Gly Gly Phe Lys Lys Thr Tyr Ala Phe Phe Pro Thr Asp Asp Met Pro
        115                 120                 125

Gly Val Ala Gln Leu Ala Ala Ile Pro Ser Met Pro Ala Ser Val Ala
    130                 135                 140

Glu Asn Ala Glu Leu Phe Ala Arg Tyr Gly Leu Asp Lys Val Gln Met
145                 150                 155                 160

Thr Ser Met Asp Tyr Lys Lys Arg Gln Val Asn Leu Tyr Phe Ser Asp
                165                 170                 175

Leu Lys Gln Glu Tyr Leu Gln Pro Glu Ser Val Val Ala Leu Ala Arg
            180                 185                 190

Glu Leu Gly Leu Arg Val Pro Gly Glu Leu Gly Leu Glu Phe Cys Lys
        195                 200                 205

Arg Ser Phe Ala Val Tyr Pro Thr Leu Asn Trp Asp Thr Gly Lys Ile
    210                 215                 220

Asp Arg Leu Cys Phe Ala Ala Ile Ser Thr Asp Pro Thr Leu Val Pro
225                 230                 235                 240

Ser Glu Asp Glu Arg Asp Ile Glu Met Phe Arg Asn Tyr Ala Thr Lys
                245                 250                 255

Ala Pro Tyr Ala Tyr Val Gly Glu Lys Arg Thr Leu Val Tyr Gly Leu
            260                 265                 270

Thr Leu Ser Ser Thr Glu Glu Tyr Tyr Lys Leu Gly Ala Tyr Tyr His
        275                 280                 285

Ile Thr Asp Ile Gln Arg Gln Leu Leu Lys Ala Phe Asp Ala Leu Glu
    290                 295                 300
```

```
Asp
305


<210> SEQ ID NO 6
<211> LENGTH: 305
<212> TYPE: PRT
<213> ORGANISM: Streptomyces paucisporeus

<400> SEQUENCE: 6

Met Ser Gly Ala Ala Glu Val Glu Arg Val Tyr Ser Ala Met Glu Glu
1               5                   10                  15

Ala Ala Gly Leu Leu Asp Val Ala Cys Ser Pro Glu Lys Val Arg Pro
            20                  25                  30

Ile Leu Thr Ala Phe Gln Asp Val Leu Ser Asp Gly Val Ile Val Tyr
        35                  40                  45

Ser Met Ala Ser Gly Arg His Ala Thr Glu Leu Asp Phe Ser Ile Ser
    50                  55                  60

Val Pro Ala Asp His Gly Asp Pro Tyr Thr Ala Ala Leu Ala His Gly
65                  70                  75                  80

Leu Ile Pro Glu Thr Asp His Pro Val Gly Asn Leu Leu Ala Asp Thr
                85                  90                  95

Gln Lys Ala Leu Pro Val Ser Met Phe Ala Val Asp Gly Glu Val Thr
            100                 105                 110

Gly Gly Phe Lys Lys Thr Tyr Ala Phe Phe Pro Thr Asp Asp Met Pro
        115                 120                 125

Gly Leu Ala Gln Leu Ile Asp Ile Pro Ser Met Pro Pro Ser Val Ala
    130                 135                 140

Glu Asn Ala Glu Leu Phe Ala Arg Tyr Gly Leu Asp Lys Val Gln Met
145                 150                 155                 160

Thr Ser Leu Asp Tyr Lys Arg Lys Gln Val Asn Leu Tyr Phe Ser Asn
                165                 170                 175

Leu Gln Pro Glu Phe Leu Ala Pro Glu Pro Val Leu Ser Met Val Arg
            180                 185                 190

Glu Met Gly Leu Glu Leu Pro Gly Glu Lys Gly Leu Lys Phe Ala Arg
        195                 200                 205

Arg Ser Phe Ala Ile Tyr Pro Thr Leu Gly Trp Glu Ser Gly Lys Ile
    210                 215                 220

Glu Arg Leu Cys Phe Ala Val Ile Ser Thr Asp Pro Gly Leu Val Pro
225                 230                 235                 240

Ala Pro Asp Glu Ala Asp Arg Ala Leu Phe Ser Thr Tyr Ala Asn Asn
                245                 250                 255

Ala Pro Tyr Ala Tyr Ala Gly Glu Lys Arg Thr Leu Val Tyr Gly Leu
            260                 265                 270

Thr Leu Ser Pro Thr Glu Glu Tyr Tyr Lys Leu Gly Ser Tyr Tyr Gln
        275                 280                 285

Ile Thr Asp Ile Gln Arg Thr Leu Leu Lys Ala Phe Asp Ala Leu Thr
    290                 295                 300

Asp
305


<210> SEQ ID NO 7
<211> LENGTH: 305
<212> TYPE: PRT
<213> ORGANISM: Streptomyces sp. URHA0041

<400> SEQUENCE: 7
```

```
Met Ser Gly Ala Ala Glu Val Glu Arg Val Tyr Ser Ala Met Glu Glu
1               5                   10                  15

Ser Ala Gly Leu Leu Asp Val Ala Cys Ser Arg Glu Lys Ile Gln Pro
            20                  25                  30

Ile Leu Thr Ala Phe Gln Asp Val Leu Ala Asp Gly Val Ile Val Phe
        35                  40                  45

Ser Met Ala Asn Gly Arg His Ala Thr Glu Leu Asp Phe Ser Ile Ser
    50                  55                  60

Val Pro Ala Gly His Gly Asp Pro Tyr Ala Ala Ala Leu Glu His Gly
65                  70                  75                  80

Leu Ile Pro Ala Thr Gly His Pro Val Gly Asp Leu Leu Ala Asp Thr
                85                  90                  95

Gln Lys Ala Leu Pro Val Ser Met Phe Ala Val Asp Gly Glu Val Thr
            100                 105                 110

Ser Gly Phe Lys Lys Thr Tyr Ala Phe Phe Pro Thr Asp Asp Met Pro
        115                 120                 125

Gly Leu Ala Gln Leu Ile Asp Ile Pro Ser Met Pro Pro Ser Val Ala
    130                 135                 140

Glu Asn Ala Glu Leu Phe Gly Arg Tyr Gly Leu Asp Lys Val Gln Met
145                 150                 155                 160

Ile Ser Leu Asp Tyr Lys Lys Asn Gln Val Asn Leu Tyr Phe Ser Asn
                165                 170                 175

Leu Asn Pro Glu Phe Leu Gln Pro Glu Pro Val Gln Ala Met Val Arg
            180                 185                 190

Glu Met Gly Leu Gln Leu Pro Ala Asp Lys Gly Leu Ala Phe Ala Lys
        195                 200                 205

Arg Ser Phe Ala Val Tyr Pro Thr Leu Ser Trp Asp Ser Ala Lys Ile
    210                 215                 220

Glu Arg Leu Cys Phe Ala Val Ile Ser Thr Asp Pro Thr Leu Ala Pro
225                 230                 235                 240

Ala Gln Glu Gln Ala Asp Leu Asp Leu Phe Ser Thr Tyr Ala Asn Asn
                245                 250                 255

Ala Pro Tyr Ala Tyr Ala Gly Glu Lys Arg Thr Leu Val Tyr Gly Leu
            260                 265                 270

Thr Leu Ser Pro Ser Glu Glu Tyr Tyr Lys Leu Gly Ser Tyr Tyr Gln
        275                 280                 285

Ile Ser Asp Ile Gln Arg Lys Leu Leu Lys Ala Phe Asp Ala Leu Thr
    290                 295                 300

Asp
305


<210> SEQ ID NO 8
<211> LENGTH: 305
<212> TYPE: PRT
<213> ORGANISM: Streptomyces sp. CNQ-509

<400> SEQUENCE: 8

Met Ser Gly Ala Ala Asp Val Glu Arg Val Tyr Ser Ala Met Glu Glu
1               5                   10                  15

Ala Ala Arg Leu Leu Asp Ile Thr Val Ser Arg Glu Lys Val Arg Pro
            20                  25                  30

Ala Leu Glu Ala Tyr His Glu Val Leu Ala Asp Ala Val Val Val Phe
        35                  40                  45

Ser Met Ala Ser Gly Arg Tyr Ala Thr Glu Leu Asp Phe Ser Ile Ser
    50                  55                  60
```

```
Val Pro Ala Glu Ala Gly Asp Pro Tyr Arg Val Ala Leu Ala Lys Gly
65                  70                  75                  80

Leu Thr Pro Arg Thr Asp His Pro Val Gly Arg Leu Leu Ala Asp Thr
                85                  90                  95

Gln Glu His Cys Pro Val Ser Met Phe Ala Phe Asp Gly Glu Ile Thr
            100                 105                 110

Gly Gly Phe Lys Lys Thr Tyr Ala Phe Phe Pro Thr Asn Asp Leu Gln
        115                 120                 125

Ser Ala Ser Lys Leu Ala Glu Ile Pro Ser Met Pro Asp Ser Val Lys
    130                 135                 140

Glu Asn Ala Asp Leu Phe Ala Arg Tyr Gly Leu Asp Lys Val Gln Met
145                 150                 155                 160

Thr Ser Ile Asp Tyr Lys Lys Lys Ala Val Asn Leu Tyr Phe Ser Glu
                165                 170                 175

Met Ser Pro Asp Ile Leu Gly Pro Asp Thr Val Arg Ser Met Leu Arg
            180                 185                 190

Asp Met Gly Leu Lys Glu Thr Gly Glu Thr Gly Leu Thr Phe Ala Arg
        195                 200                 205

Arg Ser Phe Ser Val Tyr Pro Thr Leu Asn Trp Glu Thr Gly Arg Ile
    210                 215                 220

Glu Arg Leu Cys Phe Ala Val Ile Ser Arg Asp Pro Thr Leu Ala Pro
225                 230                 235                 240

Ala Glu Arg Ala Glu Asp Leu Ala Lys Phe Ser Lys Tyr Ala Asn Asn
                245                 250                 255

Ala Pro Tyr Ala Tyr Ala Gly Glu Ala Arg Thr Leu Val Tyr Gly Leu
            260                 265                 270

Thr Leu Thr Pro Arg Glu Glu Tyr Tyr Lys Leu Gly Ser Tyr Tyr Gln
        275                 280                 285

Ile Ser Asp Ile Gln Arg Lys Leu Leu Lys Ala Phe Asp Ser Leu Asn
    290                 295                 300

Asp
305
```

<210> SEQ ID NO 9
<211> LENGTH: 304
<212> TYPE: PRT
<213> ORGANISM: Streptomyces

<400> SEQUENCE: 9

```
Met Ser Gly Ala Lys Asp Val Glu Arg Val Tyr Ser Ala Met Glu Glu
1               5                   10                  15

Ala Ala Gly Leu Leu Asn Val Pro Val Ala Arg Asp Lys Ile Trp Pro
            20                  25                  30

Val Leu Thr Ala Tyr Gln Asp Ala Leu Ala Asp Ala Val Ile Val Phe
        35                  40                  45

Ser Met Ala Gly Gly Arg Arg Ser Thr Glu Leu Asp Phe Ser Ile Ser
    50                  55                  60

Val Pro Thr Asp His Gly Asp Pro Phe Thr Thr Ala Leu Glu Arg Gly
65                  70                  75                  80

Leu Thr Glu Lys Glu Asn His Pro Val Asp Asn Leu Leu Ala Glu Leu
                85                  90                  95

Arg Asp Gly Phe Pro Leu Gly Met Tyr Ala Ile Asp Gly Met Val Thr
            100                 105                 110

Thr Gly Phe Lys Lys Ala Tyr Ala Ser Phe Pro Thr Asn Glu Pro Gln
```

```
        115                 120                 125

Pro Leu Thr Ala Leu Leu Asp Leu Pro Ser Met Pro Glu Ser Ala Arg
    130                 135                 140

Ala Asn Ala Glu Leu Phe Ala Arg Tyr Gly Leu Asp Lys Val Gln Met
145                 150                 155                 160

Val Ser Val Asp Tyr Pro Lys Arg Gln Val Asn Leu Tyr Phe Ser Glu
                165                 170                 175

Leu Lys Ala Asp His Leu Thr Pro Glu Gln Val Lys Ala Thr Ala Ser
            180                 185                 190

Glu Met Gly Leu Val Glu Pro Thr Asp Met Ala Leu Asp Phe Ala Thr
        195                 200                 205

Gly Ser Phe Ala Val Tyr Pro Thr Leu Gly Tyr Asp Ser Asp Val Val
    210                 215                 220

Asp Arg Ile Thr Tyr Ala Val Ile Ser Val Asp Pro Thr Leu Ala Pro
225                 230                 235                 240

Thr Thr Ser Glu Pro Glu Lys Thr Gln Ile Thr Thr Tyr Ala Asn Ser
                245                 250                 255

Ala Pro Tyr Ala Tyr Ala Gly Glu Asn Arg Thr Leu Val Tyr Gly Phe
            260                 265                 270

Thr Leu Thr Ser Lys Glu Glu Tyr Tyr Lys Leu Gly Ser Tyr Tyr Gln
        275                 280                 285

Ile Thr Asp Leu Gln Arg Thr Leu Val Lys Ala Phe Glu Ala Leu Asp
    290                 295                 300


<210> SEQ ID NO 10
<211> LENGTH: 304
<212> TYPE: PRT
<213> ORGANISM: Streptomyces sp. CNH099

<400> SEQUENCE: 10

Met Ser Gly Ala Lys Asp Val Glu Arg Val Tyr Ser Ala Met Glu Glu
1               5                   10                  15

Ala Ala Gly Leu Leu Asn Val Pro Val Ala Arg Asp Lys Ile Trp Pro
            20                  25                  30

Val Leu Thr Ala Tyr Gln Asp Ala Leu Ala Asp Ala Val Ile Val Phe
        35                  40                  45

Ser Met Ala Gly Gly Arg Arg Ser Thr Glu Leu Asp Phe Ser Ile Ser
    50                  55                  60

Val Pro Thr Asp His Gly Asp Pro Phe Thr Thr Ala Leu Glu Arg Gly
65                  70                  75                  80

Leu Thr Glu Lys Glu Asn His Pro Val Asp Asn Leu Leu Ala Glu Leu
                85                  90                  95

Arg Asp Gly Phe Pro Leu Gly Met Tyr Ala Ile Asp Gly Met Val Thr
            100                 105                 110

Thr Gly Phe Lys Lys Ala Tyr Ala Ser Phe Pro Thr Asn Glu Pro Gln
        115                 120                 125

Pro Leu Thr Ala Leu Leu Asp Leu Pro Ser Met Pro Glu Ser Ala Arg
    130                 135                 140

Ala Asn Ala Glu Leu Phe Ala Arg Tyr Gly Leu Asp Lys Val Gln Met
145                 150                 155                 160

Val Ser Val Asp Tyr Pro Lys Arg Gln Val Asn Leu Tyr Phe Ser Asp
                165                 170                 175

Leu Asn Ala Asp His Leu Thr Pro Glu Glu Val Lys Ser Thr Ala Ser
            180                 185                 190
```

```
Glu Met Gly Leu Val Glu Pro Thr Asp Met Ala Leu Asp Phe Ala Thr
        195                 200                 205

Gly Ser Phe Ala Val Tyr Pro Thr Leu Gly Tyr Asp Ser Asp Val Val
    210                 215                 220

Asp Arg Ile Thr Tyr Ala Val Ile Ser Val Asp Pro Thr Leu Ala Pro
225                 230                 235                 240

Thr Thr Ser Glu Pro Glu Lys Thr Gln Ile Thr Thr Tyr Ala Asn Ser
                245                 250                 255

Ala Pro Tyr Ala Tyr Ala Gly Glu Asn Arg Thr Leu Val Tyr Gly Phe
            260                 265                 270

Thr Leu Thr Ser Lys Glu Glu Tyr Tyr Lys Leu Gly Ser Tyr Tyr Gln
        275                 280                 285

Ile Thr Asp Leu Gln Arg Thr Leu Val Lys Ala Phe Glu Ala Leu Asp
    290                 295                 300


<210> SEQ ID NO 11
<211> LENGTH: 304
<212> TYPE: PRT
<213> ORGANISM: Streptomyces

<400> SEQUENCE: 11

Met Ser Gly Ala Asn Asp Val Glu Arg Val Tyr Ser Ala Met Glu Glu
1               5                   10                  15

Ala Ala Gly Leu Leu Asn Val Pro Val Ala Arg Asp Lys Ile Trp Pro
            20                  25                  30

Val Leu Thr Ala Tyr Gln Asp Ala Leu Ala Asp Ala Val Val Val Phe
        35                  40                  45

Ser Met Ala Gly Gly Arg Arg Ala Thr Glu Leu Asp Phe Ser Ile Ser
    50                  55                  60

Val Pro Thr Asp Leu Gly Asp Pro Phe Thr Thr Ala Leu Arg Arg Gly
65                  70                  75                  80

Leu Thr Glu Lys Thr Asn His Pro Val Asp Asn Leu Leu Ala Glu Leu
                85                  90                  95

Thr Asp Gly Phe Glu Ile Gly Met Tyr Ala Ile Asp Gly Met Val Thr
            100                 105                 110

Thr Gly Phe Lys Lys Thr Tyr Ala Ser Phe Pro Thr Asn Glu Pro Gln
        115                 120                 125

Pro Leu Thr Ala Leu Leu Asp Val Pro Ser Met Pro Glu Ser Ala Arg
    130                 135                 140

Ala Asn Ala Glu Leu Phe Ala Arg Tyr Gly Leu Asp Lys Val Gln Met
145                 150                 155                 160

Val Ser Val Asp Tyr Pro Lys Arg Gln Val Asn Leu Tyr Phe Ser Glu
                165                 170                 175

Leu Asp Thr Asp Tyr Leu Gln Pro Glu His Val Lys Ser Leu Ala Arg
            180                 185                 190

Glu Thr Gly Leu Val Glu Pro Thr Glu Met Gly Leu Asp Phe Ala Ser
        195                 200                 205

Gly Ser Phe Ala Val Tyr Pro Thr Leu Gly Tyr Asp Asn Asp Ile Val
    210                 215                 220

Asp Arg Ile Thr Tyr Ala Val Ile Ser Val Asp Pro Thr Leu Ala Pro
225                 230                 235                 240

Thr Lys Ser Glu Pro Glu Val Ser Gln Leu Ser Arg Tyr Ala Thr Ser
                245                 250                 255

Ala Pro Tyr Ala Tyr Ala Gly Glu Asn Arg Thr Leu Val Tyr Gly Val
            260                 265                 270
```

```
Thr Leu Thr Ser Lys Glu Glu Tyr Tyr Lys Leu Gly Ser Tyr Tyr Gln
        275                 280                 285

Ile Thr Asp Leu Gln Arg Thr Leu Val Lys Ala Phe Glu Ala Leu Asp
    290                 295                 300


<210> SEQ ID NO 12
<211> LENGTH: 304
<212> TYPE: PRT
<213> ORGANISM: Streptomyces

<400> SEQUENCE: 12

Met Ser Gly Ala Asn Asp Val Glu Arg Val Tyr Ser Ala Met Glu Glu
1               5                   10                  15

Ala Ala Gly Leu Leu Gly Val Pro Val Ala Arg Glu Lys Val Arg Pro
            20                  25                  30

Val Leu Thr Ala Tyr Gln Asp Ala Leu Ala Asp Ala Val Val Val Phe
        35                  40                  45

Ser Met Ala Gly Gly Arg Arg Ala Thr Glu Leu Asp Phe Ser Ile Ser
    50                  55                  60

Val Pro Thr Asp His Gly Asp Pro Phe Thr Thr Ala Leu Gln Arg Gly
65                  70                  75                  80

Leu Thr Glu Lys Thr Gly His Pro Val Asp Asn Leu Leu Ala Glu Leu
                85                  90                  95

Arg Glu Gly Phe Pro Leu Gly Met Tyr Ala Ile Asp Gly Met Val Ser
            100                 105                 110

Thr Gly Phe Lys Lys Thr Tyr Ala Ser Phe Pro Thr Asn Glu Pro Gln
        115                 120                 125

Pro Leu Asp Asp Leu Leu Asp Val Pro Ser Met Pro Ala Ser Ala Arg
    130                 135                 140

Ala Asn Ala Lys Leu Phe Ala Asn Tyr Gly Leu Asp Lys Val Gln Met
145                 150                 155                 160

Val Ser Val Asp Tyr Pro Lys Arg Gln Val Asn Leu Tyr Phe Ser Glu
                165                 170                 175

Leu Asn Thr Asp Tyr Leu Gln Pro Ala Gln Val Lys Ala Leu Ala Ala
            180                 185                 190

Glu Met Gly Leu Ile Glu Pro Ser Glu Leu Gly Leu Glu Phe Ala Lys
        195                 200                 205

Gly Ser Phe Ala Val Tyr Pro Thr Leu Ser Tyr Asp Thr Asp Ala Ser
    210                 215                 220

Asp Arg Leu Cys Leu Ala Val Ile Ser Ser Asp Pro Thr Leu Ala Pro
225                 230                 235                 240

Thr Thr Ser Glu Pro Glu Val Thr Gln Phe Ser Thr Tyr Ala Asn Asn
                245                 250                 255

Ala Pro Tyr Ala Tyr Ala Gly Glu Asn Arg Thr Leu Val Tyr Gly Leu
            260                 265                 270

Thr Leu Thr Pro Lys Glu Glu Tyr Tyr Lys Leu Gly Ser Tyr Tyr Gln
        275                 280                 285

Ile Thr Asp Tyr Gln Arg Lys Leu Val Lys Ala Phe Glu Ala Leu Asp
    290                 295                 300


<210> SEQ ID NO 13
<211> LENGTH: 306
<212> TYPE: PRT
<213> ORGANISM: Streptomyces sp. 303MFCol5.2

<400> SEQUENCE: 13
```

```
Met Ser Lys Ala Thr Glu Val Asp Arg Val Tyr Ala Ala Val Glu Lys
1               5                   10                  15

Ala Ala Ala Leu Ala Gly Thr Thr Cys Ala Gly Asp Lys Val Arg Pro
            20                  25                  30

Val Leu Thr Gly His Gln Asp Leu Leu Asp Glu Ala Val Ile Val Phe
        35                  40                  45

Ser Met Thr Ala Ser Gly Ser His Ser Gly Gly Leu Asp Leu Ser Met
    50                  55                  60

Thr Val Pro Ala Glu His Val Asp Pro Tyr Ser Phe Ala Leu Ser Glu
65                  70                  75                  80

Gly Leu Ile Glu Pro Thr Asp His Pro Val Gly Ser Val Ile Ser Asp
                85                  90                  95

Phe Gln Glu Arg Phe Pro Ile Gly Met Tyr Gly Ile Asp Val Asp Val
            100                 105                 110

Ala Gly Gly Phe Lys Lys Ala Tyr Ala Ala Phe Pro Ser Asn Asp Leu
        115                 120                 125

Arg Glu Leu Lys Gln Leu Phe Asp Leu Pro Ser Met Pro Ser Ala Ala
    130                 135                 140

Ala Glu Asn Ala Glu Leu Phe Ala Arg Tyr Gly Leu Asp Arg Val Thr
145                 150                 155                 160

Gly Val Ser Val Asp Tyr Lys Arg His Glu Leu Asn Leu Tyr Cys Asp
                165                 170                 175

Arg Ala Thr Thr Glu Pro Leu Asp Pro Asp Tyr Val Gln Ser Met Leu
            180                 185                 190

Arg Asp Met Gly Leu Lys Glu Ala Ser Glu Gln Gly Leu Glu Phe Ala
        195                 200                 205

Lys Lys Thr Phe Ala Ile Tyr Pro Thr Leu Asn Trp Asp Ser Ser Glu
    210                 215                 220

Ile Val Arg Ile Cys Phe Ala Val Ile Thr Thr Asp Pro Ala Thr Thr
225                 230                 235                 240

Pro Thr Arg Ser Glu Pro Glu Leu Gly Gln Met Trp Glu Tyr Ala Asn
                245                 250                 255

Thr Ala Pro Tyr Ala Tyr Val Gly Glu Gln Arg Ala Leu Val Tyr Gly
            260                 265                 270

Leu Ala Leu Ser Pro Glu Lys Glu Tyr Tyr Lys Leu Gly Ala Tyr Tyr
        275                 280                 285

Gln Ile Ser Asp Tyr Gln Arg Lys Leu Val Lys Ala Phe Asp Ala Leu
    290                 295                 300

Pro Glu
305
```

<210> SEQ ID NO 14
<211> LENGTH: 378
<212> TYPE: PRT
<213> ORGANISM: Streptomyces niveus

<400> SEQUENCE: 14

```
Met Cys Val Pro Gly Ser Arg Ala Arg Arg Pro Gly Ser Arg Gly Trp
1               5                   10                  15

Leu Glu Arg Thr Ala Lys Pro Ala Pro Thr Arg Gly Thr Val Gly Ala
            20                  25                  30

Lys Val Arg Ser Gln Thr Trp Glu Arg Arg Ala Pro Gly Ala Thr Thr
        35                  40                  45

Val Thr Cys Pro Val Gln Gly Arg Ser Thr Gly Pro Ile Gln Ala Asp
```

```
    50                  55                  60

Ile Gln Asp Arg His Val Gly Asp Ser Met Ser Gly Ala Ala Asp Val
65                  70                  75                  80

Glu Arg Val Tyr Ser Ala Met Glu Arg Ala Ala Gly Leu Leu Asp Leu
                85                  90                  95

Thr Cys Ala Arg Glu Lys Ile Leu Pro Ile Leu Thr Ala Tyr Lys Glu
            100                 105                 110

Ala Leu Ala Asp Ser Val Ile Val Phe Ser Met Ser Gly Gly Asp His
        115                 120                 125

Ser Ala Glu Leu Asp Phe Ser Phe Thr Ile Pro Ser Gly Asp Val Asp
    130                 135                 140

Pro Tyr Ala Phe Gly Pro Ser Thr Gly Ile Pro Thr Glu Thr Asp His
145                 150                 155                 160

Pro Ile Ala Ser Leu Leu Ser Asp Thr Gly Glu Arg Cys Pro Val Ala
                165                 170                 175

Met Tyr Gly Val Asp Gly Glu Val Ser Gly Gly Phe Lys Lys Thr Tyr
            180                 185                 190

Ala Ala Phe Pro Ile Asn Asp Leu Leu Asp Leu Ser Lys Leu Val Ala
        195                 200                 205

Val Pro Ser Met Pro Pro Ala Val Ala Glu Asn Ala Glu Leu Phe Ala
    210                 215                 220

Arg Tyr Gly Leu Asp Lys Val Gln Gly Ile Ser Ile Asp Tyr Gln Arg
225                 230                 235                 240

Lys Gln Val Asn Leu Tyr Cys Gly Asp Ile Pro Ala Glu Ser Leu Glu
                245                 250                 255

Pro Glu Thr Val Arg Ser Met Leu Arg Glu Met Gly Leu Arg Glu Pro
            260                 265                 270

Ser Glu Glu Gly Leu Glu Phe Val Arg Lys Ser Phe Ala Val Tyr Pro
        275                 280                 285

Thr Leu Ser Trp Asp Ser Ser Arg Ile Glu Arg Ile Cys Phe Ala Val
    290                 295                 300

Ile Ser Thr Asp Pro Thr Leu Ala Pro Thr Arg Val Glu Ser Asp Val
305                 310                 315                 320

Ala Leu Phe Ser Lys Tyr Ala Asn Asn Ala Pro Tyr Ala Tyr Ala Gly
                325                 330                 335

Glu Arg Arg Thr Leu Ile Tyr Gly Leu Ala Val Ser Pro Thr Lys Glu
            340                 345                 350

Tyr Ile Lys Leu Gly Ser Tyr Tyr Gln Ile Ser Asp His Gln Arg Lys
        355                 360                 365

Leu Val Lys Ala Phe Asp Ala Leu Glu Asp
    370                 375


<210> SEQ ID NO 15
<211> LENGTH: 311
<212> TYPE: PRT
<213> ORGANISM: Streptomyces sp. CNH287

<400> SEQUENCE: 15

Met Tyr Gly Gly Thr Glu Val Glu Glu Val Tyr Ser Ala Leu Glu Lys
1               5                   10                  15

Ser Ala Gly Leu Val Gly Val Pro Cys Asn Arg Asp Lys Val Trp Pro
            20                  25                  30

Ala Leu Ser Thr Tyr Gln Asp Ala Leu Gly Glu Ala Val Ile Val Phe
        35                  40                  45
```

-continued

```
Ser Val Ala Thr Asp Glu Arg His Ala Gly Glu Leu Asp Tyr Thr Ile
    50                  55                  60

Thr Val Pro Thr Gly Gly Ala Asp Pro Tyr Ala Leu Ala Leu Ala Lys
65                  70                  75                  80

Gly Leu Thr Pro Glu Thr Asp His Pro Val Gly Thr Leu Leu Ala Gly
                85                  90                  95

Val Gln Glu Arg Cys Pro Val Ala Gly Tyr Ala Val Asp Cys Gly Val
            100                 105                 110

Val Gly Gly Phe Lys Lys Ile Tyr Ser Phe Phe Pro Gln Asp Asp Leu
        115                 120                 125

Gln Gly Leu Ala Lys Leu Ala Glu Ile Pro Ser Met Pro Arg Ala Leu
    130                 135                 140

Ala Glu Asn Ala Ala Leu Phe Ala Arg His Gly Leu Asp His Lys Val
145                 150                 155                 160

Thr Met Leu Gly Ile Asp Tyr Gln Arg Glu Ser Val Asn Leu Tyr Phe
                165                 170                 175

Gly Lys Leu Pro Glu Glu Cys Leu Gln Pro Asp Ser Ile Arg Ala Ile
            180                 185                 190

Leu Arg Asp Ile Gly Leu Pro Glu Pro Thr Glu Pro Met Leu Glu Phe
        195                 200                 205

Ala Arg Lys Ser Phe Ala Ile Tyr Val Thr Leu Ser Trp Asp Ala Ala
    210                 215                 220

Lys Val Glu Arg Ile Cys Phe Ala Val Pro Pro Gly Arg Asp Leu Ile
225                 230                 235                 240

Thr Leu Asp Pro Ser Ala Leu Pro Ala Arg Ile Ala Pro Glu Ile Glu
                245                 250                 255

His Phe Ala Arg Asn Ser Pro Tyr Ala Tyr Pro Gly Asp Arg Met Leu
            260                 265                 270

Val Tyr Gly Val Thr Trp Ser Pro Glu Glu Glu Tyr Tyr Lys Leu Gly
        275                 280                 285

Ser Tyr Tyr Gln Leu Pro Val Gln Thr Arg Lys Leu Leu Val Ala Phe
    290                 295                 300

Asp Ser Val Lys Asp Gln Glu
305                 310
```

PRENYLTRANSFERASE VARIANTS AND METHODS FOR PRODUCTION OF PRENYLATED AROMATIC COMPOUNDS

PRIORITY CLAIM

This application claims priority to International Application No. PCT/EP2019/021448, filed Mar. 8, 2019, which claims the benefit of U.S. Provisional Patent Application Ser. No. 62/640,384 filed Mar. 8, 2018 entitled PRENYLTRANSFERASE VARIANTS AND METHODS FOR PRODUCTION OF PRENYLATED AROMATIC COMPOUNDS, wherein the contents of said applications are incorporated herein by reference in their entireties. Also, the entire contents of the ASCII text file entitled "GNO0093US_Sequence_Listing_V2.txt" created on Dec. 22, 2020, having a size of 41 kilobytes is incorporated herein by reference.

BACKGROUND

Cannabinoids constitute a varied class of chemicals that bind to cellular cannabinoid receptors. Modulation of these receptors has been associated with different types of physiological processes including pain-sensation, memory, mood, and appetite. Endocannabinoids, which occur in the body, phytocannabinoids, which are found in plants such as *cannabis*, and synthetic cannabinoids, can have activity on cannabinoid receptors and elicit biological responses.

*Cannabis sativa* produces a variety of phytocannabinoids, the most notable of which is a precursor of tetrahydrocannabinol (THC), the primary psychoactive compound in *cannabis*. However, *C. sativa* also produces precursors of other cannabinoids such as cannabidiol (CBD), cannabigerol (CBG), and cannabichromene (CBC). CBD, CBG, and CBC, which, unlike THC, are not psychoactive. In *C. sativa*, precursors of CBD, CBG, CBC, and THC, are carboxylic acid-containing molecules referred to as $\Delta^9$-tetrahydrocannabinoic acid ($\Delta^9$-THCA), CBDA, cannabigerolic acid (CBGA), and cannabichromenic acid (CBCA), respectively. $\Delta^9$-THCA, CBDA, CBGA, and CBCA are bioactive after decarboxylation, such as caused by heating, to their bioactive forms, e.g. CBGA to CBG.

Despite the well-known actions of THC, the non-psychoactive CBD, CBG, and CBC cannabinoids also have important therapeutic uses. For example, these cannabinoids can be used for the treatment of conditions and diseases that are altered or improved by action on the $CB_1$ and/or $CB_2$ cannabinoid receptors, and/or $\alpha_2$-adrenergic receptor. CBG has been proposed for the treatment of glaucoma as it has been shown to relieve intraocular pressure. CBG can also be used to treat inflammatory bowel disease. Further, CBG can also inhibit the uptake of GABA in the brain, which can decrease anxiety and muscle tension. Cellular synthesis of CBG, via CBGA, derives from olivetolic acid and geranyldiphosphate pathways. Formation of olivetolic acid stems from fatty acid biosynthesis in which hexanoic acid is produced and which in turn is converted to hexanoyl-CoA through hexanoyl CoA synthetase. Polyketide synthase catalyzes three sequential condensation reactions of malonyl-CoA onto hexanoyl-CoA to form 3,5,7-trioxododecanoyl-CoA which is converted to olivetolic acid (2,4-dihydroxy-6-pentylbenzoate) by the enzyme olivetolic acid cyclase (Gagne et al., PNAS, 109: 12811-12816). Formation of geranyldiphosphate stems from the mevalonate pathway (MVA) or methylerythritol-4-phosphate pathway (MEP; also known as the deoxyxylulose-5-phosphate), which produce isopentyl pyrophosphate (IPP) and dimethylallyl pyrophosphate (DMAPP), which are converted to geranyl pyrophosphate (GPP) using geranyl pyrophosphate synthase.

Geranyl-pyrophosphate-olivetolic acid geranyltransferase (EC 2.5.1.102, GOT) catalyzes the following reaction:

geranyl diphosphate+2,4-dihydroxy-6-pentylbenzoate→diphosphate+cannabigerolic acid The enzyme carrying out the above reaction in *C. sativa* is a transmembrane prenyltransferase belonging to the UbiA superfamily of membrane proteins. See for example WO2011017798A1 describing CsPT1. However, the above reaction has also been reported to be carried out by a different family of enzymes. In particular, aromatic prenyltransferases that are soluble, non-transmembrane, and have a 10-stranded antiparallel β-barrel consisting of 5 repeated αββα motifs, can catalyze the transfer of isoprenoid chains to aromatic rings. For example, Yang, Y., et al. (Biochemistry 51:2606-180, 2012) reports that NphB, a *Streptomyces*-derived, soluble enzyme, catalyzes the attachment of a 10-carbon geranyl group to aromatic substrates; originally identified in the biosynthetic pathway of the antioxidant naphterpin. Yang notes the reaction mechanism of the prenylation step has been characterized as a S(N)1 type dissociative mechanism with a weakly stable carbocation intermediate. NphB catalyzes the prenyl transfer between GPP and 1,6 dihydroxynaphthalene (1,6-DHN) and yields three products with the geranyl moiety attaching to different carbon atoms of 1,6-DHN. The major product 5 geranyl DHN and minor product 2-geranyl DHN were characterized with a product ratio of 10:1.

A subsequent publication (Kumano et al 2008 Bioorg. Med. Chem, 16, 8117-8126 (2008)), reports rates and regioselectivity measurements for NphB-catalyzed geranylation of olivetol, with mixed regioselectivity at 2- and 4-OL ring positions, and rates of 0.0026 mol 2-geranyl-OL/min/mol NphB and 0.0016 mol 4-geranyl-OL/min/mol NphB, which are extremely slow.

SUMMARY

Aspects of the disclosure are directed towards forming prenylated aromatic compounds, including cannabinoids, engineered enzymes (e.g., prenyltransferase variants of the soluble aromatic prenyltransferase type) with improved activity that facilitate cannabinoid formation, non-natural cells including the engineered enzymes and prenylated aromatic compound formation, including cannabinoid pathways, fermentation methods using the same, and improved prenylated aromatic compound preparations, including cannabinoid product preparations. In particular, disclosure associated with the current invention is directed towards non-natural prenyltransferases that include at least one amino acid variation that differs from an amino acid residue of a wild type soluble type prenyltransferase.

In experimental studies associated with the invention, prenyltransferase homologs and non-natural prenyltransferase variants were identified that demonstrated activity on, or improved activity on catalyzing the reaction between olivetolic acid (OLA) and geranyl diphosphate (GPP) to form the product 3-geranyl-olivetolate (cannabigerolic acid; CBGA, 3-GOLA). Described herein are a soluble prenyltransferase of SEQ ID NO: 1 and variants thereof with improved activity and/or regioselectivity. Also described herein are homologs of SEQ ID NO:1 and variants thereof, including NphB and non-natural prenyltransferase variants of those of prenyltransferase homologs with improved activity and/or regioselectivity.

Unique non-natural prenyltransferase variants were identified with improved activities and/or which demonstrated regioselectivity to 3-geranyl-olivetolate, (3-GOLA), forming a predominance of the desired product 3-GOLA, i.e. CBGA, over the less preferred 5-geranyl-olivetolate (5-GOLA). In aspects, the inventive findings of prenyltransferase variants with improved activities and/or regioselectivity to 3-GOLA provide important disclosure as undesired 5-GOLA is the more dominant product in reactions catalyzed by wild-type homologs of NphB. As such, it is preferred to avoid enzyme catalyzed reactions that lead to 5-GOLA when the desired target product is cannabigerolic acid (CBGA). Therefore the disclosure provides the surprising discovery of a significant number of prenyltransferase variants that have very high regio specificity towards CBGA (3-GOLA). Accordingly, these high-activity and regiospecific enzymes can be used according to the current disclosure to catalyze formation of CBGA (3-GOLA) in engineered cells to generate high titers of this molecule which in turn can be used for generating therapeutic and medicinal preparations, including cannabinoids, especially CBGA and its derivatives.

Non-natural prenyltransferase variants that demonstrated activity on, or improved activity catalyzing the reaction between divarinolic acid (DVA) and geranyl diphosphate (GPP) to form the product cannabigerovarinic acid (CBGVA), as well as those that catalyzing the reaction between orsellinic acid (OSA) and geranyl diphosphate (GPP) to form the product cannabigerorcinic acid (CBGOA), were identified. Non-natural prenyltransferase variants that demonstrated regioselectivity to 3-geranyl-divarinolic acid (3-GDVA), and to 3-geranyl-orsellinate (3-GOSA) were also identified.

In embodiments, the current invention provides non-natural prenyltransferases that include at least one amino acid variation as compared to a wild type prenyltransferase. Non-natural prenyltransferases of the disclosure include those that are (a) enzymatically capable of at least two fold greater rate of formation of geranyl-olivetolate from geranyl pyrophosphate and olivetolic acid, as compared to the wild type prenyltransferase or; (b) regioselective to 3-geranyl-olivetolate (3-GOLA); or both (a) and (b).

In embodiments, the current invention also provides non-natural prenyltransferases that include at least one amino acid variation as compared to a wild type prenyltransferase that are enzymatically capable of (a1) at least two fold greater rate of formation of cannabigerovarinic acid (CBGVA) from geranyl pyrophosphate and divarinolic acid (DVA), as compared to the wild type prenyltransferase; (a2) 50% or greater regioselectivity to 3-geranyl-divarinolic acid (3-GDVA), or both (a1) and (a2); or (b1) at least two fold greater rate of formation of cannabigerorcinic acid (CBGOA) from geranyl pyrophosphate and orsellinic acid (OSA), as compared to the wild type prenyltransferase; (b2) 50% or greater regioselectivity to 3-geranyl-orsellinate (3-GOSA); or both (b1) and (b2).

In embodiments, the invention also provides a non-natural prenyltransferase comprising at least one amino acid variation as compared to a wild type prenyltransferase, and enzymatically capable of regioselectively forming a 2-prenylated 5-alkylbenzene-1,3-diol from geranyl pyrophosphate and 5-alkylbenzene-1,3-diol. For example, the 5-alkylbenzene-1,3-diol substrate can be olivetol and the 2-prenylated 5-alkylbenzene-1,3-diol can be cannabigerol (CBG; 2-GOL).

The variant prenyltransferases of the disclosure have at least one amino acid substitution as compared to its corresponding natural prenyltransferases of the soluble, αββα (ABBA) structural type, or a prenyltransferases having one or more variations that are different than one or more variations that provide improved activity and/or regioselectivity to 3-GOLA. For example, a prenyltransferase with a different mutation which may have been previously engineered can be used as a template, prior to incorporating any modification described herein. Such prenyltransferases that are starting sequences for incorporating a modification described herein to generate the novel engineered enzyme may be alternatively referred to herein as wild-type, template, starting sequence, natural, naturally-occurring, unmodified, corresponding natural prenyltransferases, corresponding natural prenyltransferases without the amino acid substitution, corresponding prenyltransferases or corresponding prenyltransferases without the amino acid substitution(s). Experimental studies described demonstrate that a number of amino acid positions along the length of the prenyltransferase sequence can be substituted to provide non-natural prenyltransferases having increased activity and desired regioselectivity. Experimental studies associated with the disclosure show single substitutions and combinations of substitutions in a prenyltransferase template can provide increased activity and desired regioselectivity, and therefore provide single and combination variants of a starting or template or corresponding prenyltransferases, e.g., in particular enzymes of the class EC 2.5.1.102, having increased substrate conversion and/or regioselectivity.

Amino acid variations can include those relative to SEQ ID NO:1, or a homolog thereof, having one or more variations at position(s) selected from the group consisting of: S49T, F121L, T124R, Q159H, Q159R, Q159S, Q159T, Q159Y, Q159A, Q159F, Q159G, Q159I, Q159K, Q159L, Q159M, Q159A, S175H, S175K, S175R, S212H, I232H, T267W, L268Y, A285Y, Y286A, Y286F, Y286L, Y286M, Y286P, Y286I, Y286T, Y286V, Q293F, Q293W, Q293H, Q293C, Q293A, Q293S, Q293V, Q293D, Q293Y, Q293E, Q293I, Q293M, Q293T, and F300K. Amino acid variations can include those relative to SEQ ID NO:2, or a homolog thereof, having one or more variations at position(s) selected from the group consisting of: S51T, F123L, T126R, Q161H, Q161R, Q161S, Q161T, Q161Y, Q161A, Q161F, Q161G, Q161I, Q161K, Q161L, Q161M, Q161A, S177H, S177K, S177R, S214H, I234H, T269W, L270Y, A287Y, Y288A, Y288F, Y288L, Y288M, Y288P, Y288T, Y288V, Q295F, Q295W, Q295H, Q295C, Q295A, Q295S, Q295V, Q295D, Q295Y, Q295E, Q295I, Q295M, Q295T, and F303K.

Using the information about variant locations and identities that provided improved activity and/or regioselectivity, and sequence alignment information of various prenyltransferase homologs, prenyltransferase amino acid motifs were identified that include the variant positions. Accordingly, the disclosure provides non-natural prenyltransferases with regards to motif sequence and amino acid variant therein, wherein a non-natural prenyltransferase having 50% or greater identity to any one of SEQ ID NOs:1-15 and having one or more of amino acid motifs (a)-(j) as follows: (a) $FX^3M$ (SEQ ID NO:16) or $VFX^3MA$ (SEQ ID NO:17) wherein; $X^3$ is T; (b) $X^4FPX^5$ (SEQ ID NO:18), wherein $X^4$ is F or L, and wherein $X^5$ is T or R, with the proviso that in a single motif, $X^4$ is not F, and $X^5$ is not T; (c) $VX^6M$ (SEQ ID NO:19) or $KVX^6MT$ (SEQ ID NO:20) wherein $X^6$ is selected from the group consisting of H, R, S, T, Y, A, F, G, I, K, L, M, and A; (d) $FX^7E$ (SEQ ID NO:21) or $YFX^7EL$ (SEQ ID NO:22) wherein $X^7$ is selected from the group consisting of H, K, and R;

(e) $FX^8V$ (SEQ ID NO:23) or $SFX^8VY$ (SEQ ID NO:24) wherein $X^8$ is H; (f) $VX^9S$ (SEQ ID NO:25) or $AVX^9SN$ (SEQ ID NO:26) wherein $X^9$ is H; (g) $RX^{10}X^{11}V$ (SEQ ID NO:27), wherein, $X^{10}$ is T or W, and wherein $X^{11}$ is L or Y; with the proviso that in a single motif, $X^{10}$ is not T and $X^{11}$ is not L; (h) $GX^{12}X^{13}Y$ (SEQ ID NO:28), wherein, $X^{12}$ is A or Y, and wherein $X^{13}$ is Y, A, F, L, M, P, T, or V; with the proviso that in a single motif, $X^2$ is not A and $X^{13}$ is not Y; (i) $X^{14}X^{15}R$ (SEQ ID NO:29) or $DX^{14}X^{15}R$ (SEQ ID NO:30), wherein, $X^{14}$ is V or I, and wherein $X^{15}$ is F, W, H, C, A, S, V, D, Y, E, I, M, or T; and (j) $AX^{16}D$ (SEQ ID NO:31) or $KAX^{16}D$ (SEQ ID NO:32) wherein $X^{16}$ is K, is provided.

Some embodiments of the current disclosure are directed to an engineered cell expressing a non-natural prenyltransferase comprising at least one amino acid substitution (including single and combination variants). The cells can be used to promote production of a cannabinoid, CBGA (3-GOLA), or a derivative thereof. Embodiments of the engineered cell may further optionally include one or more additional metabolic pathway transgene(s) to promote improved cannabinoid formation by increasing cannabinoid precursor flux, to generate a cannabinoid derivative, or to improve recovery of the cannabinoid from the engineered cell.

Other embodiments are directed to compositions including an engineered cell, such as cell culture compositions, and also compositions including one or more product(s) produced from the engineered cell. For example, a composition can include a target cannabinoid product produced by the cells, where the composition has been purified to remove cells or other components useful for cell culturing. The composition may be treated to enrich or purify the target product or intermediate thereof.

Other embodiments are directed to methods for forming a prenylated aromatic compound. The method includes a step of contacting a hydrophobic substrate and an aromatic substrate with a non-natural prenyltransferase of the disclosure, wherein contacting forms a prenylated aromatic compound. Exemplary aromatic substrates include olivetol, olivetolic acid, divarinol, divarinolic acid, orcinol, and orsellinic acid. The hydrophobic substrate can include an isoprenoid portion, such as geranyl or farnesyl portions, and can include phosphate groups.

Other embodiments of the disclosure are directed to products made from the target cannabinoid product obtained from methods using the engineered cell. Exemplary products include therapeutic or pharmaceutical compositions, medicinal compositions, systems for in vitro use, diagnostic compositions, and precursor compositions for further chemical modification (e.g. decarboxylation of CBGA to CBG by for example heat or a biocatalyst).

Other embodiments of the disclosure are directed to nucleic acids encoding the non-natural prenyltransferases with one or more variant amino acids, as well as expression constructs including the nucleic acids, and engineered cells comprising the nucleic acids or expression constructs.

DESCRIPTION OF THE DRAWINGS

FIG. 3 shows the chemical structures of various aromatic substrate molecules that can be used in a prenyltransferase catalyzed reaction.

FIG. 4 is the amino acid sequence of *Streptomyces antibioticus* AQJ23_40425 (NCBI Accession number KUN17719.1; 305 amino acids long; SEQ ID NO: 1).

FIG. 5 shows an alignment of SEQ ID NO: 1 (*Streptomyces antibioticus* AQJ23_40425) to other prenyltransferase homologs (SEQ ID NOs: 2-15).

FIG. 6 is a table describing prenyltransferase amino acid motifs and variant residues within those motifs that were identified via HT screening of prenyltransferase variant libraries and that affect activity and selectivity on OLA and GPP.

DETAILED DESCRIPTION

The embodiments of the description described herein are not intended to be exhaustive or to limit the disclosure to the precise forms disclosed in the following detailed description. Rather, the embodiments are chosen and described so that others skilled in the art can appreciate and understand the principles and practices of the description.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

Figure 1:
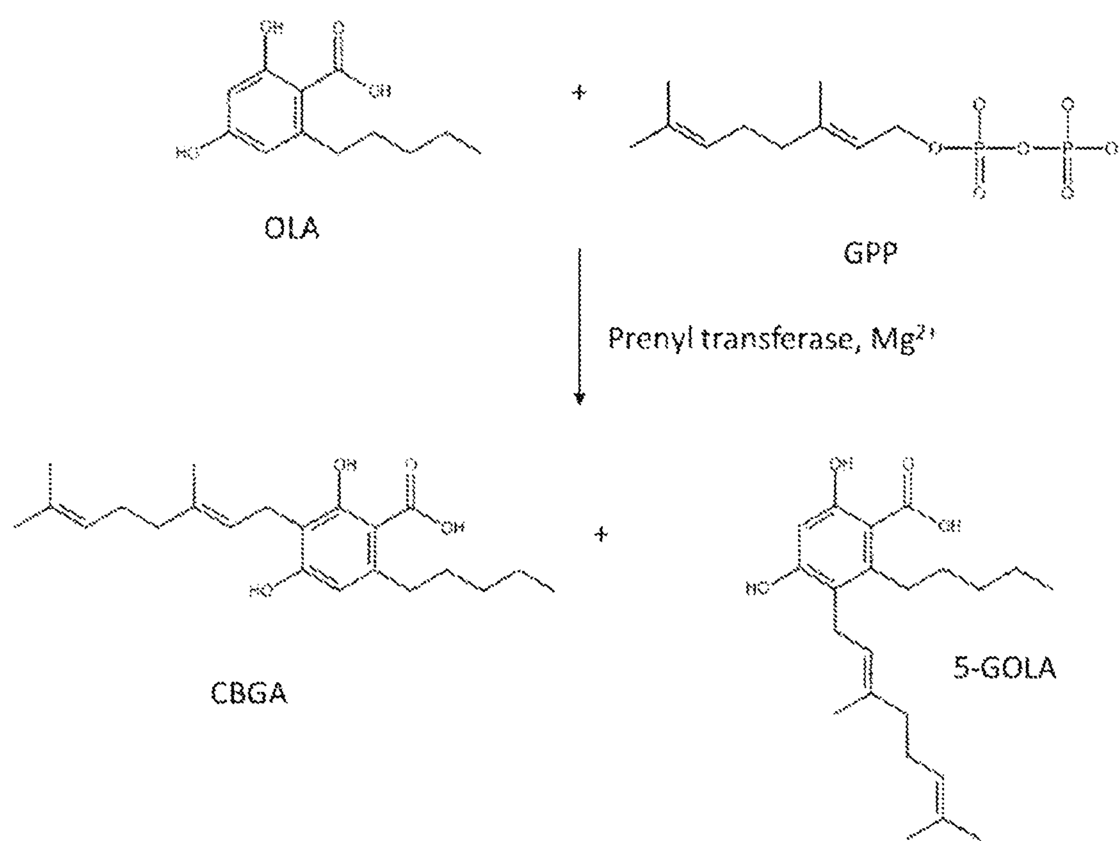
FIG. 1 shows prenyltransferase-catalyzed reaction of olivetolic acid (OLA) and geranyl diphosphate (GPP) to form the products 3-geranyl-olivetolate (3-GOLA; cannabigerolic acid; CBGA) and 5-geranyl-olivetolate (5-GOLA)

Generally, the disclosure provides non-natural prenyltransferases that are (a) enzymatically capable of at least two fold greater rate of formation of 3-geranyl-olivetolate (3-GOLA; cannabigerolic acid; CBGA) from geranyl pyrophosphate and olivetolic acid, as compared to the wild type prenyltransferase or; (b) regioselective to CBGA (3-geranyl-olivetolate, 3-GOLA); or both (a) and (b). Nucleic acids encoding the non-natural prenyltransferases, as well as expression constructs including the nucleic acids, and engineered cells comprising the nucleic acids or expression constructs are described. FIG. 1 shows reaction of olivetolic acid (OLA) and geranyl diphosphate (GPP) to form the products 3-geranyl-olivetolate (3-GOLA; cannabigerolic acid; CBGA) and 5-geranyl-olivetolate (5-GOLA).

Figure 7A:
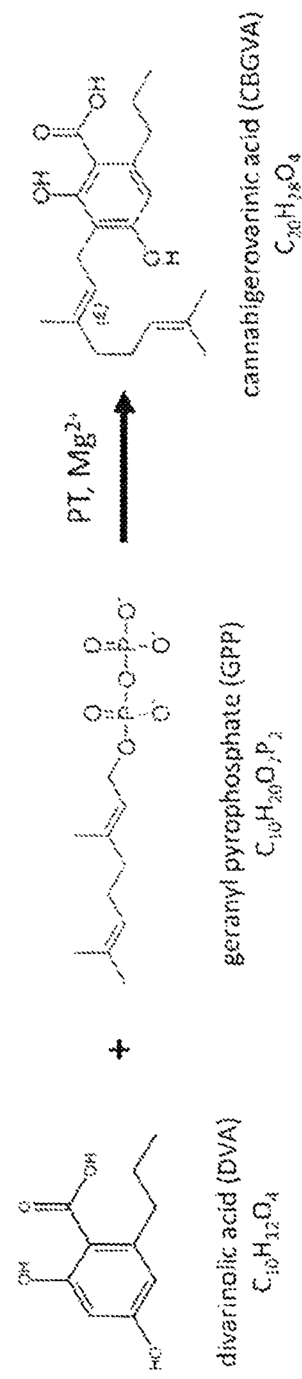
FIG. 7A shows reaction of DVA with GPP to form CBGVA.
Figure 7B:
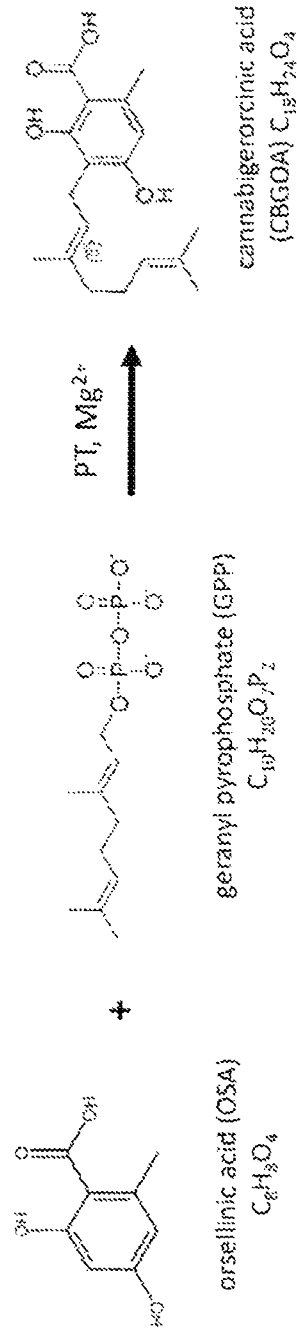
FIG. 7B shows reaction of OSA with GPP to form CBGOA.

The disclosure also provides non-natural prenyltransferases that include at least one amino acid variation enzymatically capable of either (a1) at least two fold greater rate of formation of cannabigerovarinic acid (CBGVA) from geranyl pyrophosphate and divarinolic acid (DVA), as compared to the wild type prenyltransferase; (a2) 50% or greater regioselectivity to 3-geranyl-divarinolic acid (3-GDVA), or both (a1) and (a2); or (b1) at least two fold greater rate of formation of cannabigerorcinic acid (CBGOA) from geranyl pyrophosphate and orsellinic acid (OSA), as compared to the wild type prenyltransferase; (b2) 50% or greater regioselectivity to 3-geranyl-orsellinate (3-GOSA); or both (b1) and (b2). FIG. 7A shows reaction of divarinolic acid (DVA) and geranyl diphosphate (GPP) to form the product cannabigerovarinic acid (CBGVA); and FIG. 7B shows reaction of orsellinic acid (OSA) and geranyl diphosphate (GPP) to form the product cannabigerorcinic acid (CBGOA).

Figure 8:
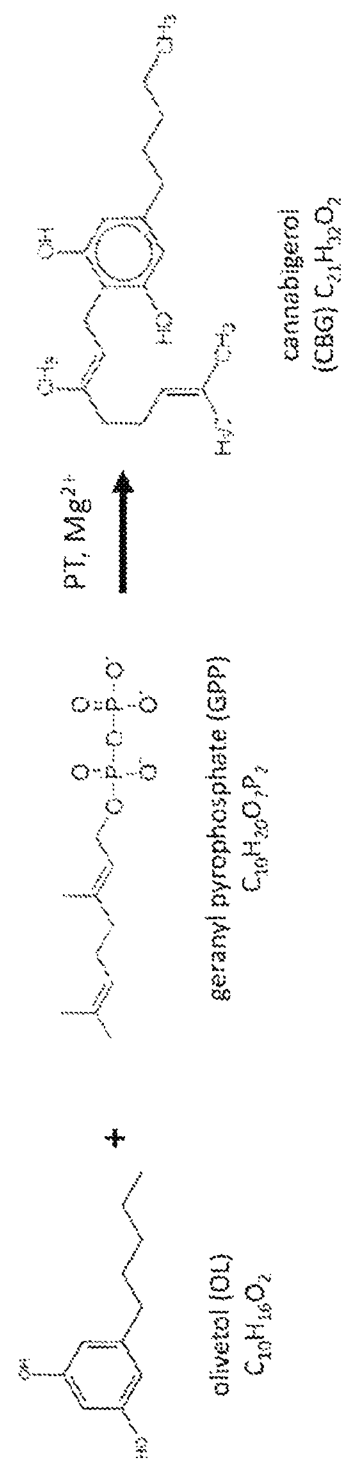
FIG. 8 shows reaction of olivetol with GPP to form CBG (2-GOL).

The disclosure also provides non-natural prenyltransferase variants enzymatically capable of regioselectively forming a 2-prenylated 5-alkylbenzene-1,3-diol from geranyl pyrophosphate and 5-alkylbenzene-1,3-diol. In certain modes of practice, the 5-alkylbenzene-1,3-diol substrate can be olivetol and the 2-prenylated 5-alkylbenzene-1,3-diol can be cannabigerol (CBG; 2-GOL), the reaction which is shown in FIG. 8.

Cannabigerolic acid (CBGA; CAS #25555-57-1) has the following chemical names (E)-3-(3,7-dimethyl-2,6-octadienyl)-2,4-dihydroxy-6-pentylbenzoic acid, and 3-[(2E)-3,7-dimethylocta-2,6-dien-1-yl]-2,4-dihydroxy-6-pentylbenzoic acid, and the following chemical structure:

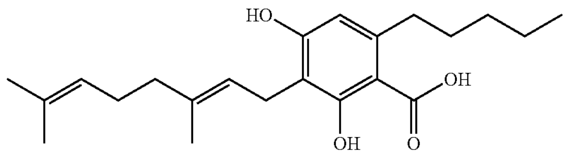 [SMILES: CCCCCc1cc(O)c(C/C=C(\C)CCC=C(C)C)c(O)c1C(=O)O]

CBGA can also be referred to as 3-geranyl-olivetolate (3-GOLA), which reflects the position of the geranyl moiety on the olivetolate moiety.

5-geranyl-olivetolate (5-GOLA) is an enzymatic reaction product of geranyl pyrophosphate and olivetolic acid and has the following structure.

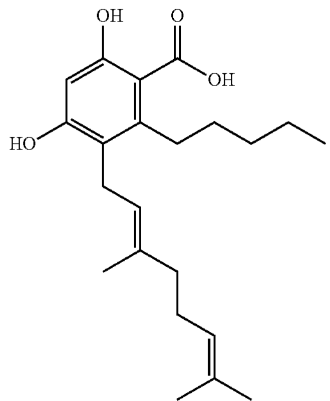 [SMILES: CCCCCc1c(C/C=C(\C)CCC=C(C)C)c(O)cc(O)c1C(=O)O]

As used herein "geranyl-olivetolate" generically refers to either 3-GOLA or 5-GOLA. In an enzymatic reaction using a prenyltransferase variant, "geranyl-olivetolate" products can be produced, although for variants having high regioselectivity to 3-GOLA, very little or trace amounts of 5-GOLA may be produced.

Cannabigerol, the decarboxylated form of 3-GOLA, has the following structure.

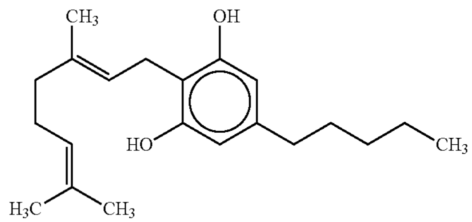

Cannabigerol (CBG; 2-GOL; 2-[(2E)-3,7-dimethylocta-2,6-dienyl]-5-pentylbenzene-1,3-diol; CAS #: 25654-31-3) can be considered a "derivative" of GOLA/CBGA. 4-GOL is the isomer of 2-GOL prenylated at the 4 position on the aromatic ring (i.e., between a hydroxyl group at the 1 or 3 position on the aromatic ring and the pentyl group). CBG can be formed by decarboxylation of CBGA, for example by heat or by catalysis, which can be a biocatalyst such as an enzyme, whole cell, or cell extract. In addition to the use of olivetolic acid (OLA) for forming 3-GOLA/CBGA by reaction as catalyzed by prenyltranferase (see FIG. 1), the disclosure also contemplates the use of other substrate molecules as a replacement to OLA.

Cannabigerol (CBG; 2-GOL) can also be regioselectively formed (i.e., over formation of 4-GOL) from olivetol and geranyl pyrophosphate (see FIG. 8) using non-natural prenyltransferase variants of the disclosure.

Cannabigerovarinic acid (CBGVA; 3-GDVA; 3-[(2E)-3,7-dimethylocta-2,6-dienyl]-2,4-dihydroxy-6-propylbenzoic acid; $C_{20}H_{28}O_4$; #64924-07-8) is a minor cannabinoid.

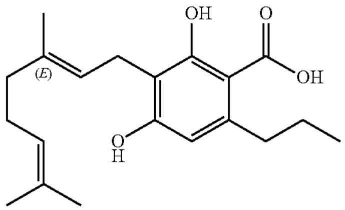 [SMILES: CCCc1cc(O)c(C/C=C(\C)CCC=C(C)C)c(O)c1C(=O)O]

5-GDVA is the isomeric form with the (2E)-3,7-dimethylocta-2,6-dienyl group attached to the 5 position on the aromatic ring. FIG. 7A shows reaction of divarinolic acid (DVA) and geranyl diphosphate (GPP) to form the product cannabigerovarinic acid (CBGVA).

Cannabigerorcinic acid (CBGOA; 3-GOSA; 3-[(2E)-3,7-dimethyl-2,6-octadien-1-yl]-2,4-dihydroxy-6-methyl-benzoic acid; $C_{18}H_{24}O_4$; #69734-83-4) is another minor cannabinoid.

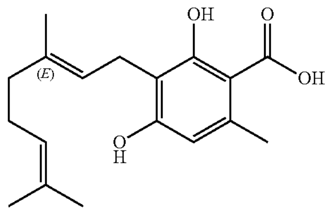 [SMILES: CC(C)=CCC/C(C)=C/Cc1c(O)cc(C)c(C(=O)O)c1O]

5-GOSA is the isomeric form with the (2E)-3,7-dimethyl-2,6-octadien-1-yl group attached to the 5 position on the aromatic ring. FIG. 7B shows reaction of orsellinic acid (OSA) and geranyl diphosphate (GPP) to form the product cannabigerorcinic acid (CBGOA).

The term "regioselective" and "regioselectivity" as used in a "regioselective reaction" refers to a direction of bond making or breaking that occurs preferentially over all other possible directions. A reaction between substrate A and substrate B may yield two or more reaction products (e.g., product C, product D, etc.) Regioselectivity can be understood by determining the molar amount of products formed. For example, in an enzymatic reaction wherein substrate A and substrate B react to form a product mixture of product C and product D, and wherein the molar ratio of product C:product D is greater than 1:1, respectively, in the product mixture, the reaction is regioselective to product C. Wherein the molar ratio of product C:product D is 9:1 or greater, respectively, in the product mixture, in the product mixture, the reaction has 90% or greater regioselectivity to product C.

The disclosure also contemplates methods for, generally, forming a prenylated aromatic compound. The method involves contacting a hydrophobic substrate and an aromatic substrate with a non-natural prenyltransferase of the disclosure to form a prenylated aromatic compound. For example, in particular, the disclosure contemplates use of various aromatic substrates such as olivetol, olivetolic acid, divarinol, divarinolic acid, orcinol, and orsellinic acid in such a prenyltransferase-catalyzed reaction. The hydrophobic substrate can include an isoprenoid portion, a geranyl portion, a farnesyl portions, and one or more phosphate groups. The method can be performed in vivo (e.g., within the engineered cell) or in vitro.

Also described are engineered cells expressing a non-natural prenyltransferase, optionally including one or more additional metabolic pathway transgene(s); cell culture compositions including the cells; methods for promoting production of the target cannabinoid or derivative thereof from the cells; compositions including the target cannabinoid or derivative; and products made from the target product or intermediate.

The term "non-naturally occurring", when used in reference to an organism (e.g., microbial) is intended to mean that the organism has at least one genetic alteration not normally found in a naturally occurring organism of the referenced species. Naturally-occurring organisms can be referred to as "wild-type" such as wild type strains of the referenced species. Likewise, a "non-natural" polypeptide or nucleic acid can include at least one genetic alteration not normally found in a naturally-occurring polypeptide or nucleic acid. Naturally-occurring organisms, nucleic acids, and polypeptides can be referred to as "wild-type" or "original" such as wild type strains of the referenced species. Likewise, amino acids found in polypeptides of the wild type organism can be referred to as "original" with regards to any amino acid position.

A genetic alteration that makes an organism non-natural can include, for example, modifications introducing expressible nucleic acids encoding metabolic polypeptides, other nucleic acid additions, nucleic acid deletions and/or other functional disruption of the organism's genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon.

For example, in order to provide a soluble aromatic prenyltransferase variant, a soluble ABBA type prenyltransferase from *Streptomyces antibioticus* AQJ23_40425 (NCBI Accession number KUN17719.1; 305 amino acids long; SEQ ID NO: 1), can be selected as a template. Variants, as described herein, can be created by introducing into the template one or more amino acid substitutions to test for increased activity and improved regioselectivity to CBGA (3-GOLA).

In some cases, a "homolog" of the prenyltransferase SEQ ID NO: 1, is first identified. A homolog is a gene or genes that are related by vertical descent and are responsible for substantially the same or identical functions in different organisms. Genes are related by vertical descent when, for example, they share sequence similarity of sufficient amount to indicate they are homologous or related by evolution from a common ancestor. Genes that are orthologous can encode proteins with sequence similarity of about 45% to 100% amino acid sequence identity, and more preferably about 60% to 100% amino acid sequence identity. Genes can also be considered orthologs if they share three-dimensional structure but not necessarily sequence similarity, of a sufficient amount to indicate that they have evolved from a common ancestor to the extent that the primary sequence similarity is not identifiable. Paralogs are genes related by duplication within a genome, and can evolve new functions, even if these are related to the original one.

Genes sharing a desired amount of identify (e.g., 45%, 50%, 55%, or 60% or greater) to the *Streptomyces antibioticus* AQJ23_4042 prenyltransferase, including homologs, orthologs, and paralogs, can be determined by methods well known to those skilled in the art. For example, inspection of nucleic acid or amino acid sequences for two polypeptides will reveal sequence identity and similarities between the compared sequences. Based on such similarities, one skilled in the art can determine if the similarity is sufficiently high to indicate the proteins are related through evolution from a common ancestor.

Computational approaches to sequence alignment and determination of sequence identity include global alignments and local alignments. Global alignment uses global optimization to forces alignment to span the entire length of all query sequences. Local alignments, by contrast, identify regions of similarity within long sequences that are often widely divergent overall. For understanding the identity of a target sequence to the *Streptomyces antibioticus* s AQJ23_4042 prenyltransferase template a global alignment can be used. Optionally, amino terminal and/or carboxy-terminal sequences of the target sequence that share little or no identity with the template sequence can be excluded for a global alignment and generation of an identity score.

Algorithms well known to those skilled in the art, such as Align, BLAST, Clustal W and others compare and determine a raw sequence similarity or identity, and also determine the presence or significance of gaps in the sequence which can be assigned a weight or score. Such algorithms also are known in the art and are similarly applicable for determining nucleotide or amino acid sequence similarity or identity. Parameters for sufficient similarity to determine relatedness are computed based on well-known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 45% to 100% sequence identity. Proteins that are unrelated can have an identity which is essentially the same as would be expected to occur by chance if a database of sufficient size is scanned (about 5%).

Pairwise global sequence alignment can be carried out using *Streptomyces antibioticus* AQJ23_4042 prenyltransferase SEQ ID NO: 1 as the template. Alignment can be performed using the Needleman-Wunsch algorithm (Needleman, S. & Wunsch, C. A general method applicable to the search for similarities in the amino acid sequence of two proteins J. Mol. Biol, 1970, 48, 443-453) implemented through the BALIGN tool (http://balign.sourceforge.net/). Default parameters are used for the alignment and BLOSUM62 was used as the scoring matrix. The disclosure also relates to Applicant's first discovery of wild-type sequences disclosed herein as a prenyltransferase and as having improved activity as also described herein; such wild-type sequences previously annotated as "hypothetical protein" or "putative protein." Based in least on Applicant's identification, testing, motif identification, and sequence alignments (see FIG. 5), the current disclosure further allows for the identification of prenyltransferases suitable for use in engineered cells and methods of the disclosure, such as creating variants as described herein.

For the purpose of amino acid position numbering, SEQ ID NO: 1 is used as the reference sequence. For example, mention of amino acid position 49 is in reference to SEQ ID NO:1, but in the context of a different prenyltransferase sequence (a target sequence or other template sequence) the corresponding amino acid position for variant creation may have the same or different position number, (e.g. 48, 49 or 50). In some cases, the original amino acid and its position on the SEQ ID NO: 1 reference template will precisely correlate with the original amino acid and position on the target prenyltransferase. In other cases, the original amino acid and its position on the SEQ ID NO: 1 template will correlate with the original amino acid, but its position on the target will not be in the corresponding template position. However, the corresponding amino acid on the target can be a predetermined distance from the position on the template, such as within 10, 9, 8, 7, 6, 5, 4, 3, 2, or 1 amino acid positions from the template position. In other cases the original amino acid on the SEQ ID NO: 1 template will not precisely correlate with the original amino acid on the target. However, one can understand what the corresponding amino acid on the target sequence is based on the general location of the amino acid on the template and the sequence of amino acids in the vicinity of the target amino acid, especially referring to the alignment provided in FIG. 5. It is understood that additional alignments can be generated with prenyltransferase sequences not specifically disclosed herein, and such alignments can be used to understand and generate new prenyltransferase variants in view of the current disclosure. In some modes of practice, the alignments can allow one to understand common or similar amino acids in the vicinity of the target amino acid, and those amino acids may be viewed as "sequence motif" having a certain amount of identity or similarity to between the template and target sequences. Those sequence motifs can be used to describe portions of prenyltransferase sequences where variant amino acids are located, and the type of variation(s) that can be present in the motif.

In some cases, it can be useful to use the Basic Local Alignment Search Tool (BLAST) algorithm to understand the sequence identity between an amino acid motif in a template sequence and a target sequence. Therefore, in preferred modes of practice, BLAST is used to identify or understand the identity of a shorter stretch of amino acids (e.g. a sequence motif) between a template and a target protein. BLAST finds similar sequences using a heuristic method that approximates the Smith-Waterman algorithm by locating short matches between the two sequences. The (BLAST) algorithm can identify library sequences that resemble the query sequence above a certain threshold. Exemplary parameters for determining relatedness of two or more sequences using the BLAST algorithm, for example, can be as set forth below. Briefly, amino acid sequence alignments can be performed using BLASTP version 2.0.8 (Jan. 5, 1999) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.0.6 (Sep. 16, 1998) and the following parameters: Match: 1; mismatch: −2; gap open: 5; gap extension: 2; x_dropoff: 50; expect: 10.0; wordsize: 11; filter: off. Those skilled in the art will know what modifications can be made to the above parameters to either increase or decrease the stringency of the comparison, for example, and determine the relatedness of two or more sequences.

FIG. 5 shows an alignment of SEQ ID NO: 1 (*Streptomyces antibioticus* AQJ23_40425) to other prenyltransferase homologs (SEQ ID NOs 2-15). These homologs were found by BLAST search, and range in sequence identity to SEQ ID NO: 1 from 88.9%-50.8% (SEQ ID NOs 2-15). Homologs were tested for activity on OLA and GPP in cell lysate. Low, but measurable, activity was identified in all 15 homologs, with SEQ ID NO: 1 among the highest observed. The low activities of wild-type homologs observed are in accord with that reported by Kumano, as previously mentioned.

In some embodiments, a prenyltransferase template into which the one or more variations (also referred to herein as mutation or substitution) are introduced to create a variant is a prenyltransferase sequence having 50% or greater identity, 60% or greater identity, 65% or greater identity, 70% or greater identity, 75% or greater identity, 80% or greater identity, 85% or greater identity, 87.5% or greater identity, 90% or greater identity, 92.5% or greater identity, or 95% or greater identity, to SEQ ID NO:1. In other embodiments the prenyltransferase template is any of SEQ ID NO. 2-15, and preferably SEQ ID NO:1 or SEQ ID NO:15. Variants of the prenyltransferase template preferably include at least (i) Q159H and (ii) Q293W, Q293H, Q293C, Q293A, Q293S, Q293V, Q293D, Q293Y, or Q293E mutations as described herein, or even more preferably (i) Q159H and (ii) Q293W, mutations as described herein;

One, or more than one, amino acid variation can be described relative to the location of a particular amino acid in a wild type prenyltransferase template sequence. Identification of locations in the template that when substituted with variant amino acids which provide desired activity and regioselectivity can be determined by testing methods as described herein.

For example, in the prenyltransferase template SEQ ID NO: 1 one or more of the following positions may be subject to substitution with an amino acid that is different than the wild type amino acid at that location: S49, F121, T124, Q159, S175, S212, 1232, T267, L268, A285, Y286, Q293, and F300.

However, in other prenyltransferase templates, the location of the target amino acid for substitution may be different but corresponds to the positions identified for SEQ ID NO. 1, which is the reference template herein. For example, in a prenyltransferase sequence that is different than SEQ ID NO: 1, the target amino acids can be shifted in the range of 10 to −1, or in the range of +1 to +10, based on the particular amino acid variation location. For example, using the alignment of FIG. 5 as a guide, amino acid position 159 of SEQ ID NO: 1 corresponds to position 161 in SEQ ID NO:2, and amino acid position 293 of SEQ ID NO: 1 corresponds to position 295 in SEQ ID NO:2. In some cases, the shift can vary along the length of the sequence that is aligned to SEQ ID NO:1. For example, the shift may increase or decrease after a first stretch of amino acids in the aligned sequence, an then may increase or decrease after a second stretch of amino acids in the aligned sequence, etc. The shift of shifts can be determined by the gaps between the template and aligned sequence along the length of the proteins.

Art known methods can be used for the testing the enzymatic activity of prenyltransferase, and such methods can be used to test activity of prenyltransferase variant enzymes as well. As a general matter, an in vitro reaction composition including a prenyltransferase variant (purified or in cell lysate or cell extract), geranyl pyrophosphate and olivetolic acid (substrates) can convert the substrates to the product geranyl-olivetolate (e.g., GOLA). Of particular interest herein is conversion of geranyl pyrophosphate and olivetolic acid to CBGA. See the attached figures.

In some embodiments, non-natural prenyltransferases with one or more variant amino acids as describe herein are enzymatically capable of at least two-fold, at least three-fold, at least four-fold, at least five-fold, at least six-fold, at least seven-fold, at least eight-fold, at least nine-fold, at least ten-fold, at least eleven-fold, at least twelve-fold, at least-thirteen fold, at least fourteen-fold, at least fifteen-fold, at least sixteen-fold, at least seventeen-fold, at least eighteen-fold, at least-nineteen fold, or at least-twenty fold greater rate of formation of cannabigerolic acid from geranyl pyrophosphate and olivetolic acid, as compared to the wild type prenyltransferase. Variants were also identified that displayed very high activity on the order of about 300 fold or greater rate of formation of cannabigerolic acid from geranyl pyrophosphate and olivetolic acid, as compared to the wild type prenyltransferase. For example, the increase in rate of formation of cannabigerolic acid from geranyl pyrophosphate and olivetolic acid, as compared to the wild type prenyltransferase, can be in the range of about 2× to about 300×, about 5× to about 300×, or about 10× to about 300× as determined in an in vitro enzymatic reaction using purified prenyltransferase variant.

Non-natural prenyltransferases with one or more variant amino acids of the disclosure can be enzymatically capable of at least two-fold, at least three-fold, at least four-fold, at least five-fold, at least six-fold, at least seven-fold, at least eight-fold, at least nine-fold, at least ten-fold, at least eleven-fold, at least twelve-fold, at least-thirteen fold, at least fourteen-fold, at least fifteen-fold, at least sixteen-fold, at least seventeen-fold, at least eighteen-fold, at least-nineteen fold, or at least-twenty fold greater rate of formation of cannabigerovarinic acid (CBGVA) from geranyl pyrophosphate (GPP) and divarinolic acid (DVA), or of cannabigerorcinic acid (CBGOA) from geranyl pyrophosphate (GPP) and orsellinic acid (OSA), as compared to the wild type prenyltransferase.

For example, the increase in rate of formation of CBGVA from GPP and DVA as compared to the wild type prenyltransferase, can be in the range of about 2× to about 450×, about 5× to about 400×, or about 10× to about 375×. The increase in rate of formation of CBGOA from GPP and OSA as compared to the wild type prenyltransferase, can be in the range of about 2× to about 600×, about 5× to about 575×, or about 10× to about 550×.

Non-natural prenyltransferases with one or more variant amino acids of the disclosure can be enzymatically capable of at least two-fold, at least three-fold, at least four-fold, at least five-fold, at least six-fold, at least seven-fold, at least eight-fold, at least nine-fold, at least ten-fold, at least eleven-fold, at least twelve-fold, at least-thirteen fold, at least fourteen-fold, at least fifteen-fold, at least sixteen-fold, at least seventeen-fold, at least eighteen-fold, at least-nineteen fold, or at least-twenty fold greater rate of formation of cannabigerovarinic acid (CBGVA) from geranyl pyrophosphate (GPP) and divarinolic acid (DVA), or of cannabigerorcinic acid (CBGOA) from geranyl pyrophosphate (GPP) and orsellinic acid (OSA), as compared to the wild type prenyltransferase.

For example, the increase in rate of formation of CBGVA from GPP and DVA as compared to the wild type prenyltransferase, can be in the range of about 2× to about 450×, about 5× to about 400×, or about 10× to about 375×. The increase in rate of formation of CBGOA from GPP and OSA as compared to the wild type prenyltransferase, can be in the range of about 2× to about 600×, about 5× to about 575×, or about 10× to about 550×.

Non-natural prenyltransferases with one or more variant amino acids of the disclosure can be enzymatically capable of at least two-fold, at least three-fold, at least four-fold, at least five-fold, at least six-fold, at least seven-fold, at least eight-fold, at least nine-fold, at least ten-fold, at least eleven-fold, at least twelve-fold, at least-thirteen fold, at least fourteen-fold, at least fifteen-fold, at least sixteen-fold, at least seventeen-fold, at least eighteen-fold, at least-nineteen fold, or at least-twenty fold greater rate of formation of a 2-prenylated 5-alkylbenzene-1,3-diol (e.g., CBG; 2-GOL) from geranyl pyrophosphate and 5-alkylbenzene-1,3-diol (e.g., olivetol), as compared to the wild type prenyltransferase.

For example, the increase in rate of formation of CBG from GPP and olivetol, as compared to the wild type prenyltransferase, can be in the range of about 2× to about 200×, about 5× to about 175×, or about 10× to about 150×.

The at least two-fold increase of enzymatic activity can be seen in in vitro reactions using cell lysates from bacteria expressing the prenyltransferase variants, or from purified preparations of the prenyltransferase variants (e.g., purified from cell lysates). It was observed that for many variants, purified preparations showed increased enzymatic activity over the cell lysates, indicating that in some cell lysates prenyltransferase may suffer from insolubility or other event that reduces enzyme activity. As such, a purified prenyltransferase preparation may show 2-fold, 5-fold, 10-fold, or even 20-fold improvement of enzyme activity over the corresponding cell lysate, controlling for equal amounts of the prenyltransferase in the enzymatic assay.

Using a purified prenyltransferase preparation the rate of formation of CBGA can be determined. The rate can be expressed in terms of μM CBGA/min/μM enzyme. Reaction conditions can be as follows: 50 mM HEPES, pH 7.5 buffer containing 1 mM geranyl pyrophosphate (Sigma-Aldrich) and 1 mM olivetolic acid (Santa Cruz Biotechnology) and 5 mM magnesium chloride. Reactions are initiated by addition of purified phenyltransferase and then incubated for a measured period of 0.5 to 2 hours, quenched with acetonitrile to a final concentration of 65%, then centrifuged to pellet denatured protein. Supernatants are transferred to 96-well plates for GCMS analysis of CBGA (3-GOLA) and 5-GOLA.

Likewise, using a purified prenyltransferase variant preparation, the rate of formation of cannabigerovarinic acid (CBGVA) from geranyl pyrophosphate and divarinolic acid (DVA) can be determined using similar methods, as well as the rate of formation of cannabigerorcinic acid (CBGOA) from geranyl pyrophosphate and orsellinic acid (OSA) (see FIGS. 7A and 7B) and the rate of formation of cannabigerol (CBG) from olivetol and geranyl pyrophosphate (see FIG. 8).

In embodiments, the phenyltransferase variants provide a rate of formation of CBGA of greater than 0.005 μM CBGA/min/μM enzyme, greater than about 0.010 μM CBGA/min/μM enzyme, greater than about 0.020 μM CBGA/min/μM enzyme, greater than about 0.050 μM CBGA/min/μM enzyme, greater than about 0.100 μM CBGA/min/μM enzyme, greater than about 0.250 μM CBGA/min/μM enzyme, greater than about 0.500 μM CBGA/min/μM enzyme, such as in the range of about 0.005

μM or 0.010 μM to about 1.250 μM CBGA/min/μM enzyme, or in the range of about 0.020 μM to about 1.0 μM CBGA/min/μM enzyme.

In embodiments, the phenyltransferase variants provide a rate of formation of CBGVA from DVA and GPP, of CBGOA from OSA and GPP, or of CBG from olivetol and GPP, according to any of the rates as described herein.

In some embodiments, non-natural prenyltransferases with one or more variant amino acids as describe herein are enzymatically capable of providing regioselectivity to 3-geranyl-olivetolate (CBGA; 3-GOLA). In some embodiments the non-natural prenyltransferases with one or more variant amino acids providing an amount of regioselectivity to 3-geranyl-olivetolate CBGA of 60% or greater, 70% or greater, 80% or greater, 85% or greater, 90% or greater, 91% or greater, 92% or greater, 93% or greater, 94% or greater, 95% or greater, 96% or greater, 97% or greater, 98% or greater, 99% or greater, 99.2% or greater, 99.4% or greater, 99.5% or greater, 99.6% or greater, 99.7% or greater, 99.8% or greater, 99.9% or greater, 99.95% or greater, or 100% regioselectivity to 3-geranyl-olivetolate (CBGA; 3-GOLA) of the total geranyl olivetolate (3-GOLA plus 5-GOLA) as determined in an in vitro enzymatic reaction using purified prenyltransferase variant. Accordingly, of the geranyl-olivetolate reaction products, 5-GOLA is in an amount of less than 10% (wt), less than 9% (wt), less than 8% (wt), less than 7% (wt), less than 6 (wt), less than 5% (wt), less than 4% (wt), less than 3% (wt), less than 2% (wt), less than 1% (wt), less than 0.8% (wt), less than 0.6% (wt), less than 0.5% (wt), less than 0.4% (wt), less than 0.3% (wt), less than 0.2% (wt), less than 0.1% (wt), less than 0.05% (wt) or 0.0% (wt). In view of the improved regioselectivity of the prenyltransferase variants, the disclosure also provides compositions that are enriched for desired cannabinoids and derivatives thereof. In particular, the disclosure provides compositions enriched for CBGA (3-GOLA) and/or CBG. Enriched compositions include those that are pharmaceutical compositions as well as those that are used for non-pharmaceutical purposes, such as having 90% or greater 3-GOLA as described herein, or other desired derivatives depending on the provided substrate (e.g. olivetol, olivetolic acid, et.) as described elsewhere herein. In some embodiments, non-natural prenyltransferase with one or more variant amino acids as describe herein display an increase in rate of formation of cannabigerolic acid from geranyl pyrophosphate and olivetolic acid, in any of the amounts described herein, and regioselectivity in any of the amounts as described herein.

In some embodiments, non-natural prenyltransferases with one or more variant amino acids as describe herein are enzymatically capable of providing regioselectivity to 3-geranyl-orsellinate (3-GOSA), an isomer of cannabigerorcinic acid (CBGOA) formed after reacting GPP and OSA. In some embodiments the non-natural prenyltransferases with one or more variant amino acids providing an amount of regioselectivity to 3-GOSA of 60% or greater, 70% or greater, 80% or greater, 85% or greater, 90% or greater, 91% or greater, 92% or greater, 93% or greater, 94% or greater, 95% or greater, 96% or greater, 97% or greater, 98% or greater, 99% or greater, 99.2% or greater, 99.4% or greater, 99.5% or greater, 99.6% or greater, 99.7% or greater, 99.8% or greater, 99.9% or greater, 99.95% or greater, or 100% regioselectivity to 3-GOSA of the total geranyl-orsellinate (3-GOSA plus 5-GOSA) as determined in an in vitro enzymatic reaction using purified prenyltransferase variant.

Accordingly, of the geranyl-orsellinate reaction product, 5-GOSA is in an amount of less than 10% (wt), less than 9% (wt), less than 8% (wt), less than 7% (wt), less than 6 (wt), less than 5% (wt), less than 4% (wt), less than 3% (wt), less than 2% (wt), less than 1% (wt), less than 0.8% (wt), less than 0.6% (wt), less than 0.5% (wt), less than 0.4% (wt), less than 0.3% (wt), less than 0.2% (wt), less than 0.1% (wt), less than 0.05% (wt) or 0.0% (wt). In view of the improved regioselectivity of the prenyltransferase variants, the disclosure also provides compositions that are enriched for 3-GOSA, and derivatives thereof, such as pharmaceutical and non-pharmaceutical compositions having 90% or greater 3-GOSA as described herein, or other desired derivatives thereof.

In some embodiments, non-natural prenyltransferases with one or more variant amino acids as describe herein are enzymatically capable of providing regioselectivity to cannabigerol (CBG; 2-GOL) instead of the 4-GOL isomer, formed after reacting olivetol and GPP. In some embodiments the non-natural prenyltransferases with one or more variant amino acids providing an amount of regioselectivity to 2-GOL of 60% or greater, 70% or greater, 80% or greater, 85% or greater, 90% or greater, 91% or greater, 92% or greater, 93% or greater, 94% or greater, 95% or greater, 96% or greater, 97% or greater, 98% or greater, 99% or greater, 99.2% or greater, 99.4% or greater, 99.5% or greater, 99.6% or greater, 99.7% or greater, 99.8% or greater, 99.9% or greater, 99.95% or greater, or 100% regioselectivity to 2-GOL of the total cannabigerol isomers (2-GOL plus 4-GOL) as determined in an in vitro enzymatic reaction using purified prenyltransferase variant.

Accordingly, of the GPP-olivetol reaction product, 4-GOL is in an amount of less than 10% (wt), less than 9% (wt), less than 8% (wt), less than 7% (wt), less than 6 (wt), less than 5% (wt), less than 4% (wt), less than 3% (wt), less than 2% (wt), less than 1% (wt), less than 0.8% (wt), less than 0.6% (wt), less than 0.5% (wt), less than 0.4% (wt), less than 0.3% (wt), less than 0.2% (wt), less than 0.1% (wt), less than 0.05% (wt) or 0.0% (wt). In view of the improved regioselectivity of the prenyltransferase variants, the disclosure also provides compositions that are enriched for 2-GOL, and derivatives thereof, such as pharmaceutical and non-pharmaceutical compositions having 90% or greater 2-GOL as described herein, or other desired derivatives thereof.

The non-natural prenyltransferases of the disclosure can include one amino acid variation, two amino acid variations, three amino acid variations, four amino acid variations, five amino acid variations, or more than five amino acid variations, from a wild type prenyltransferase template sequence. The variation(s) can be any single or combinations as described herein. Optional variations, other than those described herein, can be used with any single or combinations as described herein, wherein the optional variations are not detrimental to the desired activity of the prenyltransferase variants. Exemplary optional variations include those such as conservative amino acid substitutions that do not considerably alter protein properties.

FIG. 6 lists positions of amino acids mutations providing (a) enzymatic activity of at least two-fold greater rate of formation of cannabigerolic acid (CBGA) from geranyl pyrophosphate and olivetolic acid, as compared to the wild type prenyltransferase or; (b) 50% or greater regioselectivity to CBGA (3-GOLA); or both (a) and (b). The mutations are described with reference to the numbering of amino acid positions in SEQ ID NO: 1; however, one or more of the mutations can be introduced into SEQ ID NO:1 at the recited positions or into other prenyltransferase homologs at corresponding amino acid locations to provide variants with desired activity and/or regioselectivity. The alignments shown in FIG. 5, or alignments of any other soluble prenyltransferase sequence with SEQ ID NO:1, can be used as a guide for introducing one or more variations into a desired template sequence.

Results of the mutagenesis procedures revealed a number of amino acid variants along the prenyltransferase template showing at least two-fold greater rate of formation of cannabigerolic acid (CBGA) from geranyl pyrophosphate and olivetolic acid, as compared to the wild type prenyltransferase or (b) 50% or greater regioselectivity to CBGA (3-GOLA); or both (a) and (b).

Tables 1 and 2 list positions of amino acids mutations providing (a) enzymatic activity of at least two-fold greater rate of formation of cannabigerolic acid (CBGA) from geranyl pyrophosphate (GPP) and olivetolic acid, (b) cannabigerovarinic acid (3-GDVA) from GPP and divarinolic acid (DVA), (c) cannabigerorcinic acid (3-GOSA and 5-GOSA) from GPP and orsellinic acid (OSA), and (d) CBG (2-GOL) from olivetol and GPP, as compared to the wild type prenyltransferase. The data in Tables 1 and 2 also reflects the regioselectivity to CDBA (3-GOLA), 3-GDVA, 3-GOSA, and CBG (2-GOL). The mutations are described with reference to the numbering of amino acid positions in SEQ ID NO: 1 or SEQ ID NO:2. The variant location and identities as set forth in this table, used in combination with the alignments shown in FIG. 5, can be used to introduce the variant amino acids into any other soluble prenyltransferase sequence that can be aligned with SEQ ID NO:1 or 2.

In embodiments, the non-natural prenyltransferase is based on reference template SEQ ID NO:1, or has 50% or greater identity, 60% or greater identity, 65% or greater identity, 70% or greater identity, 75% or greater identity, 80% or greater identity, 85% or greater identity, 87.5% or greater identity, 90% or greater identity, 92.5% or greater identity, or 95% or greater identity, to SEQ ID NO:1, and has one or more amino acid variations at position(s) selected from the group consisting of: 49, 121, 124, 159, 175, 212, 232, 267, 268, 285, 286, 293, and 300 with reference to the amino acid sequence of SEQ ID NO:1. As noted previously, positions recited herein are with reference to the amino acid sequence of SEQ ID NO:1, even if not expressly recited as such.

In other embodiments the prenyltransferase template is any of SEQ ID NO. 2-15, or a homolog thereof, that include these variations at the corresponding positions. For example, in SEQ ID NO:2 the variant positions are shifted +2, from these locations, and therefore SEQ ID NO:2 can have one or more amino acid variations at position(s) selected from the group consisting of: 51, 123, 126, 161, 177, 214, 234, 269, 270, 287, 288, 295, and 302 with reference to the amino acid sequence of SEQ ID NO:1. As another example, in SEQ ID NO:15 the variant positions are shifted by different amounts along the length of the protein (i.e., 0 (first stretch), +1 (second stretch), +2 (third stretch), +8 (fourth stretch), and +4 (fifth stretch). As based on the alignment, SEQ ID NO:15 can have one or more amino acid variations at position(s) selected from the group consisting of: 49, 122, 125, 161, 177, 214, 240, 271, 272, 289, 290, 297, and 304 with reference to the amino acid sequence of SEQ ID NO:1.

In embodiments, the non-natural prenyltransferase is based on reference template SEQ ID NO:1, or has 50% or greater identity, 60% or greater identity, 65% or greater identity, 70% or greater identity, 75% or greater identity, 80% or greater identity, 85% or greater identity, 87.5% or greater identity, 90% or greater identity, 92.5% or greater identity, or 95% or greater identity, to SEQ ID NO:1, and has one or more amino acid variations at position(s) selected from the group consisting of: S49T, F121L, T124R, Q159H, Q159R, Q159S, Q159T, Q159Y, Q159A, Q159F, Q159G, Q159I, Q159K, Q159L, Q159M, Q159A, S175H, S175K, S175R, S212H, I232H, T267W, L268Y, A285Y, Y286A, Y286F, Y286L, Y286M, Y286P, Y286T, Y286V, Q293F, Q293W, Q293H, Q293C, Q293A, Q293S, Q293V, Q293D, Q293Y, Q293E, Q293I, Q293M, Q293T, and F300K.

In other embodiments the prenyltransferase template is any of SEQ ID NO. 2-15, or a homolog thereof, that include these variations at the corresponding positions. For example, in SEQ ID NO:2 the variant positions are shifted +2, from these locations. As such, SEQ ID NO:2, or a sequence having identity to SEQ ID NO:2 (e.g., 50% or greater or up to 95% or greater as discussed herein) has one or more amino acid variations at position(s) selected from the group consisting of: S51T, F123L, T126R, Q161H, Q161R, Q161S, Q161T, Q161Y, Q161A, Q161F, Q161G, Q161I, Q161K, Q161L, Q161M, Q161A, S177H, S177K, S177R, S214H, I234H, T269W, L270Y, A287Y, Y288A, Y288F, Y288L, Y288M, Y288P, Y288T, Y288V, Q295F, Q295W, Q295H, Q295C, Q295A, Q295S, Q295V, Q295D, Q295Y, Q295E, Q295I, Q295M, Q295T, and F303K.

Accordingly, expressly contemplated for each template herein, the non-natural prenyltransferase is based on any one of templates SEQ ID NO:2-15, or has 50% or greater identity, 60% or greater identity, 65% or greater identity, 70% or greater identity, 75% or greater identity, 80% or greater identity, 85% or greater identity, 87.5% or greater identity, 90% or greater identity, 92.5% or greater identity, or 95% or greater identity, to any one of SEQ ID NO:2-15, and has one or more amino acid variations at position(s) selected from the group consisting of those positions corresponding to those listed for SEQ ID NO:1.

In embodiments, the non-natural prenyltransferase is based on template SEQ ID NO:1, or has 50% or greater identity, 60% or greater identity, 65% or greater identity, 70% or greater identity, 75% or greater identity, 80% or greater identity, 85% or greater identity, 87.5% or greater identity, 90% or greater identity, 92.5% or greater identity, or 95% or greater identity, to SEQ ID NO:1, and has two or more amino acid variations at position(s) selected from the group consisting of: (i) Q159A and (ii) Q293F, Q293M, Q293F, Q293F; (i) Q159F and (ii) Q293F, Q293W, or Q293H; (i) Q159G and (ii) Q293F; (i) Q159H and (ii) Q293W, Q293H, Q293C, Q293A, Q293S, Q293V, Q293D, Q293Y, or Q293E; (i) Q159I and (ii) Q293F; (i) Q159K and (ii) Q293V or Q293V; (i) Q159L and (ii) Q293W or Q293F; (i) Q159M and (ii) Q293F or Q293W; (i) Q159R and (ii) Q293V, Q293M, or Q293T; (i) Q159S and (ii) Y286I; and (i) S175H and (ii) Q293V.

In other embodiments the prenyltransferase template is any of SEQ ID NO. 2-15, or a homolog thereof, that include these variations at the corresponding positions. For example, in SEQ ID NO:2 the variant positions are shifted +2, from these locations. Accordingly, expressly contemplated for each template, the non-natural prenyltransferase is based on any one of the template SEQ ID NO:2-15 or has 50% or greater identity, 60% or greater identity, 65% or greater identity, 70% or greater identity, 75% or greater identity, 80% or greater identity, 85% or greater identity, 87.5% or greater identity, 90% or greater identity, 92.5% or greater identity, or 95% or greater identity, to the template selected from SEQ ID NO:2-15, and has two or more amino acid variations at position(s) selected from the group consisting of: (i) Q159A and (ii) Q293F, Q293M, Q293F, Q293F; (i) Q159F and (ii) Q293F, Q293W, or Q293H; (i) Q159G and (ii) Q293F; (i) Q159H and (ii) Q293W, Q293H, Q293C, Q293A, Q293S, Q293V, Q293D, Q293Y, or Q293E; (i) Q159I and (ii) Q293F; (i) Q159K and (ii) Q293V or Q293V; (i) Q159L and (ii) Q293W or Q293F; (i) Q159M and (ii) Q293F or Q293W; (i) Q159R and (ii) Q293V, Q293M, or Q293T; (i) Q159S and (ii) Y286I; and (i) S175H and (ii) Q293V.

In embodiments, the non-natural prenyltransferase is based on template SEQ ID NO:1, or has 50% or greater identity, 60% or greater identity, 65% or greater identity, 70% or greater identity, 75% or greater identity, 80% or greater identity, 85% or greater identity, 87.5% or greater identity, 90% or greater identity, 92.5% or greater identity, or 95% or greater identity, to SEQ ID NO:1, and has three or more amino acid variations at position(s) selected from the group consisting of (i) Q159H, (ii) Y286A, and (iii) Q293F, Q293M, or Q293V; (i) Q159H, (ii) Y286I, and (iii) Q293M or Q293V; (i) Q159H, (ii) Y286V, and (iii) Q293F, Q293M, Q293V, or Q293W; (i) Q159L, (ii) S175H, and (iii) Q293F; (i) S175H, (ii), Y286V, and (iii) Q293M; (i) S175H, (ii), Y286I, and (iii) Q293M or Q293V; (i) Q159S, (ii) S175H, and (iii) Y286I; (i) Q159S, (ii) S175R, and (iii) Y286V; (i) Q159S, (ii) S175S, and (iii) Y286I; and (i) Q159S, (ii) S212H, (iii) Y286A or Y286V.

In other embodiments the prenyltransferase template is any of SEQ ID NO. 2-15, or a homolog thereof, that include these variations at the corresponding positions. For example, in SEQ ID NO:2 the variant positions are shifted +2, from these locations. Accordingly, expressly contemplated for each template herein, the non-natural prenyltransferase is based on any one of templates SEQ ID NO:2-15 or has 50% or greater identity, 60% or greater identity, 65% or greater identity, 70% or greater identity, 75% or greater identity, 80% or greater identity, 85% or greater identity, 87.5% or greater identity, 90% or greater identity, 92.5% or greater identity, or 95% or greater identity, to the template selected from SEQ ID NO:2-15, and has three or more amino acid variations at position(s) selected from the group consisting of (i) Q159H, (ii) Y286A, and (iii) Q293F, Q293M, or Q293V; (i) Q159H, (ii) Y286I, and (iii) Q293M or Q293V; (i) Q159H, (ii) Y286V, and (iii) Q293F, Q293M, Q293V, or Q293W; (i) Q159L, (ii) S175H, and (iii) Q293F; (i) S175H, (ii), Y286V, and (iii) Q293M; (i) S175H, (ii), Y286I, and (iii) Q293M or Q293V; (i) Q159S, (ii) S175H, and (iii) Y286I; (i) Q159S, (ii) S175R, and (iii) Y286V; (i) Q159S, (ii) S175S, and (iii) Y286I; and (i) Q159S, (ii) S212H, (iii) Y286A or Y286V.

In embodiments, the non-natural prenyltransferase is based on template SEQ ID NO:1, or has 50% or greater identity, 60% or greater identity, 65% or greater identity, 70% or greater identity, 75% or greater identity, 80% or greater identity, 85% or greater identity, 87.5% or greater identity, 90% or greater identity, 92.5% or greater identity, or 95% or greater identity, to SEQ ID NO:1, and has four or more amino acid variations at position(s) selected from the group consisting of (i) Q159H, (ii) S175H, (iii) Y286A, and (iv) Q293V; (i) Q159H, (ii) S175H, (iii) Y286V, and (iv) Q293M or Q293V; (i) Q159H, (ii) S175R, (iii) Y286I, and (iv) Q293M; (i) Q159L, (ii) S175K, (iii) Y286A, and (iv) Q293V; (i) Q159M, (ii) S175H, (iii) Y286V, and (iv) Q293F; (i) Q159R, (ii) S175H, (iii) Y286I, and (iv) Q293Q; (i) Q159S, (ii) S175H, (iii) Y286V, and (iv) Q293F; (i) Q159S, (ii) S175K, (iii) Y286V, and (iv) Q293V; and (i) Q159S, (ii) S212H, (iii) Y286V, and (iv) Q293M. In other embodiments the prenyltransferase template is any of SEQ ID NO. 2-15, or a homolog thereof, that include these variations at the corresponding positions. For example, in SEQ ID NO:2 the variant positions are shifted +2, from these locations. Accordingly, expressly contemplated for each template herein, the non-natural prenyltransferase is based on any one of templates SEQ ID NO:2-15, or has 50% or greater identity, 60% or greater identity, 65% or greater identity, 70% or greater identity, 75% or greater identity, 80% or greater identity, 85% or greater identity, 87.5% or greater identity, 90% or greater identity, 92.5% or greater identity, or 95% or greater identity, to the template selected from SEQ ID NO:2-15, and has four or more amino acid variations at position(s) selected from the group consisting of (i) Q159H, (ii) S175H, (iii) Y286A, and (iv) Q293V; (i) Q159H, (ii) S175H, (iii) Y286V, and (iv) Q293M or Q293V; (i) Q159H, (ii) S175R, (iii) Y286I, and (iv) Q293M; (i) Q159L, (ii) S175K, (iii) Y286A, and (iv) Q293V; (i) Q159M, (ii) S175H, (iii) Y286V, and (iv) Q293F; (i) Q159R, (ii) S175H, (iii) Y286I, and (iv) Q293Q; (i) Q159S, (ii) S175H, (iii) Y286V, and (iv) Q293F; (i) Q159S, (ii) S175K, (iii) Y286V, and (iv) Q293V; and (i) Q159S, (ii) S212H, (iii) Y286V, and (iv) Q293M.

In embodiments, the non-natural prenyltransferase is based on template SEQ ID NO:1, or has 50% or greater identity, 60% or greater identity, 65% or greater identity, 70% or greater identity, 75% or greater identity, 80% or greater identity, 85% or greater identity, 87.5% or greater identity, 90% or greater identity, 92.5% or greater identity, or 95% or greater identity, to SEQ ID NO:1, and has five or more amino acid variations at position(s) selected from the group consisting of (i) Q159H, (ii) S175R, (iii) S212H, (iv) Y286A, and (v) Q293V; and (i) Q159R, (ii) S175R, (iii) S212H, (iv) Y286I, and (v) Q293M.

In other embodiments the prenyltransferase template is any of SEQ ID NO. 2-15, or a homolog thereof, that include these variations at the corresponding positions. For example, in SEQ ID NO:2 the variant positions are shifted +2, from these locations. Accordingly, expressly contemplated for each template herein, the non-natural prenyltransferase is based on any one of templates SEQ ID NO:2-15, or has 50% or greater identity, 60% or greater identity, 65% or greater identity, 70% or greater identity, 75% or greater identity, 80% or greater identity, 85% or greater identity, 87.5% or greater identity, 90% or greater identity, 92.5% or greater identity, or 95% or greater identity, to the template selected from SEQ ID NO:2-15, and has five or more amino acid variations at position(s) selected from the group consisting of (i) Q159H, (ii) S175R, (iii) S212H, (iv) Y286A, and (v) Q293V; and (i) Q159R, (ii) S175R, (iii) S212H, (iv) Y286I, and (v) Q293M.

In some embodiments, the non-natural prenyltransferase comprises the following amino acid motif: $FX^3M$(SEQ ID NO:16), or $VFX^3MA$ (SEQ ID NO:17) wherein; $X^3$ is T. Amino acid position 49 of SEQ ID NO:1 corresponds to $X^3$.

In some embodiments, the non-natural prenyltransferase comprises the following amino acid motif: $X^4FPX^5$ (SEQ ID NO:18), wherein $X^4$ is F or L, and wherein $X^5$ is T or R, with the proviso that in a single motif, $X^4$ is not F, and $X^5$ is not T. Amino acid positions 121 and 124 of SEQ ID NO:1 correspond to $X^4$ and $X^5$.

In some embodiments, the non-natural prenyltransferase comprises the following amino acid motif: $VX^6M$ (SEQ ID NO:19) or $KVX^6MT$ (SEQ ID NO:20) wherein $X^6$ is selected from the group consisting of H, R, S, T, Y, A, F, G, I, K, L, M, and A. Amino acid position 159 of SEQ ID NO:1 corresponds to $X^6$.

In some embodiments, the non-natural prenyltransferase comprises the following amino acid motif: $FX^7E$ (SEQ ID NO:21) or $YFX^7EL$ (SEQ ID NO:22) wherein $X^7$ is selected from the group consisting of H, K, and R. Amino acid position 175 of SEQ ID NO:1 corresponds to $X^7$.

In some embodiments, the non-natural prenyltransferase comprises the following amino acid motif: $FX^8V$ (SEQ ID NO:23) or $SFX^8VY$ (SEQ ID NO:24) wherein $X^8$ is H. Amino acid position 212 of SEQ ID NO:1 corresponds to $X^8$.

In some embodiments, the non-natural prenyltransferase comprises the following amino acid motif: $VX^9S$ (SEQ ID NO:25) or $AVX^9SN$ (SEQ ID NO:26) wherein $X^9$ is H. Amino acid position 232 of SEQ ID NO:1 corresponds to $X^9$.

In some embodiments, the non-natural prenyltransferase comprises the following amino acid motif: $RX^{10}X^{11}V$ (SEQ ID NO:27), wherein, $X^{10}$ is T or W, and wherein $X^{11}$ is L or Y; with the proviso that in a single motif, $X^{10}$ is not T and $X^{11}$ is not L. Amino acid positions 267 and 268 of SEQ ID NO:1 correspond to $X^{10}$ and $X^{11}$.

In some embodiments, the non-natural prenyltransferase comprises the following amino acid motif: $GX^{12}X^{13}Y$ (SEQ ID NO:28), wherein, $X^{12}$ is A or Y, and wherein $X^{13}$ is Y, A, F, L, M, P, T, or V; with the proviso that in a single motif, $X^{12}$ is not A and $X^{13}$ is not Y. Amino acid positions 285 and 286 of SEQ ID NO:1 correspond to $X^{12}$ and $X^{13}$.

In some embodiments, the non-natural prenyltransferase comprises the following amino acid motif: $X^{14}X^{15}R$ (SEQ ID NO:29) or $DX^{14}X^{15}R$ (SEQ ID NO:30), wherein, $X^{14}$ is V or I, and wherein $X^{15}$ is F, W, H, C, A, S, V, D, Y, E, I, M, or T. Amino acid positions 292 and 293 of SEQ ID NO:1 correspond to $X^{14}$ and $X^{15}$.

In some embodiments, the non-natural prenyltransferase comprises the following amino acid motif: $AX^{16}D$ (SEQ ID NO:31) or $KAX^{16}D$ (SEQ ID NO:32) wherein $X^{16}$ is K. Amino acid position 300 of SEQ ID NO:1 corresponds to $X^{16}$.

In other embodiments the prenyltransferase template is any of SEQ ID NO. 1 or 2-15, or a homolog thereof, that includes one or more variations at the corresponding positions as described relative to these motifs. The template can have one or more of the motifs as described herein and 50% or greater identity, 60% or greater identity, 65% or greater identity, 70% or greater identity, 75% or greater identity, 80% or greater identity, 85% or greater identity, 87.5% or greater identity, 90% or greater identity, 92.5% or greater identity, or 95% or greater identity, to the template selected from SEQ ID NO:1-15.

In some embodiments, two, three, four, five, six, seven, eight, nine, or ten amino acid motifs selected from: (a) $FX^3M$ (SEQ ID NO:16) or $VFX^3MA$ (SEQ ID NO:17), (b) $X^4FPX^5$ (SEQ ID NO:18), (c) $VX^6M$ (SEQ ID NO:19) or $KVX^6MT$ (SEQ ID NO:20), (d) $FX^7E$ (SEQ ID NO:21) or $YFX^7EL$ (SEQ ID NO:22), (e) $FX^8V$ (SEQ ID NO:23) or $SFX^8VY$ (SEQ ID NO:24), (f) $VX^9S$ (SEQ ID NO:25) or $AVX^9SN$ (SEQ ID NO:26), (g) $RX^{10}X^{11}V$ (SEQ ID NO:27), (h) $GX^{12}X^{13}Y$ (SEQ ID NO:28), (i) $X^{14}X^{15}R$ (SEQ ID NO:29) or $DX^{14}X^{15}R$ (SEQ ID NO:30) and (j) $AX^{16}D$ (SEQ ID NO:31) or $KAX^{16}D$ (SEQ ID NO:32), wherein $X^3$-$X^{16}$ are as described herein.

Optionally, the non-natural prenyltransferase of the disclosure can further include, in addition to the one or more variant amino acids as described herein, one or more amino acid variations at positions selected from: F211N, F211S, A230S, G284S, and Y286N, relative to SEQ ID NO:1; or F213N, F213S, A232S, G286S, and Y288N, relative to SEQ ID NO:2. See, for example, Valliere, M. A., et al. (2019) Nature Communications, 10; 565.

Site-directed mutagenesis or sequence alteration (e.g., site-specific mutagenesis or oligonucleotide-directed) can be used to make specific changes to a target prenyltransferase DNA sequence to provide a variant DNA sequence encoding prenyltransferase with the desired amino acid substitution. As a general matter, an oligonucleotide having a sequence that provides a codon encoding the variant amino acid is used. Alternatively, artificial gene sequence of the entire coding region of the variant prenyltransferase DNA sequence can be performed as preferred prenyltransferase targeted for substitution are generally less than 400 amino acids long.

Exemplary techniques using mutagenic oligonucleotides for generation of a variant prenyltransferase sequence include the Kunkel method which may utilize a prenyltransferase gene sequence placed into a phagemid. The phagemid in *E. coli* produces prenyltransferase ssDNA which is the template for mutagenesis using an oligonucleotide which is a primer extended on the template.

Depending on the restriction enzyme sites flanking a location of interest in the prenyltransferase DNA, cassette mutagenesis may be used to create a variant sequence of interest. For cassette mutagenesis, a DNA fragment is synthesized inserted into a plasmid, cleaved with a restriction enzyme, and then subsequently ligated to a pair of complementary oligonucleotides containing the prenyltransferase variant mutation. The restriction fragments of the plasmid and oligonucleotide can be ligated to one another.

Another technique that can be used to generate the variant prenyltransferase sequence is PCR site directed mutagenesis. Mutageneic oligonucleotide primers are used to introduce the desired mutation and to provide a PCR fragment carrying the mutated sequence. Additional oligonucleotides may be used to extend the ends of the mutated fragment to provide restriction sites suitable for restriction enzyme digestion and insertion into the gene.

Commercial kits for site-directed mutagenesis techniques are also available. For example, the Quikchange™ kit uses complementary mutagenic primers to PCR amplify a gene region using a high-fidelity non-strand-displacing DNA polymerase such as pfu polymerase. The reaction generates a nicked, circular DNA which is relaxed. The template DNA is eliminated by enzymatic digestion with a restriction enzyme such as DpnI which is specific for methylated DNA.

An expression vector or vectors can be constructed to include one or more variant prenyltransferase encoding nucleic acids as exemplified herein operably linked to expression control sequences functional in the host organism. Expression vectors applicable for use in the microbial host organisms provided include, for example, plasmids, phage vectors, viral vectors, episomes and artificial chromosomes, including vectors and selection sequences or markers operable for stable integration into a host chromosome. Additionally, the expression vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

The term "exogenous" is intended to mean that the referenced molecule or the referenced activity is introduced into the host microbial organism. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acid that expresses the referenced activity following introduction into the host microbial organism. Therefore, the term "endogenous" refers to a referenced molecule or activity that is present in the host. Similarly, the term when used in reference to expression of an encoding nucleic acid refers to expression of an encoding nucleic acid contained within the microbial organism. The term "heterologous" refers to a molecule or activity derived from a source other than the referenced species whereas "homologous" refers to a molecule or activity derived from the host microbial organism. Accordingly, exogenous expression of an encoding nucleic acid can utilize either or both a heterologous or homologous encoding nucleic acid.

It is understood that when more than one exogenous nucleic acid is included in a microbial organism, the more than one exogenous nucleic acid(s) refers to the referenced encoding nucleic acid or biosynthetic activity, as discussed above. It is further understood, as disclosed herein, that more than one exogenous nucleic acid(s) can be introduced into the host microbial organism on separate nucleic acid molecules, on polycistronic nucleic acid molecules, or a combination thereof, and still be considered as more than one exogenous nucleic acid. For example, as disclosed herein a microbial organism can be engineered to express two or more exogenous nucleic acids encoding a desired pathway enzyme or protein. In the case where two exogenous nucleic acids encoding a desired activity are introduced into a host microbial organism, it is understood that the two exogenous nucleic acids can be introduced as a single nucleic acid, for example, on a single plasmid, on separate plasmids, can be integrated into the host chromosome at a single site or multiple sites, and still be considered as two exogenous nucleic acids. Similarly, it is understood that more than two exogenous nucleic acids can be introduced into a host organism in any desired combination, for example, on a single plasmid, on separate plasmids, can be integrated into the host chromosome at a single site or multiple sites, and still be considered as two or more exogenous nucleic acids, for example three exogenous nucleic acids. Thus, the number of referenced exogenous nucleic acids or biosynthetic activities refers to the number of encoding nucleic acids or the number of biosynthetic activities, not the number of separate nucleic acids introduced into the host organism.

Exogenous variant prenyltransferase-encoding nucleic acid sequences can be introduced stably or transiently into a host cell using techniques well known in the art including, but not limited to, conjugation, electroporation, chemical transformation, transduction, transfection, and ultrasound transformation. Optionally, for exogenous expression in *E. coli* or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. For example, removal of a mitochondrial leader sequence led to increased expression in *E. coli* (Hoffmeister et al., *J. Biol. Chem.* 280:4329-4338 (2005)). For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. Thus, it is understood that appropriate modifications to a nucleic acid sequence to remove or include a targeting sequence can be incorporated into an exogenous nucleic acid sequence to impart desirable properties. Furthermore, genes can be subjected to codon optimization with techniques well known in the art to achieve optimized expression of the proteins.

The terms "microbial," "microbial organism" or "microorganism" are intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

The term "isolated" when used in reference to a microbial organism is intended to mean an organism that is substantially free of at least one component that the referenced microbial organism is found with in nature. The term includes a microbial organism that is removed from some or all components as it is found in its natural environment. The term also includes a microbial organism that is removed from some or all components as the microbial organism is found in non-naturally occurring environments.

In some aspects the prenyltransferase variant gene is introduced into a cell with a gene disruption. The term "gene disruption," or grammatical equivalents thereof, is intended to mean a genetic alteration that renders the encoded gene product inactive or attenuated. The genetic alteration can be, for example, deletion of the entire gene, deletion of a regulatory sequence required for transcription or translation, deletion of a portion of the gene which results in a truncated gene product, or by any of various mutation strategies that inactivate or attenuate the encoded gene product. One particularly useful method of gene disruption is complete gene deletion because it reduces or eliminates the occurrence of genetic reversions. The phenotypic effect of a gene disruption can be a null mutation, which can arise from many types of mutations including inactivating point mutations, entire gene deletions, and deletions of chromosomal segments or entire chromosomes. Specific antisense nucleic acid compounds and enzyme inhibitors, such as antibiotics, can also produce null mutant phenotype, therefore being equivalent to gene disruption.

A metabolic modification refers to a biochemical reaction that is altered from its naturally occurring state. Therefore, microorganisms may have genetic modifications to nucleic acids encoding metabolic polypeptides, or functional fragments thereof. Exemplary metabolic modifications are disclosed herein.

The microorganisms provided herein can contain stable genetic alterations, which refers to microorganisms that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely.

Those skilled in the art will understand that the genetic alterations, including metabolic modifications exemplified herein, are described with reference to a suitable host organism such as *E. coli* and their corresponding metabolic reactions or a suitable source organism for desired genetic material such as genes for a desired metabolic pathway. However, given the complete genome sequencing of a wide variety of organisms and the high level of skill in the area of genomics, those skilled in the art will readily be able to apply the teachings and guidance provided herein to essentially all other organisms. For example, the *E. coli* metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

A variety of microorganism may be suitable for incorporating the variant prenyltransferase, optionally with one or more other transgenes. Such organisms include both prokaryotic and eukaryotic organisms including, but not limited to, bacteria, including archaea and eubacteria, and eukaryotes, including yeast, plant, insect, animal, and mammal, including human. Exemplary species are reported in U.S. application Ser. No. 13/975,678 (filed Aug. 26, 2013), which is incorporated herein by reference, and include, for example, *Escherichia coli, Saccharomyces cerevisiae, Saccharomyces kluyveri, Candida boidinii, Clostridium kluyveri, Clostridium acetobutylicum, Clostridium beijerinckii, Clostridium saccharoperbutylacetonicum, Clostridium perfringens, Clostridium difficile, Clostridium botulinum, Clostridium tyrobutyricum, Clostridium tetanomorphum, Clostridium tetani, Clostridium propionicum, Clostridium aminobutyricum, Clostridium subterminale, Clostridium sticklandii, Ralstonia eutropha, Mycobacterium bovis, Mycobacterium tuberculosis, Porphyromonas gingivalis, Arabidopsis thaliana, Thermus thermophilus, Pseudomonas* species, including *Pseudomonas aeruginosa, Pseudomonas putida, Pseudomonas stutzeri, Pseudomonas fluorescens, Homo sapiens, Oryctolagus cuniculus, Rhodobacter spaeroides, Thermoanaerobacter brockii, Metallosphaera sedula, Leuconostoc mesenteroides, Chloroflexus aurantiacus, Roseiflexus castenholzii, Erythrobacter, Simmondsia chinensis, Acinetobacter* species, including *Acinetobacter calcoaceticus* and *Acinetobacter baylyi, Porphyromonas gingivalis, Sulfolobus tokodaii, Sulfolobus solfataricus, Sulfolobus acidocaldarius, Bacillus subtilis, Bacillus cereus, Bacillus megaterium, Bacillus brevis, Bacillus pumilus, Rattus norvegicus, Klebsiella pneumonia, Klebsiella oxytoca, Euglena gracilis, Treponema denticola, Moorella thermoacetica, Thermotoga maritima, Halobacterium salinarum, Geobacillus stearothermophilus, Aeropyrum pernix, Sus scrofa, Caenorhabditis elegans, Corynebacterium glutamicum, Acidaminococcus fermentans, Lactococcus lactis, Lactobacillus plantarum, Streptococcus thermophilus, Enterobacter aerogenes, Candida, Aspergillus terreus, Pedicoccus pentosaceus, Zymomonas mobilus, Acetobacter pasteurians, Kluyveromyces lactis, Eubacterium barkeri, Bacteroides capillosus, Anaerotruncus colihominis, Natranaerobius thermophilusm, Campylobacter jejuni, Haemophilus influenzae, Serratia marcescens, Citrobacter amalonaticus, Myxococcus xanthus, Fusobacterium nuleatum, Penicillium chrysogenum*, marine gamma proteobacterium, butyrate-producing bacterium, *Nocardia iowensis, Nocardia farcinica, Streptomyces griseus, Schizosaccharomyces pombe, Geobacillus thermoglucosidasius, Salmonella typhimurium, Vibrio cholera, Heliobacter pylori, Nicotiana tabacum, Oryza sativa, Haloferax mediterranei, Agrobacterium tumefaciens, Achromobacter denitrificans, Fusobacterium nucleatum, Streptomyces clavuligenus, Acinetobacter baumanii, Mus musculus, Lachancea kluyveri, Trichomonas vaginalis, Trypanosoma brucei, Pseudomonas stutzeri, Bradyrhizobium japonicum, Mesorhizobium loti, Bos taurus, Nicotiana glutinosa, Vibrio vulnficus, Selenomonas ruminantium, Vibrio parahaemolyticus, Archaeoglobus fulgidus, Haloarcula marismortui, Pyrobaculum aerophilum, Mycobacterium smegmatis* MC2 155, *Mycobacterium avium* subsp. paratuberculosis K-10, *Mycobacterium marinum* M, *Tsukamurella paurometabola* DSM 20162, Cyanobium PCC7001, *Dictyostelium discoideum* AX4, as well as other exemplary species disclosed herein or available as source organisms for corresponding genes.

In certain embodiments, suitable organisms include *Acinetobacter baumannii* Naval-82, *Acinetobacter* sp. ADP1, *Acinetobacter* sp. strain M-1, *Actinobacillus succinogenes* 130Z, *Allochromatium vinosum* DSM 180, *Amycolatopsis methanolica, Arabidopsis thaliana, Atopobium parvulum* DSM 20469, *Azotobacter vinelandii* DJ, *Bacillus alcalophilus* ATCC 27647, *Bacillus azotoformans* LMG 9581, *Bacillus coagulans* 36D1, *Bacillus megaterium, Bacillus methanolicus* MGA3, *Bacillus methanolicus* PB1, *Bacillus methanolicus* PB-1, *Bacillus selenitireducens* MLS10, *Bacillus smithii, Bacillus subtilis, Burkholderia cenocepacia, Burkholderia cepacia, Burkholderia multivorans, Burkholderia pyrrocinia, Burkholderia stabilis, Burkholderia thailandensis* E264, Burkholderiales bacterium Joshi_001, Butyrate-producing bacterium L2-50, *Campylobacter jejuni, Candida albicans, Candida boidinii, Candida methylica, Carboxydothermus hydrogenoformans, Carboxydothermus hydrogenoformans* Z-2901, *Caulobacter* sp. AP07, *Chloroflexus aggregans* DSM 9485, *Chloroflexus aurantiacus* J-10-fl, *Citrobacter freundii, Citrobacter koseri* ATCC BAA-895, *Citrobacter youngae, Clostridium, Clostridium acetobutylicum, Clostridium acetobutylicum* ATCC 824, *Clostridium acidurici, Clostridium aminobutyricum, Clostridium asparagiforme* DSM 15981, *Clostridium beijerinckii, Clostridium beijerinckii* NCIMB 8052, *Clostridium bolteae* ATCC BAA-613, *Clostridium carboxidivorans* P7, *Clostridium cellulovorans* 743B, *Clostridium difficile, Clostridium hiranonis* DSM 13275, *Clostridium hylemonae* DSM 15053, *Clostridium kluyveri, Clostridium kluyveri* DSM 555, *Clostridium* ljungdahli, *Clostridium ljungdahlii* DSM 13528, *Clostridium methylpentosum* DSM 5476, *Clostridium pasteurianum, Clostridium pasteurianum* DSM 525, *Clostridium perfringens, Clostridium perfringens*

ATCC 13124, *Clostridium perfringens* str. 13, *Clostridium phytofermentans* ISDg, *Clostridium saccharobutylicum, Clostridium saccharoperbutylacetonicum, Clostridium saccharoperbutylacetonicum* N1-4, *Clostridium tetani, Corynebacterium glutamicum* ATCC 14067, *Corynebacterium glutamicum* R, *Corynebacterium* sp. U-96, *Corynebacterium variabile, Cupriavidus necator* N-1, Cyanobium PCC7001, *Desulfatibacillum alkenivorans* AK-01, *Desulfitobacterium hafniense, Desulfitobacterium metallireducens* DSM 15288, *Desulfotomaculum reducens* MI-1, *Desulfovibrio africanus* str. Walvis Bay, *Desulfovibrio* fructosovorans JJ, *Desulfovibrio vulgaris* str. Hildenborough, *Desulfovibrio vulgaris* str. 'Miyazaki F', *Dictyostelium discoideum* AX4, *Escherichia coli, Escherichia coli* K-12, *Escherichia coli* K-12 MG1655, *Eubacterium hallii* DSM 3353, *Flavobacterium frigoris, Fusobacterium nucleatum* subsp. *polymorphum* ATCC 10953, *Geobacillus* sp. Y4.1MC1, *Geobacillus* themodenitrifcans NG80-2, *Geobacter bemidjiensis* Bem, *Geobacter sulfurreducens, Geobacter sulfurreducens* PCA, *Geobacillus stearothermophilus* DSM 2334, *Haemophilus influenzae, Helicobacter pylori, Homo sapiens, Hydrogenobacter thermophilus, Hydrogenobacter thermophilus* TK-6, *Hyphomicrobium denitrificans* ATCC 51888, *Hyphomicrobium zavarzinii, Klebsiella pneumoniae, Klebsiella pneumoniae* subsp. *pneumoniae* MGH 78578, *Lactobacillus brevis* ATCC 367, *Leuconostoc mesenteroides, Lysinibacillus fusiformis, Lysinibacillus sphaericus, Mesorhizobium loti* MAFF303099, *Metallosphaera sedula, Methanosarcina acetivorans, Methanosarcina acetivorans* C2A, *Methanosarcina barkeri, Methanosarcina mazei* Tuc01, *Methylobacter marinus, Methylobacterium extorquens, Methylobacterium extorquens* AM1, *Methylococcus* capsulatas, *Methylomonas* aminofaciens, *Moorella* thermoacetica, Mycobacter sp. strain JC1 DSM 3803, *Mycobacterium avium* subsp. paratuberculosis K-10, *Mycobacterium bovis* BCG, *Mycobacterium gastri, Mycobacterium marinum* M, *Mycobacterium smegmatis, Mycobacterium smegmatis* MC2 155, *Mycobacterium tuberculosis, Nitrosopumilus salaria* BD31, Nitrososphaera gargensis Ga9.2, *Nocardia farcinica* IFM 10152, *Nocardia* iowensis (sp. NRRL 5646), *Nostoc* sp. PCC 7120, *Ogataea angusta, Ogataea parapolymorpha* DL-1 (*Hansenula polymorpha* DL-1), *Paenibacillus peoriae* KCTC 3763, *Paracoccus denitrificans, Penicillium chrysogenum, Photobacterium profundum* 3TCK, *Phytofermentans* ISDg, *Pichia pastoris, Picrophilus torridus* DSM9790, *Porphyromonas gingivalis, Porphyromonas gingivalis* W83, *Pseudomonas aeruginosa* PA01, *Pseudomonas denitrificans, Pseudomonas knackmussii, Pseudomonas putida, Pseudomonas* sp, *Pseudomonas syringae* pv. *syringae* B728a, *Pyrobaculum islandicum* DSM 4184, *Pyrococcus abyssi, Pyrococcus furiosus, Pyrococcus horikoshii* OT3, *Ralstonia eutropha, Ralstonia eutropha* H16, *Rhodobacter capsulatus, Rhodobacter sphaeroides, Rhodobacter sphaeroides* ATCC 17025, *Rhodopseudomonas palustris, Rhodopseudomonas palustris* CGA009, *Rhodopseudomonas palustris* DX-1, *Rhodospirillum rubrum, Rhodospirillum rubrum* ATCC 11170, Ruminococcus obeum ATCC 29174, *Saccharomyces cerevisiae, Saccharomyces cerevisiae* S288c, *Salmonella enterica, Salmonella enterica* subsp. *enterica* serovar *Typhimurium* str. LT2, *Salmonella enterica typhimurium, Salmonella typhimurium, Schizosaccharomyces pombe, Sebaldella termitidis* ATCC 33386, *Shewanella oneidensis* MR-4, *Sinorhizobium meliloti* 1021, *Streptomyces coelicolor, Streptomyces griseus* subsp. *griseus* NBRC 13350, *Sulfolobus* acidocalarius, *Sulfolobus solfataricus* P-2, *Synechocystis str. PCC* 6803, *Syntrophobacter fumaroxidans, Thauera aromatica, Thermoanaerobacter* sp. X514, *Thermococcus kodakaraensis, Thermococcus litoralis, Thermoplasma acidophilum, Thermoproteus neutrophilus, Thermotoga maritima, Thiocapsa roseopersicina, Tolumonas auensis* DSM9187, *Trichomonas vaginalis* G3, *Trypanosoma brucei, Tsukamurella paurometabola* DSM 20162, *Vibrio cholera, Vibrio harveyi* ATCC BAA-1116, *Xanthobacter autotrophicus* Py2, *Yersinia intermedia*, or *Zea mays.*

Figure 2:
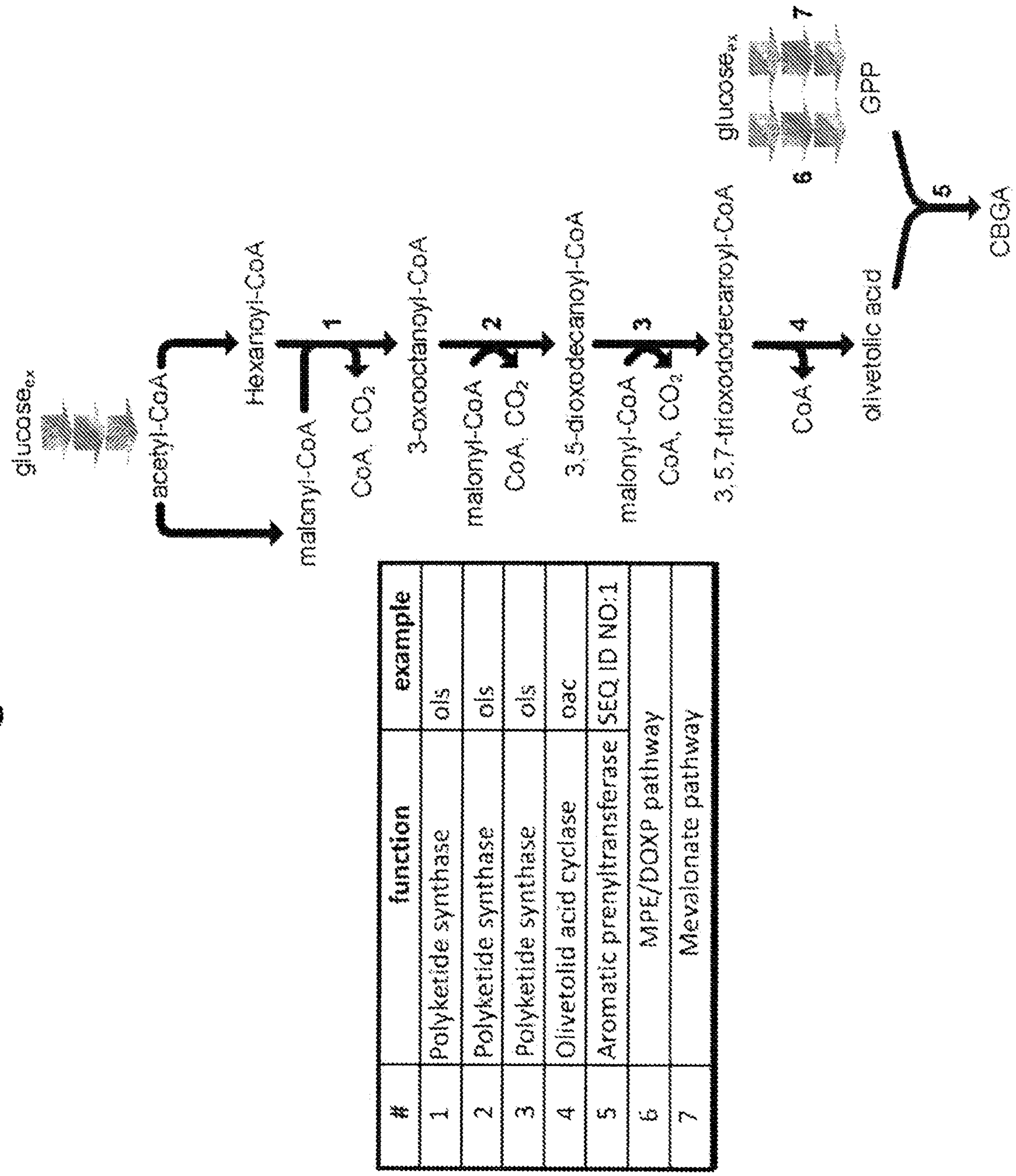
FIG. 2 is diagram of exemplary metabolic pathways showing 3-GOLA formation from hexanoyl-CoA and geranyl diphosphate.

FIG. 2 shows exemplary pathways to CBGA formation from hexanoyl-CoA, and geranyl diphosphate. In some cases, the engineered cell of the disclosure can utilize hexanoyl-CoA that is produced from a cellular fatty acid biosynthesis pathway. For example, hexanoyl-CoA can be formed endogenously via reverse beta-oxidation of fatty acids.

In other embodiments, the engineered cell can further include hexanoyl-CoA synthetase, such as expressed on a transgene. Exemplary hexanoyl-CoA synthetase genes include enzymes endogenous to bacteria, including *E. coli*, as well as eukaryotes, including yeast and *C. sativa* (see for example Stout et al., Plant J., 2012; 71:353-365).

FIG. 2 also shows pathway formation of malonyl-CoA, which is used for the formation of olivetolic acid along with hexanoyl-CoA. Endogenous malonyl-CoA formation can be supplemented by formation from acetyl CoA using overexpression of acetyl-CoA carboxylase. Accordingly, the engineered cell can further include acetyl-CoA carboxylase, such as expressed on a transgene or integrated into the genome.

Acetyl-CoA carboxylase (EC 6.4.1.2) catalyzes the ATP-dependent carboxylation of acetyl-CoA to malonyl-CoA. This enzyme is biotin dependent and is the first reaction of fatty acid biosynthesis initiation in several organisms. Exemplary enzymes are encoded by accABCD of *E. coli* (Davis et al, *J Biol Chem* 275:28593-8 (2000)), ACC1 of *Saccharomyces cerevisiae* and homologs (Sumper et al, *Methods Enzym* 71:34-7 (1981)).

| Protein | GenBank ID | GI Number | Organism |
|---|---|---|---|
| ACC1 | CAA96294.1 | 1302498 | *Saccharomyces cerevisiae* |
| KLLA0F06072g | XP_455355.1 | 50310667 | *Kluyveromyces lactis* |
| ACC1 | XP_718624.1 | 68474502 | *Candida albicans* |
| YALI0C11407p | XP_501721.1 | 50548503 | *Yarrowia lipolytica* |
| ANI_1_1724104 | XP_001395476.1 | 145246454 | *Aspergillus niger* |
| accA | AAC73296.1 | 1786382 | *Escherichia coli* |
| accB | AAC76287.1 | 1789653 | *Escherichia coli* |
| accC | AAC76288.1 | 1789654 | *Escherichia coli* |
| accD | AAC75376.1 | 1788655 | *Escherichia coli* |

FIG. 2 also shows polyketide synthase converts hexanoyl-CoA to olivetolic acid through poly-p-keto intermediates. Accordingly, the engineered cell can further include polyketide synthase, such as expressed on a transgene or integrated into the genome. The engineered cell can further include olivetolic acid cyclase (oac), to convert 3,5,7-trioxododecanoyl-CoA to olivetolic acid.

In some embodiments, the engineered cell preferentially uses a 5-alkylbenzene-1,3-diol as an (alcohol) substrate instead of an acid derivative of an alkylbenzene-1,3-diol. The 5-alkylbenzene-1,3-diol can be reacted with GPP to form a 2-prenylated 5-alkylbenzene-1,3-diol. For example, reaction of olivetol and GPP promoted with the non-natural prenyltransferase variants of the disclosure can form cannabigerol (CBG; 2-GOL). Accordingly, formation of the acid derivative of an alkylbenzene-1,3-diol can be avoided in cell To avoid formation of the acid derivative, the olivetolic acid cyclase (oac) gene can be excluded from the pathway, or can be deleted from the cell. Gagne, S. J. et al (PNAS, 109:12811-12816, 2012) describes a pathways utilizing hexanoyl-CoA which can be converted to olivetol using tetraketide synthase (TKS), or further to olivetolic acid by action of olivetolic acid cyclase (oac).

Optionally, the engineered cell can include one or more exogenous genes which allow the cell to grow on carbon sources the cell would not normally metabolize, or one or more exogenous genes or modifications to endogenous genes that allow the cell to have improved growth on carbon sources the cell normally uses. For example, WO2015/051298 (MDH variants) and WO2017/075208 (MDH fusions) describe genetic modifications that provide pathways allowing to cell to grow on methanol; WO2009/094485 (syngas) describes genetic modifications that provide pathways allowing to cell to grow on synthesis gas.

As used herein, the term "bioderived" means derived from or synthesized by a biological organism and can be considered a renewable resource since it can be generated by a biological organism. Such a biological organism, in particular the microbial organisms disclosed herein, can utilize feedstock or biomass, such as, sugars or carbohydrates obtained from an agricultural, plant, bacterial, or animal source. Alternatively, the biological organism can utilize atmospheric carbon. As used herein, the term "biobased" means a product as described above that is composed, in whole or in part, of a bioderived compound of the disclosure. A biobased or bioderived product is in contrast to a petroleum derived product, wherein such a product is derived from or synthesized from petroleum or a petrochemical feedstock.

Depending on the desired microorganism or strain to be used, the appropriate culture medium may be used. For example, descriptions of various culture media may be found in "Manual of Methods for General Bacteriology" of the American Society for Bacteriology (Washington D.C., USA, 1981). As used here, "medium" as it relates to the growth source refers to the starting medium be it in a solid or liquid form. "Cultured medium", on the other hand and as used here refers to medium (e.g. liquid medium) containing microbes that have been fermentatively grown and can include other cellular biomass. The medium generally includes one or more carbon sources, nitrogen sources, inorganic salts, vitamins and/or trace elements.

Exemplary carbon sources include sugar carbons such as sucrose, glucose, galactose, fructose, mannose, isomaltose, xylose, pannose, maltose, arabinose, cellobiose and 3-, 4-, or 5-oligomers thereof. Other carbon sources include alcohol carbon sources such as methanol, ethanol, glycerol, formate and fatty acids. Still other carbon sources include carbon sources from gas such as synthesis gas, waste gas, methane, CO, $CO_2$ and any mixture of CO, $CO_2$ with $H_2$. Other carbon sources can include renewal feedstocks and biomass. Exemplary renewal feedstocks include cellulosic biomass, hemicellulosic biomass and lignin feedstocks.

In some embodiments, culture conditions include anaerobic or substantially anaerobic growth or maintenance conditions. Exemplary anaerobic conditions have been described previously and are well known in the art. Exemplary anaerobic conditions for fermentation processes are disclosed, for example, in U.S. Patent Application Publication No 2009/0047719, filed Aug. 10, 2007. Any of these conditions can be employed with the microbial organisms as well as other anaerobic conditions well known in the art.

The culture conditions can include, for example, liquid culture procedures as well as fermentation and other large scale culture procedures. Useful yields of the products can be obtained under anaerobic or substantially anaerobic culture conditions.

An exemplary growth condition for achieving, one or more cannabinoid product(s) includes anaerobic culture or fermentation conditions. In certain embodiments, the microbial organism can be sustained, cultured or fermented under anaerobic or substantially anaerobic conditions. Briefly, anaerobic conditions refer to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases.

The culture conditions can be scaled up and grown continuously for manufacturing cannabinoid product. Exemplary growth procedures include, for example, fed-batch fermentation and batch separation; fed-batch fermentation and continuous separation, or continuous fermentation and continuous separation. All of these processes are well known in the art. Fermentation procedures are particularly useful for the biosynthetic production of commercial quantities of cannabinoid product. Generally, and as with non-continuous culture procedures, the continuous and/or near-continuous production of cannabinoid product will include culturing a cannabinoid producing organism on sufficient nutrients and medium to sustain and/or nearly sustain growth in an exponential phase. Continuous culture under such conditions can include, for example, 1 day, 2, 3, 4, 5, 6 or 7 days or more. Additionally, continuous culture can include 1 week, 2, 3, 4 or 5 or more weeks and up to several months. Alternatively, the desired microorganism can be cultured for hours, if suitable for a particular application. It is to be understood that the continuous and/or near-continuous culture conditions also can include all time intervals in between these exemplary periods. It is further understood that the time of culturing the microbial organism is for a sufficient period of time to produce a sufficient amount of product for a desired purpose.

Fermentation procedures are well known in the art. Briefly, fermentation for the biosynthetic production of cannabinoid product can be utilized in, for example, fed-batch fermentation and batch separation; fed-batch fermentation and continuous separation, or continuous fermentation and continuous separation. Examples of batch and continuous fermentation procedures are well known in the art.

The culture medium at the start of fermentation may have a pH of about 5 to about 7. The pH may be less than 11, less than 10, less than 9, or less than 8. In other embodiments the pH may be at least 2, at least 3, at least 4, at least 5, at least 6, or at least 7. In other embodiments, the pH of the medium may be about 6 to about 9.5; 6 to about 9, about 6 to 8 or about 8 to 9.

Suitable purification and/or assays to test, e.g., for the production of 3-geranyl-olivetolate can be performed using well known methods. Suitable replicates such as triplicate cultures can be grown for each engineered strain to be tested. For example, product and byproduct formation in the engineered production host can be monitored. The final product and intermediates, and other organic compounds, can be analyzed by methods such as HPLC (High Performance Liquid Chromatography), GC-MS (Gas Chromatography- Mass Spectroscopy) and LC-MS (Liquid Chromatography-Mass Spectroscopy) or other suitable analytical methods using routine procedures well known in the art. The release of product in the fermentation broth can also be tested with the culture supernatant. Byproducts and residual glucose can be quantified by HPLC using, for example, a refractive index detector for glucose and alcohols, and a UV detector for organic acids (Lin et al., *Biotechnol. Bioeng.* 90:775-779 (2005)), or other suitable assay and detection methods well known in the art. The individual enzyme or protein activities from the exogenous DNA sequences can also be assayed using methods well known in the art.

The 3-geranyl-olivetolate (CBGA) or other target molecules may be separated from other components in the culture using a variety of methods well known in the art. Such separation methods include, for example, extraction procedures as well as methods that include continuous liquid-liquid extraction, pervaporation, evaporation, filtration, membrane filtration (including reverse osmosis, nanofiltration, ultrafiltration, and microfiltration), membrane filtration with diafiltration, membrane separation, reverse osmosis, electrodialysis, distillation, extractive distillation, reactive distillation, azeotropic distillation, crystallization and recrystallization, centrifugation, extractive filtration, ion exchange chromatography, size exclusion chromatography, adsorption chromatography, carbon adsorption, hydrogenation, and ultrafiltration. All of the above methods are well known in the art.

In view of the regioselectivity of the prenyltransferase variants, the disclosure also provides compositions that are enriched for desired cannabinoids and derivatives thereof. In particular, the disclosure provides compositions enriched for CBGA (3-geranyl-olivetolate (3-GOLA)) and/or CBG compared to the undesired isomer, e.g. 5-GOLA or 4-GOL (decarboxylated 5-GOLA). Such enriched compositions include those that are pharmaceutical compositions as well as those that are used for non-pharmaceutical purposes, including medicinal purposes. Accordingly, in some embodiments, provided are compositions, such as pharmaceutical compositions or medicinal compositions, with CBGA and/or CBG that are 90% or greater, 91% or greater, 92% or greater, 93% or greater, 94% or greater, 95% or greater, 96% or greater, 97% or greater, 98% or greater, 99% or greater, 99.2% or greater, 99.4% or greater, 99.5% or greater, 99.6% or greater, 99.7% or greater, 99.8% or greater, 99.9% or greater, 99.95% or greater or even 100% 3-geranyl-olivetolate (3-GOLA) or its decarboxylated derivative CBG (2-GOL), of all geranyl-olivetolate compounds, including 5-GOLA and 4-GOL compounds, which can be less desirable when present in various compositions.

Examples

Library Constructs and Strains

Mutant variants of prenyltransferase were constructed as libraries on plasmid by single-site and multi-site (combinatorial) mutagenesis methods, using specific primers at the positions undergoing mutagenesis, amplifying fragments via PCR, and circularizing plasmid via Gibson ligation. A compressed-codon approach was used to eliminate codon redundancy to lower library size. Plasmid used was the pCDFDuet-1 vector (Novagen), with expression of the prenyltransferase gene under control of a T7 promoter and lac operator. The resulting prenyltransferase protein includes a fusion to a 6×Histidine tag at the N-terminus. Active variants were identified to activity assay described below and sequenced. Plasmids harboring the mutant libraries of prenyltransferase genes were transformed into *E. coli* strain BL21(DE3) and plated onto Agar plates with suitable antibiotic selection.

Cell Culture for Screening Homologs and Mutant Libraries

From both mutant library transformants and control transformants, single colonies were picked for growth into 96-well plates using Luria Bertani (LB) growth medium with spectomycin antibiotic. Following overnight growth, cultures were sub-cultured into fresh medium of LB with 1% glucose and antibiotic. After 4 hours growth, gene expression was induced by addition of IPTG, and cells pelleted after overnight growth at 30° C., and media discarded. Cells pellets were stored at −20° C. until ready for assay. Number of samples screened was approximately three times oversampling based on calculation of total possible variants.

High-Throughput Activity Assay

Cell pellets were thawed, and subjected to chemical lysis by BugBuster (Novagen) in the presence of protease inhibitor cocktail, 5 mM β-mercaptoethanol, and nuclease and lysozyme. Assays were performed in 96-well plates in a total volume of 40 μl in 50 mM HEPES, pH 7.5 buffer containing 1 mM geranyl pyrophosphate (Sigma-Aldrich) and 1 mM olivetolic acid (Santa Cruz Biotechnology) and 5 mM magnesium chloride. Reactions were initiated by addition of cell lysate then incubated for a measured period of up to 8 hours, quenched with acetonitrile to a final concentration of 65%, then centrifuged to pellet denatured protein. Supernatants were transferred to new 96-well plates for GCMS analysis of CBGA (3-GOLA).

LCMS Analysis of Prenyltransferase Activity in Cell Lysates or as Purified Enzymes CBGA (3-GOLA) and 5-GOLA were analyzed by LCMS or LCMS/MS methods using C18 reversed phase chromatography coupled to either Exactive (Thermofisher) or QTrap 4500 (Sciex) mass spectrometers.

Enzymatic reactions, whether conducted in cell lysate or using purified proteins, were first treated with 6 volumes of organic solvent (acetonitrile containing internal standards) to precipitate proteins, the supernatant was recovered and further diluted for LCMS analysis, if necessary.

High resolution LCMS analysis was conducted using Accela HPLC quaternary pump, Thermo PAL autosampler and Exactive high resolution accurate mass spectrometer. C18 Hypersil Gold column 50×3 mm, 1.9 um particle size, was used with water with 0.1% formic acid (mobile phase A) and acetonitrile with 0.1% formic acid (mobile phase B) at 300 uL/min flow rate at room temperature and mobile phase B gradient 50-95% in 5 min and 10 min total run time. Negative ionization mode was used for CBGA and 5-GOLA. CBGA and 5-GOLA isomer were well resolved with this chromatographic method (retention times 4.8 and 5.05 min, respectively) and enabled unambiguous quantification. High resolution MS signals were extracted using narrow ±5 ppm mass window around theoretical m/z. External neat calibration standards were used for quantification.

Identification of Homologs and Mutant Variants

Prenyltransferase homologs, found by BLAST search and rational approaches, were cloned and expressed in *E. coli*, and assayed in cell lysates for activity on OLA and GPP, using LCMS to detect CBGA or 5-GOLA, as described above. In in vitro assay using cell lysates, all homologs showed low, but measurable, activity and were non-regio-specific, showing mixed products of both 3-GOLA (CBGA) and 5-GOLA. Product was detected for prenyltransferases with SEQ ID NO:1 to SEQ ID NO:15. Activity was confirmed for selected homologs by assaying purified enzymes. N-terminal His-tagged homologs were purified using nickel affinity chromatography.

Using a prenyltransferase homolog template, site-saturation mutagenesis experiments were performed to identify amino acid positions that conferred improved activity towards formation of CBGA, as well as regioselectivity towards CBGA (3-GOLA) over the undesired product 5-GOLA. Results of these studies allowed identification of well-performing mutant variants having the amino acid substitutions including those shown in FIG. 6. (Using SEQ ID NO:1 as a reference template for amino acid position numbering purposes, the amino acid positions corresponding to the mutation locations are as follows: $X^3$=49; $X^4$=121; $X^5$=124; $X^6$=159; $X^7$=175; $X^8$=212; $X^9$=232; $X^{10}$=267; $X^{11}$=268; $X^2$=285; $X^{13}$=286; $X^{14}$=292; $X^{15}$=293; and $X^{16}$=300.)

Mutation at several residue positions results in very high regiospecificity towards CBGA, and combinatorial mutagenesis at selected residues with particular subsets of amino acids was performed to identify further unique combinatorial variants with enhanced activity and regioselectivity. 36 unique separate variants were identified with high activities, and with high regioselectivity for CBGA.

One particular mutant pair ($X^6$=H; X15=W) was introduced into a number of prenyltransferase homologs, resulting in multiple-fold improved activity compared to corresponding wild-type sequence and regioselectivity (as high as 100% regioselectivity) (e.g. SEQ ID NO: 1, 3, 4, 5, 7, 8, 13, 14, and 15). However, there was no improvement seen in SEQ ID NO: 6, 9, 10, 11, 12; this was interpreted as possibly due to an artefact of high expression leading to insolubility. This can be addressed, for example, with a weaker promoter, or a low copy vector, in plasmid construction.

Activities with Olivetolic Acid and its Analogs

Non-natural prenyltransferases generated by engineering mutations into various wild-type prenyltransferases or modified prenyltransferases were compared to a wild-type enzyme, e.g. SEQ ID NO:2, for activity with either olivetolic acid or olivetolic acid analogs, divarinolic acid and orsellinic acid, and co-substrate GPP. The non-natural prenyltransferases were expressed in *E. coli*, purified and assayed. Assay components were as follows: Reaction volume was 100 microliter (75 microliter substrate+25 microliter enzyme), 100 mM Tris HCl buffer, pH 7.5, 1 mM GPP, with 5 mM olivetolic acid, divarinolic acid, orsellinic acid or olivetol, and 5 mM MgCl2, 25 microliter enzyme. Reaction occurred for 60 minutes at 22 degrees C. A 40 microliter aliquot of the reaction was removed and quenched with 360 microliters of 75% acetonitrile with 1% formic acid plus two internal standards. After centrifugation to remove any particles, samples were analyzed. Compounds were identified by their LC retention times and MRM transitions specific to the compounds. LCMSMS analysis was conducted on Shimadzu UHPLC system coupled with AB Sciex QTRAP4500 mass spectrometer. Agilent Eclipse XDB C18 column (4.6×3.0 mm, 1.8 um) was used with 1-2 min gradient elution at 1 mL/min using water containing 0.1% ammonia acetate as mobile phase A and 90% methanol containing 0.1% ammonia acetate as mobile phase B. The LC column temperature was maintained at 45° C. Negative ionization mode was used for all the analytes including CBGA, CBGVA, CBGOA, CBG and their isomers, as well as OLA, PDAL, OL and hexanoic acid. The isomer pairs were resolved with appropriate gradient elution. Products determined included cannabigerolic acid (CBGA, 3-GOLA) or its 5-GOLA isomer, cannabigerovarinic acid (CBGVA, 3-GDVA) or its 5-GDVA isomer, cannabigerorcinic acid (CBGOA, 3-GOSA) or its 5-GOSA isomer and cannabigerol (CBG, 2-GOL) or its 4-GOL isomer. The enzymes were active even after 1 year of storage.

The results with the acid substrates are shown in the following Table 1 as relative fold increase over production by wild-type enzyme.

TABLE 1

| | | Substrate | | | |
|---|---|---|---|---|---|
| | | Olivetolic acid | Divarinolic acid | Orsellinic acid | Orsellinic acid |
| | | Product | | | |
| NphB variant | Mutations | CBGA 3-GOLA Relative fold increase | CBGVA 3-GDVA Relative fold increase | CBGOA 3-GOSA Relative fold increase | CBGOA 5-GOSA Relative fold increase |
| Seq1C | Q159S S212H Y286V | 67 | 328.6 | 516.6 | 0 |
| Seq1D | Q161S S214H Y288V and GS insertion at position 45 | 72 | 356.7 | 466.8 | 0 |
| Seq1B | Q159H Q293W | 48 | 105.6 | 132.7 | 32.0 |
| Seq2H | Q161R Q295V | 10 | 19.6 | 9.2 | 0.6 |
| Seq2J | S214H | 9 | 5.7 | 28.7 | 0.9 |
| Seq2J | Q161H | 28 | 37.8 | 53.1 | 25.2 |
| Seq2B | Y288V | 10 | 16.5 | 17.3 | 0.4 |
| Seq2M | Q161H Q295W | 84 | 330.6 | 206.2 | 34.1 |
| Seq2DN | Q161S S214H Y288V | 86 | 371.4 | 364.9 | 0 |
| Seq2CP | Y288I | 48 | 104.4 | 53.6 | 0.6 |
| Seq1C | Q159S S212H Y286V | 67 | 328.6 | 516.6 | 0 |
| Seq1D | Q161S S214H Y288V and GS insertion at position 45 | 72 | 356.7 | 466.8 | 0 |
| Seq1B | Q159H Q293W Q295V | 48 | 105.6 | 132.7 | 32.0 |
| Seq2CQ | Q161H Y288I Q295W | 80 | 291.3 | 100.7 | 1.1 |
| Seq2CS | Q161H Y288V Q295M | 53 | 137.7 | 18.1 | 0.4 |
| Seq2CV | Q161H Q295V | 85 | 127.4 | 84.6 | 6.8 |

In the above table and in the following table all of the non-natural prenyltransferases designated as "Seq1x" are based on SEQ TD NO:1 and those designated "Seq2x" are based on SEQ ID NO:2. The mutant designated Seq1D is identical to Seq1C (both based on SEQ TD NO: 1) but for the glycine-serine insertions at position 45, which resulted in a shift in position numbering. The wild-type enzyme produced a mix of 3-GOLA and 5-GOLA. Decarboxylation of this mixture would result in a composition containing a mixture of CBG (2-GOL) with the less desired 4-GOL isomer. The non-natural prenyltransferases were all superior to wild-type enzyme in amount of desired cannabinoid produced over time, e.g. CBGA, CBGVA and CBGOA. In addition, the non-natural prenyltransferases did not produce the undesirable 5-GOLA or 3-GDVA isomers. These unique compositions provide a further advantage that subsequent steps to purify the cannabinoid can avoid an isomer separation step. Decarboxylation of the mixtures would result in a composition containing desired product CBG (2-GOL) without the less desired 4-GOL or containing desired product CBGV without its undesired isomer. Yet a further advantage is that subsequent steps to purify the decarboxylated cannabinoid can avoid an isomer separation step. With orsellinic acid all of the non-natural prenyltransferases showed increased specificity to produce 3-GOSA compared to wild-type, since all of the ratios of the relative levels of 3-GOSA to 5-GOSA were greater than the 1:1 ratio of the wild-type enzyme. Furthermore at least four variants resulted in less relative 5-GOSA production than wild-type, with two of those producing no 5-GOSA. These unique compositions provide a further advantage that subsequent steps to purify the cannabinoid can avoid an isomer separation step or, where less of the undesired isomer is present, provide an advantage of minimizing such an operation step. Similarly, decarboxylation of these mixtures provides the advantage of compositions containing desired CBGO without its undesirable isomer or having less of its undesirable isomer.

The results with the alcohol substrate are shown in the following Table 2 as relative fold increase over production by wild-type SEQ ID NO:2 enzyme.

TABLE 2

| | | Substrate | |
|---|---|---|---|
| | | Olivetolic acid | Olivetol |
| | | Product | |
| NphB variant | Mutations | CBGA 3-GOLA Relative fold increase | Cannabigerol (CBG, 2-GOL) Relative fold increase |
| Seq1C | Q159S S212H Y286V | 67 | 59.1 |
| Seq1D | Q161S S214H Y288V and GS insertion at position 45 | 72 | 91.2 |
| Seq1B | Q159H Q293W | 48 | 1.1 |
| Seq2H | Q161R Q295V | 10 | 0 |
| Seq2J | S214H | 9 | 2.5 |
| Seq2J | Q161H | 28 | 6.8 |
| Seq2B | Y288V | 10 | 0.9 |
| Seq2M | Q161H Q295W | 84 | 55.6 |
| Seq2DN | Q161S S214H Y288V | 86 | 129.9 |
| Seq2CP | Y288I Q295V | 48 | 13.5 |
| Seq2CQ | Q161H Y288I Q295W | 80 | 98.5 |
| Seq2CS | Q161H Y288V Q295M | 53 | 33.6 |
| Seq2CV | Q161H Q295V | 85 | 25.4 |

The wild-type enzyme produced a mixture of CBG and its less desired 4-GOL isomer. Except for one variant, the non-natural prenyltransferases were superior to wild-type enzyme in amount of CBG produced with olivetol as substrate. In addition, the non-natural prenyltransferases did not produce 4-GOL, providing unique compositions of product CBG.

These unique compositions provide a further advantage that subsequent steps to purify the cannabinoid can avoid an isomer separation step. In addition, the non-natural prenyltransferases provide a means to generate the desired CBG directly without the need for producing and decarboxylating an acid precursor.

What is claimed is:

1. A non-natural prenyltransferase based on a template of a wild type prenyltransferase that has 75% or greater identity to SEQ ID NO:1 or to any one of SEQ ID NO:2-3, the non-natural prenyltransferase comprising (A) at least one amino acid variation as compared to the wild type prenyltransferase at position(s) selected from the group consisting of: 49, 121, 124, 159, 175, 212, 232, 267, 268, 285, 286, 293, and 300, relative to SEQ ID NO:1, wherein the variation at position 49 is optionally S49T, the variation at position 121 is F121L, the variation at position 124 is T124R, the variation at position 159 is selected from the group consisting of Q159H, Q159R, Q159S, Q159Y, Q159F, Q159G, Q159I, Q159K, Q159L, Q159M, the variation at position 175 is selected from the group consisting of S175H, S175K, S175R, the variation at position 212 is S212H, the variation at position 232 is optionally I232H, the variation at position 267 is T267W, the variation at position 268 is optionally L268Y, the variation at position 285 is A285Y, the variation at position 286 is selected from the group consisting of Y286F, Y286L, Y286M, Y286P, Y286I, Y286T, Y286V, the variation at position 293 is selected from the group consisting of Q293F, Q293W, Q293H, Q293C, Q293S, Q293V, Q293D, Q293Y, Q293E, Q293I, Q293M, Q293T, and the variation at position 300 is optionally F300K, or (B) at least two amino acid variations as compared to the wild type prenyltransferase, the at least two variations at positions selected from the group consisting of 49, 121, 124, 159, 175, 212, 232, 267, 268, 285, 286, 293, and 300, relative to SEQ ID NO:1, wherein non-natural prenyltransferase is enzymatically capable of (a1) at least two-fold greater rate of formation of 3-geranyl-olivetolate (3-GOLA) from geranyl pyrophosphate and olivetolic acid, as compared to the wild type prenyltransferase; (a2) providing regioselectivity to 3-GOLA; or both (a1) and (a2)

(b1) at least two fold greater rate of formation of cannabigerovarinic acid (CBGVA) from geranyl pyrophosphate and divarinolic acid (DVA), as compared to the wild type prenyltransferase; (b2) 50% or greater regioselectivity to 3-geranyl-divarinolic acid (3-GDVA), or both (b1) and (b2);

(c1) at least two-fold greater rate of formation of cannabigerorcinic acid (CBGOA) from geranyl pyrophosphate and orsellinic acid (OSA), as compared to the wild type prenyltransferase; (c2) 50% or greater regioselectivity to 3-geranyl-orsellinate (3-GOSA); or both (c1) and (c2); or (d1) enzymatically capable of regioselectively forming a 2-prenylated 5-alkylbenzene-1,3-diol from geranyl pyrophosphate and 5-alkylbenzene-1,3-diol.

2. The non-natural prenyltransferase of claim 1 enzymatically capable of (a) at least five-fold greater rate of formation of 3-GOLA from geranyl pyrophosphate and olivetolic acid, as compared to the wild type prenyltransferase (b) 90% or greater regioselectivity to 3-GOLA, or both (a) and (b).

3. The non-natural prenyltransferase of claim 1 enzymatically capable of (i) at least fifty-fold greater rate of formation of: (a) cannabigerovarinic acid (CBGVA) from geranyl pyrophosphate and divarinolic acid (DVA), or (b) cannabigerorcinic acid (CBGOA) from geranyl pyrophosphate and orsellinic acid (OSA), as compared to the wild type prenyltransferase, (ii) 90% or greater regioselectivity to 3-geranyl-divarinolic acid (3-GDVA) or 3-geranyl-orsellinate (3-GOSA), or both (i) and (ii).

4. The non-natural prenyltransferase of claim 1 comprising at least two amino acid variations as compared to the template of the wild type prenyltransferase.

5. The non-natural prenyltransferase of claim 1 having 90% or greater identity to SEQ ID NO:1 or to any one of SEQ ID NO:2-3.

6. The non-natural prenyltransferase of claim 1 comprising one or more amino acid variations at position(s) selected from the group consisting of: 49, 121, 124, 159, 175, 212, 232, 267, 268, 285, 286, 293, and 300, relative to SEQ ID NO:1, wherein the one or more amino acid variations at position(s) 49, 121, 124, 159, 175, 212, 232, 267, 268, 285, 286, 293, and 300 is or are selected from the group consisting of: S49T, F121L, T124R, Q159H, Q159R, Q159S, Q159Y, Q159F, Q159G, Q159I, Q159K, Q159L, Q159M, S175H, S175K, S175R, S212H, 1232H, T267W, L268Y, A285Y, Y286F, Y286L, Y286M, Y286P, Y286I, Y286T, Y286V, Q293F, Q293W, Q293H, Q293C, Q293S, Q293V, Q293D, Q293Y, Q293E, Q293I, Q293M, Q293T, and F300K.

7. The non-natural prenyltransferase of claim 1 comprising at least two amino acid variations at positions selected from:

(i) Q159A and (ii) Q293F, Q293M, Q293F, Q293F;
(i) Q159F and (ii) Q293F, Q293W, or Q293H;
(i) Q159G and (ii) Q293F;
(i) Q159H and (ii) Q293W, Q293H, Q293C, Q293A, Q293S, Q293V, Q293D, Q293Y, or Q293E;
(i) Q159I and (ii) Q293F;
(i) Q159K and (ii) Q293V or Q293V;
(i) Q159L and (ii) Q293W or Q293F;
(i) Q159M and (ii) Q293F or Q293W;
(i) Q159R and (ii) Q293V, Q293M, or Q293T;
(i) Q159S and (ii) Y286I; and
(i) S175H and (ii) Q293V.

8. The non-natural prenyltransferase of claim 7 comprising at least three amino acid variations at positions selected from (i) Q159H, (ii) Y286A, and (iii) Q293F, Q293M, or Q293V;
(i) Q159H, (ii) Y286I, and (iii) Q293M or Q293V;
(i) Q159H, (ii) Y286V, and (iii) Q293F, Q293M, Q293V, or Q293W;
(i) Q159L, (ii) S175H, and (iii) Q293F;
(i) S175H, (ii), Y286V, and (iii) Q293M;
(i) S175H, (ii), Y286I, and (iii) Q293M or Q293V;
(i) Q159S, (ii) S175H, and (iii) Y286I;
(i) Q159S, (ii) S175R, and (iii) Y286V;
(i) Q159S, (ii) S175S, and (iii) Y286I; and
(i) Q159S, (ii) S212H, (iii) Y286A or Y286V.

9. The non-natural prenyltransferase of claim 7 comprising at least four amino acid variations at positions selected from:

(i) Q159H, (ii) S175H, (iii) Y286A, and (iv) Q293V;
(i) Q159H, (ii) S175H, (iii) Y286V, and (iv) Q293M or Q293V;
(i) Q159H, (ii) S175R, (iii) Y286I, and (iv) Q293M;
(i) Q159L, (ii) S175K, (iii) Y286A, and (iv) Q293V;
(i) Q159M, (ii) S175H, (iii) Y286V, and (iv) Q293F;
(i) Q159R, (ii) S175H, (iii) Y286I, and (iv) Q293Q;
(i) Q159S, (ii) S175H, (iii) Y286V, and (iv) Q293F;
(i) Q159S, (ii) S175K, (iii) Y286V, and (iv) Q293V; and
(i) Q159S, (ii) S212H, (iii) Y286V, and (iv) Q293M, or comprising at least five amino acid variations at positions selected from:

(i) Q159H, (ii) S175R, (iii) S212H, (iv) Y286A, and (v) Q293V; and
(i) Q159R, (ii) S175R, (iii) S212H, (iv) Y286I, and (v) Q293M.

10. The non-natural prenyltransferase of claim 1 comprising one or more amino acid variations at position(s) selected from the group consisting of: 51, 123, 126, 161, 177, 214, 234, 269, 270, 287, 288, 295, and 302, relative to SEQ ID NO:2, wherein optionally the one or more amino acid variations at position(s) selection from the group consisting of: S51T, F123L, T126R, Q161H, Q161R, Q161S, Q161T, Q161Y, Q161F, Q161G, Q161I, Q161K, Q161L, Q161M, Q161A, S177H, S177K, S177R, S214H, I234H, T269W, L270Y, A287Y, Y288F, Y288L, Y288M, Y288P, Y288I, Y288T, Y288V, Q295F, Q295W, Q295H, Q295C, Q295S, Q295V, Q295D, Q295Y, Q295E, Q295I, Q295M, Q295T, and F302K.

11. The non-natural prenyltransferase of claim 10 comprising one or more amino acid variations at position(s) selection from the group consisting of:

(a) Q161H;
(b) S214H;
(c) Y288V;
(d) Q161R and Q295V;
(e) Q161H and Q295W;
(f) Q161H and Q295V
(g) Y288I and Q295V;
(h) Q161S, S214H, and Y288V;
(i) Q161H, Y288I, and Q295W; and
(j) Q161H, Y288V, and Q295M.

12. A nucleic acid encoding the non-natural prenyltransferase of claim 1, wherein the nucleic acid is optionally in the form of an expression construct.

13. An engineered cell comprising the non-natural prenyltransferase of claim 1.

14. The engineered cell of claim 13 comprising (i) an olivetolic acid pathway, optionally comprising a polyketide synthase/olivetol synthase (condensation of hexanoyl coenzyme A (CoA) and malonyl CoA);

(ii) a DVA or OSA pathway;

(iii) an olivetol pathway, optionally comprising polyketide synthase; or (iv) a geranyl pyrophosphate pathway (GPP), optionally comprising geranyl pyrophosphate synthase, and optionally comprising a mevalonate (MVA) pathway, a MEP pathway, or any two or more of (i)-(iv).

15. A non-natural prenyltransferase having 75% or greater identity to SEQ ID NO:1 or to any one of SEQ ID NO:2-3, the non-natural prenyltransferase comprising (A) at least one amino acid variation as at position(s) selected from the group consisting of: 49, 121, 124, 159, 175, 212, 232, 267, 268, 285, 286, 293, and 300, relative to SEQ ID NO:1, wherein the variation at position 49 is optionally S49T, the variation at position 121 is F121L, the variation at position 124 is T124R, the variation at position 159 is selected from the group consisting of Q159H, Q159R, Q159S, Q159Y, Q159F, Q159G, Q159I, Q159K, Q159L, Q159M, the variation at position 175 is selected from the group consisting of S175H, S175K, S175R, the variation at position 212 is S212H, the variation at position 232 is optionally I232H, the variation at position 267 is T267W, the variation at position 268 is optionally L268Y, the variation at position 285 is A285Y, the variation at position 286 is selected from the group consisting of Y286F, Y286L, Y286M, Y286P, Y286I, Y286T, Y286V, the variation at position 293 is selected from the group consisting of Q293F, Q293W, Q293H, Q293C, Q293S, Q293V, Q293D, Q293Y, Q293E, Q293I, Q293M, Q293T, and the variation at position 300 is optionally F300K, or (B) at least two amino acid variations as compared to the wild type prenyltransferase, the at least two variations at positions selected from the group consisting of 49, 121, 124, 159, 175, 212, 232, 267, 268, 285, 286, 293, and 300, relative to SEQ ID NO:1.

16. The non-natural prenyltransferase of claim 15 comprising:

(I) at least two amino acid variations at positions selected from:

(i) Q159A and (ii) Q293F, Q293M, Q293F, Q293F;

(i) Q159F and (ii) Q293F, Q293W, or Q293H;

(i) Q159G and (ii) Q293F;

(i) Q159H and (ii) Q293W, Q293H, Q293C, Q293A, Q293S, Q293V, Q293D, Q293Y, or Q293E;

(i) Q159I and (ii) Q293F;

(i) Q159K and (ii) Q293V or Q293V;

(i) Q159L and (ii) Q293W or Q293F;

(i) Q159M and (ii) Q293F or Q293W;

(i) Q159R and (ii) Q293V, Q293M, or Q293T;

(i) Q159S and (ii) Y286I; and (i) S175H and (ii) Q293V;

(II) comprising at least three amino acid variations at positions selected from (i) Q159H, (ii) Y286A, and (iii) Q293F, Q293M, or Q293V;

(i) Q159H, (ii) Y286I, and (iii) Q293M or Q293V;

(i) Q159H, (ii) Y286V, and (iii) Q293F, Q293M, Q293V, or Q293W;

(i) Q159L, (ii) S175H, and (iii) Q293F;

(i) S175H, (ii), Y286V, and (iii) Q293M;

(i) S175H, (ii), Y286L, and (iii) Q293M or Q293V;

(i) Q159S, (ii) S175H, and (iii) Y286I;

(i) Q159S, (ii) S175R, and (iii) Y286V;

(i) Q159S, (ii) S175S, and (iii) Y286I; and (i) Q159S, (ii) S212H, (iii) Y286A or Y286V;

(III) comprising at least four amino acid variations at positions selected from:

(i) Q159H, (ii) S175H, (iii) Y286A, and (iv) Q293V;

(i) Q159H, (ii) S175H, (iii) Y286V, and (iv) Q293M or Q293V;

(i) Q159H, (ii) S175R, (iii) Y286I, and (iv) Q293M;

(i) Q159L, (ii) S175K, (iii) Y286A, and (iv) Q293V;

(i) Q159M, (ii) S175H, (iii) Y286V, and (iv) Q293F;

(i) Q159R, (ii) S175H, (iii) Y286I, and (iv) Q293Q;

(i) Q159S, (ii) S175H, (iii) Y286V, and (iv) Q293F;

(i) Q159S, (ii) S175K, (iii) Y286V, and (iv) Q293V; and (i) Q159S, (ii) S212H, (iii) Y286V, and (iv) Q293M, or (IV) comprising at least five amino acid variations at positions selected from:

(i) Q159H, (ii) S175R, (iii) S212H, (iv) Y286A, and (v) Q293V; and (i) Q159R, (ii) S175R, (iii) S212H, (iv) Y286I, and (v) Q293M.

17. The non-natural prenyltransferase of claim 15 having 90% or greater identity to SEQ ID NO:1 or to any one of SEQ ID NO:2-3.

18. The non-natural prenyltransferase of claim 15 comprising one or more amino acid variations selected from the group consisting of: S49T, F121L, T124R, Q159H, Q159R, Q159S, Q159Y, Q159F, Q159G, Q159I, Q159K, Q159L, Q159M, S175H, S175K, S175R, S212H, I232H, T267W, L268Y, A285Y, Y286F, Y286L, Y286M, Y286P, Y286I, Y286T, Y286V, Q293F, Q293W, Q293H, Q293C, Q293S, Q293V, Q293Y, Q293E, Q293I, Q293M, Q293T, and F300K relative to SEQ ID NO:1, or two or more amino acid variations selected from the group consisting of: S49T, F121L, T124R, Q159H, Q159R, Q159S, Q159T, Q159Y, Q159A, Q159F, Q159G, Q159I, Q159K, Q159L, Q159M, S175H, S175K, S175R, S212H, I232H, T267W, L268Y, A285Y, Y286A, Y286F, Y286L, Y286M, Y286P, Y286I, Y286T, Y286V, Q293F, Q293W, Q293H, Q293C, Q293A, Q293S, Q293V, Q293D, Q293Y, Q293E, Q293I, Q293M, Q293T, and F300K relative to SEQ ID NO:1.

* * * * *